(12) United States Patent
Robb et al.

(10) Patent No.: US 8,944,816 B2
(45) Date of Patent: Feb. 3, 2015

(54) TEMPORARY ABUTMENT WITH COMBINATION OF SCANNING FEATURES AND PROVISIONALIZATION FEATURES

(75) Inventors: T. Tait Robb, Carlsbad, CA (US); Stephen M. Herrington, Naples, FL (US); Miguel Montero, West Palm Beach, FL (US); Ralph E. Goodman, West Palm Beach, FL (US); Dan P. Rogers, North Palm Beach, FL (US); John J. Bellanca, West Palm Beach, FL (US); Zachary B. Suttin, Palm Beach Gardens, FL (US)

(73) Assignee: Biomet 3i, LLC, Palm Beach Gardens, FL (US)

( * ) Notice: Subject to any disclaimer, the term of this patent is extended or adjusted under 35 U.S.C. 154(b) by 0 days.

(21) Appl. No.: 13/473,202

(22) Filed: May 16, 2012

(65) Prior Publication Data
US 2012/0295223 A1    Nov. 22, 2012

Related U.S. Application Data

(60) Provisional application No. 61/486,630, filed on May 16, 2011.

(51) Int. Cl.
*A61C 13/225* (2006.01)
*A61C 8/00* (2006.01)

(52) U.S. Cl.
CPC ............. *A61C 8/008* (2013.01); *A61C 8/006* (2013.01); *A61C 8/0068* (2013.01); *A61C 8/0024* (2013.01); *A61C 2008/0084* (2013.01)
USPC .......................................... 433/172

(58) Field of Classification Search
CPC ...................................................... A61C 8/008
USPC ....................................... 433/172–177, 201.1
See application file for complete search history.

(56) References Cited

U.S. PATENT DOCUMENTS

| | | |
|---|---|---|
| 3,906,634 A | 9/1975 | Aspel |
| 3,919,772 A | 11/1975 | Lenczycki |

(Continued)

FOREIGN PATENT DOCUMENTS

| | | |
|---|---|---|
| DE | 10029256 | 11/2000 |
| WO | WO 94/26200 | 11/1994 |

(Continued)

OTHER PUBLICATIONS

BIOMET 3i—Manual entitled "Navigator™ System for CT Guided Surgery Manual", Revision A 10/07—34 pages.

(Continued)

*Primary Examiner* — Cris L Rodriguez
*Assistant Examiner* — Matthew Seward
(74) *Attorney, Agent, or Firm* — Nixon Peabody LLP

(57) ABSTRACT

A lower region of a temporary abutment includes an anti-rotational feature for non-rotationally mating with a dental implant. An upper region of the temporary abutment includes a first anti-rotational structure and at least one retention groove. A top surface of the temporary abutment includes one or more informational markers that provide information concerning the dental implant. A temporary abutment cap is configured to be coupled to the upper region of the temporary abutment. The temporary abutment cap has at least one projection configured to mate with the at least one retention groove of the temporary abutment. The temporary abutment cap has a second anti-rotational structure that is configured to slidably engage the first anti-rotational structure of the temporary abutment. The temporary abutment cap is configured to be coupled with a temporary prosthesis such that the temporary prosthesis and the temporary abutment cap are removable from the temporary abutment.

8 Claims, 31 Drawing Sheets

(56) References Cited

U.S. PATENT DOCUMENTS

| | | |
|---|---|---|
| 3,958,471 A | 5/1976 | Muller |
| 4,011,602 A | 3/1977 | Rybicki et al. |
| 4,056,585 A | 11/1977 | Waltke |
| 4,086,701 A | 5/1978 | Kawahara et al. |
| 4,177,562 A | 12/1979 | Miller et al. |
| 4,294,544 A | 10/1981 | Altschuler et al. |
| 4,306,862 A | 12/1981 | Knox |
| 4,325,373 A | 4/1982 | Slivenko et al. |
| 4,341,312 A | 7/1982 | Scholer |
| 4,364,381 A | 12/1982 | Sher et al. |
| 4,439,152 A | 3/1984 | Small |
| 4,543,953 A | 10/1985 | Slocum et al. |
| 4,547,157 A | 10/1985 | Driskell |
| 4,571,180 A | 2/1986 | Kulick |
| 4,611,288 A | 9/1986 | Duret et al. |
| 4,624,673 A | 11/1986 | Meyer |
| 4,663,720 A | 5/1987 | Duret et al. |
| 4,713,004 A | 12/1987 | Linkow et al. |
| 4,756,689 A | 7/1988 | Lundgren |
| 4,758,161 A | 7/1988 | Niznick |
| 4,767,331 A | 8/1988 | Hoe |
| 4,772,204 A | 9/1988 | Soderberg |
| 4,821,200 A | 4/1989 | Öberg |
| 4,842,518 A | 6/1989 | Linkow et al. |
| 4,850,870 A | 7/1989 | Lazzara et al. |
| 4,850,873 A | 7/1989 | Lazzara et al. |
| 4,854,872 A | 8/1989 | Detsch |
| 4,856,994 A | 8/1989 | Lazzara et al. |
| 4,872,839 A | 10/1989 | Brajnovic |
| 4,906,191 A | 3/1990 | Soderberg |
| 4,906,420 A | 3/1990 | Brajnovic |
| 4,931,016 A | 6/1990 | Sillard |
| 4,935,635 A | 6/1990 | O'Harra |
| 4,961,674 A | 10/1990 | Wang et al. |
| 4,964,770 A | 10/1990 | Steinbichler et al. |
| 4,986,753 A | 1/1991 | Sellers |
| 4,988,297 A | 1/1991 | Lazzara et al. |
| 4,988,298 A | 1/1991 | Lazzara et al. |
| 4,998,881 A | 3/1991 | Lauks |
| 5,000,685 A | 3/1991 | Brajnovic |
| 5,006,069 A | 4/1991 | Lazzara et al. |
| 5,015,183 A | 5/1991 | Fenick |
| 5,015,186 A | 5/1991 | Detsch |
| 5,030,096 A | 7/1991 | Hurson et al. |
| 5,035,619 A | 7/1991 | Daftary |
| 5,040,982 A | 8/1991 | Stefan-Dogar |
| 5,040,983 A | 8/1991 | Binon |
| 5,064,375 A | 11/1991 | Jörnéus |
| 5,071,351 A | 12/1991 | Green, Jr. et al. |
| 5,073,111 A | 12/1991 | Daftary |
| 5,087,200 A | 2/1992 | Brajnovic et al. |
| 5,100,323 A | 3/1992 | Friedman et al. |
| 5,104,318 A | 4/1992 | Piche et al. |
| 5,106,300 A | 4/1992 | Voitik |
| 5,122,059 A | 6/1992 | Dürr et al. |
| 5,125,839 A | 6/1992 | Ingber et al. |
| 5,125,841 A | 6/1992 | Carlsson et al. |
| 5,133,660 A | 7/1992 | Fenick |
| 5,135,395 A | 8/1992 | Marlin |
| 5,145,371 A | 9/1992 | Jörnéus |
| 5,145,372 A | 9/1992 | Daftary et al. |
| 5,176,516 A | 1/1993 | Koizumi |
| 5,188,800 A | 2/1993 | Green, Jr. et al. |
| 5,195,892 A | 3/1993 | Gersberg |
| 5,205,745 A | 4/1993 | Kamiya et al. |
| 5,209,659 A | 5/1993 | Friedman et al. |
| 5,209,666 A | 5/1993 | Balfour et al. |
| 5,213,502 A | 5/1993 | Daftary |
| 5,221,204 A | 6/1993 | Kruger et al. |
| 5,237,998 A | 8/1993 | Duret et al. |
| 5,246,370 A | 9/1993 | Coatoam |
| 5,257,184 A | 10/1993 | Mushabac |
| 5,281,140 A | 1/1994 | Niznick |
| 5,286,195 A | 2/1994 | Clostermann |
| 5,286,196 A | 2/1994 | Brajnovic et al. |
| 5,292,252 A | 3/1994 | Nickerson et al. |
| 5,297,963 A | 3/1994 | Dafatry |
| 5,302,125 A | 4/1994 | Kownacki et al. |
| 5,312,254 A | 5/1994 | Rosenlicht |
| 5,312,409 A | 5/1994 | McLaughlin et al. |
| 5,316,476 A | 5/1994 | Krauser |
| 5,320,529 A | 6/1994 | Pompa |
| 5,328,371 A | 7/1994 | Hund et al. |
| 5,333,898 A | 8/1994 | Stutz |
| 5,334,024 A | 8/1994 | Niznick |
| 5,336,090 A | 8/1994 | Wilson, Jr. et al. |
| 5,338,196 A | 8/1994 | Beaty et al. |
| 5,338,198 A | 8/1994 | Wu et al. |
| 5,343,391 A | 8/1994 | Mushabac |
| 5,344,457 A | 9/1994 | Pilliar et al. |
| 5,350,297 A | 9/1994 | Cohen |
| 5,359,511 A | 10/1994 | Schroeder et al. |
| 5,362,234 A | 11/1994 | Salazar et al. |
| 5,362,235 A | 11/1994 | Daftary |
| 5,368,483 A | 11/1994 | Sutter et al. |
| 5,370,692 A | 12/1994 | Fink |
| 5,372,502 A | 12/1994 | Massen et al. |
| 5,386,292 A | 1/1995 | Massen et al. |
| 5,413,481 A | 5/1995 | Göppel et al. |
| 5,417,569 A | 5/1995 | Perisse |
| 5,417,570 A | 5/1995 | Zuest et al. |
| 5,419,702 A | 5/1995 | Beaty et al. |
| 5,431,567 A | 7/1995 | Datary |
| 5,437,551 A | 8/1995 | Chalifoux |
| 5,440,393 A | 8/1995 | Wenz |
| 5,452,219 A | 9/1995 | Dehoff et al. |
| 5,458,488 A | 10/1995 | Chalifoux |
| 5,476,382 A | 12/1995 | Daftary |
| 5,476,383 A | 12/1995 | Beaty et al. |
| 5,492,471 A | 2/1996 | Singer |
| 5,516,288 A | 5/1996 | Sichler et al. |
| 5,527,182 A | 6/1996 | Willoughby |
| 5,533,898 A | 7/1996 | Mena |
| 5,538,426 A | 7/1996 | Harding et al. |
| 5,547,377 A | 8/1996 | Daftary |
| 5,556,278 A | 9/1996 | Meitner |
| 5,561,675 A | 10/1996 | Bayon et al. |
| 5,564,921 A | 10/1996 | Marlin |
| 5,564,924 A | 10/1996 | Kwan |
| 5,569,578 A | 10/1996 | Mushabac |
| 5,575,656 A | 11/1996 | Hajjar |
| 5,580,244 A | 12/1996 | White |
| 5,580,246 A | 12/1996 | Fried |
| 5,595,703 A | 1/1997 | Swaelens et al. |
| 5,613,832 A | 3/1997 | Su |
| 5,613,852 A | 3/1997 | Bavitz |
| 5,630,717 A | 5/1997 | Zuest |
| 5,636,986 A | 6/1997 | Prezeshkian |
| 5,651,675 A | 7/1997 | Singer |
| 5,652,709 A | 7/1997 | Andersson et al. |
| 5,658,147 A | 8/1997 | Phimmasone |
| 5,662,476 A | 9/1997 | Ingber et al. |
| 5,674,069 A | 10/1997 | Osorio |
| 5,674,071 A | 10/1997 | Beaty et al. |
| 5,674,073 A | 10/1997 | Ingber et al. |
| 5,681,167 A | 10/1997 | Lazarof |
| 5,685,715 A | 11/1997 | Beaty et al. |
| 5,688,283 A | 11/1997 | Knapp |
| 5,704,936 A | 1/1998 | Mazel |
| 5,718,579 A | 2/1998 | Kennedy |
| 5,725,376 A | 3/1998 | Poirier |
| 5,733,124 A | 3/1998 | Kwan |
| 5,741,215 A | 4/1998 | D'Urso |
| 5,743,916 A | 4/1998 | Greenberg |
| 5,759,036 A | 6/1998 | Hinds |
| 5,762,125 A | 6/1998 | Mastrorio |
| 5,762,500 A | 6/1998 | Lazarof |
| 5,768,134 A | 6/1998 | Swaelens et al. |
| 5,769,636 A | 6/1998 | Di Sario |
| 5,791,902 A | 8/1998 | Lauks |
| 5,800,168 A | 9/1998 | Cascione et al. |
| 5,813,858 A | 9/1998 | Singer |
| 5,823,778 A | 10/1998 | Schmitt et al. |
| 5,842,859 A | 12/1998 | Palacci |

(56) References Cited

U.S. PATENT DOCUMENTS

| | | |
|---|---|---|
| 5,846,079 A | 12/1998 | Knode |
| 5,851,115 A | 12/1998 | Carlsson et al. |
| 5,857,853 A | 1/1999 | Van Nifterick et al. |
| 5,871,358 A | 2/1999 | Ingber et al. |
| 5,873,722 A | 2/1999 | Lazzara et al. |
| 5,876,204 A | 3/1999 | Day et al. |
| 5,885,078 A | 3/1999 | Cagna et al. |
| 5,888,034 A | 3/1999 | Greenberg |
| 5,904,483 A | 5/1999 | Wade |
| 5,915,962 A | 6/1999 | Rosenlicht |
| 5,927,982 A | 7/1999 | Kruger |
| 5,938,443 A | 8/1999 | Lazzara et al. |
| 5,954,769 A | 9/1999 | Rosenlicht |
| 5,964,591 A | 10/1999 | Beaty et al. |
| 5,967,777 A | 10/1999 | Klein et al. |
| 5,984,681 A | 11/1999 | Huang |
| 5,989,025 A | 11/1999 | Conley |
| 5,989,029 A | 11/1999 | Osorlo |
| 5,989,258 A | 11/1999 | Hattori |
| 5,997,681 A | 12/1999 | Kinzie |
| 6,000,939 A | 12/1999 | Ray et al. |
| 6,008,905 A | 12/1999 | Breton et al. |
| 6,068,479 A | 5/2000 | Kwan |
| 6,099,311 A | 8/2000 | Wagner et al. |
| 6,099,313 A | 8/2000 | Dorken et al. |
| 6,099,314 A | 8/2000 | Kopelman et al. |
| 6,120,293 A | 9/2000 | Lazzara et al. |
| 6,129,548 A | 10/2000 | Lazzara et al. |
| 6,135,773 A | 10/2000 | Lazzara |
| 6,142,782 A | 11/2000 | Lazarof |
| 6,174,168 B1 | 1/2001 | Dehoff et al. |
| 6,175,413 B1 | 1/2001 | Lucas |
| 6,190,169 B1 | 2/2001 | Bluemli et al. |
| 6,197,410 B1 | 3/2001 | Vallittu et al. |
| 6,200,125 B1 | 3/2001 | Akutagawa |
| 6,206,693 B1 | 3/2001 | Hultgren |
| 6,210,162 B1 | 4/2001 | Chishti |
| 6,217,334 B1 | 4/2001 | Hultgren |
| 6,227,859 B1 | 5/2001 | Sutter |
| 6,283,753 B1 | 9/2001 | Willoughby |
| 6,287,119 B1 | 9/2001 | van Nifterick |
| 6,296,483 B1 | 10/2001 | Champleboux |
| 6,305,939 B1 | 10/2001 | Dawood |
| 6,319,000 B1 | 11/2001 | Branemark |
| 6,322,728 B1 | 11/2001 | Brodkin |
| 6,382,975 B1 | 5/2002 | Poirier |
| 6,402,707 B1 | 6/2002 | Ernst |
| 6,431,866 B2 * | 8/2002 | Hurson .................. 433/172 |
| 6,431,867 B1 | 8/2002 | Gittelson et al. |
| 6,488,503 B1 | 12/2002 | Lichkus et al. |
| 6,497,574 B1 | 12/2002 | Miller |
| 6,540,784 B2 | 4/2003 | Barlow |
| 6,558,162 B1 | 5/2003 | Porter et al. |
| 6,568,936 B2 | 5/2003 | MacDougald |
| 6,575,751 B1 | 6/2003 | Lehmann et al. |
| 6,594,539 B1 | 7/2003 | Geng |
| 6,610,079 B1 | 8/2003 | Li |
| 6,619,958 B2 | 9/2003 | Beaty et al. |
| 6,629,840 B2 | 10/2003 | Chishti |
| 6,634,883 B2 | 10/2003 | Ranalli |
| 6,644,970 B1 * | 11/2003 | Lin .................. 433/173 |
| 6,648,640 B2 | 11/2003 | Rubbert et al. |
| 6,671,539 B2 | 12/2003 | Gateno et al. |
| 6,672,870 B2 | 1/2004 | Knapp |
| 6,688,887 B2 | 2/2004 | Morgan |
| 6,691,764 B2 | 2/2004 | Embert |
| 6,726,480 B1 * | 4/2004 | Sutter .................. 433/173 |
| 6,743,491 B2 | 6/2004 | Cirincione et al. |
| 6,755,652 B2 | 6/2004 | Nanni |
| 6,772,026 B2 | 8/2004 | Bradbury |
| 6,776,614 B2 | 8/2004 | Wiechmann et al. |
| 6,783,359 B2 | 8/2004 | Kapit |
| 6,790,040 B2 | 9/2004 | Amber et al. |
| 6,793,491 B2 | 9/2004 | Klein et al. |
| 6,808,659 B2 | 10/2004 | Schulman |
| 6,814,575 B2 | 11/2004 | Poirier |
| 6,821,462 B2 | 11/2004 | Schulamn et al. |
| 6,829,498 B2 | 12/2004 | Kipke et al. |
| D503,804 S | 4/2005 | Phleps et al. |
| 6,882,894 B2 | 4/2005 | Durbin et al. |
| 6,885,464 B1 | 4/2005 | Pfeiffer et al. |
| 6,902,401 B2 | 6/2005 | Jorneus et al. |
| 6,913,463 B2 | 7/2005 | Blacklock |
| 6,926,442 B2 | 8/2005 | Stöckl |
| 6,926,525 B1 | 8/2005 | Ronvig |
| 6,939,489 B2 | 9/2005 | Moszner et al. |
| 6,942,699 B2 | 9/2005 | Stone et al. |
| 6,953,383 B2 | 10/2005 | Rothenberger |
| 6,957,118 B2 | 10/2005 | Kopelman et al. |
| 6,966,772 B2 | 11/2005 | Malin et al. |
| 6,970,760 B2 | 11/2005 | Wolf et al. |
| 6,971,877 B2 | 12/2005 | Harter |
| 6,994,549 B2 | 2/2006 | Brodkin et al. |
| 7,010,150 B1 | 3/2006 | Pfeiffer et al. |
| 7,010,153 B2 | 3/2006 | Zimmermann |
| 7,012,988 B2 | 3/2006 | Adler et al. |
| 7,018,207 B2 | 3/2006 | Prestipino |
| 7,021,934 B2 | 4/2006 | Aravena |
| 7,029,275 B2 | 4/2006 | Rubbert et al. |
| 7,044,735 B2 | 5/2006 | Malin |
| 7,056,115 B2 | 6/2006 | Phan et al. |
| 7,056,472 B1 | 6/2006 | Behringer |
| 7,059,856 B2 | 6/2006 | Marotta |
| 7,066,736 B2 | 6/2006 | Kumar et al. |
| 7,084,868 B2 | 8/2006 | Farag et al. |
| 7,086,860 B2 | 8/2006 | Schuman et al. |
| 7,097,451 B2 | 8/2006 | Tang |
| 7,104,795 B2 | 9/2006 | Dadi |
| 7,110,844 B2 | 9/2006 | Kopelman |
| 7,112,065 B2 | 9/2006 | Kopelman |
| 7,118,375 B2 | 10/2006 | Durbin et al. |
| D532,991 S | 12/2006 | Gozzi |
| 7,153,132 B2 | 12/2006 | Tedesco |
| 7,153,135 B1 | 12/2006 | Thomas |
| 7,163,443 B2 | 1/2007 | Basler et al. |
| 7,175,434 B2 | 2/2007 | Brajnovic |
| 7,175,435 B2 | 2/2007 | Andersson et al. |
| 7,178,731 B2 | 2/2007 | Basler |
| 7,214,062 B2 | 5/2007 | Morgan |
| 7,220,124 B2 | 5/2007 | Taub et al. |
| 7,228,191 B2 | 6/2007 | Hofmeister et al. |
| 7,236,842 B2 | 6/2007 | Kopelman et al. |
| 7,281,927 B2 | 10/2007 | Marotta |
| 7,286,954 B2 | 10/2007 | Kopelman et al. |
| 7,303,420 B2 | 12/2007 | Huch et al. |
| 7,319,529 B2 | 1/2008 | Babayoff |
| 7,322,746 B2 | 1/2008 | Beckhaus et al. |
| 7,322,824 B2 | 1/2008 | Schmitt |
| 7,324,680 B2 | 1/2008 | Zimmermann |
| 7,329,122 B1 | 2/2008 | Scott |
| 7,333,874 B2 | 2/2008 | Taub et al. |
| 7,335,876 B2 | 2/2008 | Eiff et al. |
| D565,184 S | 3/2008 | Royzen |
| 7,367,801 B2 | 5/2008 | Saliger |
| 7,379,584 B2 | 5/2008 | Rubbert et al. |
| D571,471 S | 6/2008 | Stöckl |
| 7,381,191 B2 | 6/2008 | Fallah |
| 7,383,094 B2 | 6/2008 | Kopelman et al. |
| D575,747 S | 8/2008 | Abramovich et al. |
| 7,421,608 B2 | 9/2008 | Schron |
| 7,425,131 B2 | 9/2008 | Amber et al. |
| 7,429,175 B2 | 9/2008 | Gittelson |
| 7,435,088 B2 | 10/2008 | Brajnovic |
| 7,476,100 B2 | 1/2009 | Kuo |
| 7,481,647 B2 | 1/2009 | Sambu et al. |
| 7,488,174 B2 | 2/2009 | Kopelman et al. |
| 7,497,619 B2 | 3/2009 | Stoeckl |
| 7,497,983 B2 | 3/2009 | Khan et al. |
| 7,520,747 B2 | 4/2009 | Stonisch |
| 7,522,764 B2 | 4/2009 | Schwotzer |
| 7,534,266 B2 | 5/2009 | Kluger |
| 7,536,234 B2 | 5/2009 | Kopelman et al. |
| 7,545,372 B2 | 6/2009 | Kopelman et al. |
| 7,551,760 B2 | 6/2009 | Scharlack et al. |

(56) References Cited

U.S. PATENT DOCUMENTS

| | | |
|---|---|---|
| 7,555,403 B2 | 6/2009 | Kopelman et al. |
| 7,556,496 B2 | 7/2009 | Cinader, Jr. et al. |
| 7,559,692 B2 | 7/2009 | Beckhaus et al. |
| 7,563,397 B2 | 7/2009 | Schulman et al. |
| D597,769 S | 8/2009 | Richter et al. |
| 7,572,058 B2 | 8/2009 | Pruss et al. |
| 7,572,125 B2 | 8/2009 | Brajnovic |
| 7,574,025 B2 | 8/2009 | Feldman |
| 7,578,673 B2 | 8/2009 | Wen et al. |
| 7,580,502 B2 | 8/2009 | Dalpiaz et al. |
| 7,581,951 B2 | 9/2009 | Lehmann et al. |
| 7,582,855 B2 | 9/2009 | Pfeiffer |
| 7,628,537 B2 | 12/2009 | Schulze-Ganzlin |
| 7,632,097 B2 | 12/2009 | De Clerck |
| 7,653,455 B2 | 1/2010 | Cnader, Jr. et al. |
| 7,654,823 B2 | 2/2010 | Dadi |
| 7,655,586 B1 | 2/2010 | Brodkin et al. |
| 7,658,610 B2 | 2/2010 | Knopp |
| 7,661,956 B2 | 2/2010 | Powell et al. |
| 7,665,989 B2 | 2/2010 | Brajnovic et al. |
| 7,679,723 B2 | 3/2010 | Schwotzer |
| 7,687,754 B2 | 3/2010 | Eiff et al. |
| 7,689,308 B2 | 3/2010 | Holzner et al. |
| D614,210 S | 4/2010 | Basler et al. |
| 7,698,014 B2 | 4/2010 | Dunne et al. |
| 7,774,084 B2 | 8/2010 | Cinader, Jr. |
| 7,780,907 B2 | 8/2010 | Schmidt et al. |
| 7,785,007 B2 | 8/2010 | Stoeckl |
| 7,787,132 B2 | 8/2010 | Körner et al. |
| 7,796,811 B2 | 9/2010 | Orth et al. |
| 7,798,708 B2 | 9/2010 | Erhardt et al. |
| 7,801,632 B2 | 9/2010 | Orth et al. |
| 7,815,371 B2 | 10/2010 | Schulze-Ganzlin |
| 7,824,181 B2 | 11/2010 | Sers |
| D629,908 S | 12/2010 | Jerger et al. |
| 7,855,354 B2 | 12/2010 | Eiff |
| 7,865,261 B2 | 1/2011 | Pfeiffer |
| 7,876,877 B2 | 1/2011 | Stockl |
| 7,901,209 B2 | 3/2011 | Saliger et al. |
| 7,982,731 B2 | 7/2011 | Orth et al. |
| 7,985,119 B2 | 7/2011 | Basler et al. |
| 7,986,415 B2 | 7/2011 | Thiel et al. |
| 7,988,449 B2 | 8/2011 | Amber et al. |
| 8,011,925 B2 | 9/2011 | Powell et al. |
| 8,011,927 B2 | 9/2011 | Berckmans, III et al. |
| 8,026,943 B2 | 9/2011 | Weber et al. |
| 8,038,440 B2 | 10/2011 | Swaelens et al. |
| 8,047,895 B2 | 11/2011 | Basler |
| 8,057,912 B2 | 11/2011 | Basler et al. |
| 8,062,034 B2 | 11/2011 | Hanisch et al. |
| 8,075,313 B2 | 12/2011 | Ranck et al. |
| 8,083,522 B2 | 12/2011 | Karkar et al. |
| 8,105,081 B2 | 1/2012 | Bavar |
| 8,226,654 B2 | 7/2012 | Ranck et al. |
| 2001/0008751 A1 | 7/2001 | Chishti et al. |
| 2001/0034010 A1 | 10/2001 | MacDougald et al. |
| 2002/0010568 A1 | 1/2002 | Rubbert et al. |
| 2002/0028418 A1 | 3/2002 | Farag et al. |
| 2002/0039717 A1 | 4/2002 | Amber et al. |
| 2002/0160337 A1 | 10/2002 | Klein et al. |
| 2002/0167100 A1 | 11/2002 | Moszner |
| 2003/0130605 A1 | 7/2003 | Besek |
| 2003/0222366 A1 | 12/2003 | Stangel |
| 2004/0029074 A1 | 2/2004 | Brajnovic |
| 2004/0048227 A1 | 3/2004 | Brajnovic |
| 2004/0180308 A1 | 9/2004 | Ebi et al. |
| 2004/0219477 A1 | 11/2004 | Harter |
| 2004/0219479 A1 | 11/2004 | Malin et al. |
| 2004/0219490 A1 | 11/2004 | Gartner et al. |
| 2004/0220691 A1 | 11/2004 | Hofmeister et al. |
| 2004/0241611 A1 | 12/2004 | Amber et al. |
| 2004/0243481 A1 | 12/2004 | Bradbury et al. |
| 2004/0259051 A1 | 12/2004 | Brajnovic |
| 2005/0023710 A1 | 2/2005 | Brodkin et al. |
| 2005/0056350 A1 | 3/2005 | Dolabdjian et al. |
| 2005/0070782 A1 | 3/2005 | Brodkin |
| 2005/0084144 A1 | 4/2005 | Feldman |
| 2005/0100861 A1 | 5/2005 | Choi et al. |
| 2005/0170311 A1 | 8/2005 | Tardieu et al. |
| 2005/0271996 A1 | 12/2005 | Sporbert et al. |
| 2005/0277089 A1 | 12/2005 | Brajnovic |
| 2005/0277090 A1 | 12/2005 | Anderson et al. |
| 2005/0277091 A1 | 12/2005 | Andersson et al. |
| 2005/0282106 A1 | 12/2005 | Sussman et al. |
| 2005/0283065 A1 | 12/2005 | Babayoff |
| 2006/0006561 A1 | 1/2006 | Brajnovic |
| 2006/0008763 A1 | 1/2006 | Brajnovic |
| 2006/0008770 A1 | 1/2006 | Brajnovic et al. |
| 2006/0093988 A1 | 5/2006 | Swaelens et al. |
| 2006/0094951 A1 | 5/2006 | Dean et al. |
| 2006/0127848 A1 | 6/2006 | Sogo et al. |
| 2006/0204928 A1* | 9/2006 | Hurson ........................ 433/173 |
| 2006/0210949 A1 | 9/2006 | Stoop |
| 2006/0263741 A1 | 11/2006 | Imgrund et al. |
| 2006/0263747 A1* | 11/2006 | Hurson ........................ 433/173 |
| 2006/0281041 A1 | 12/2006 | Rubbert et al. |
| 2007/0015111 A1 | 1/2007 | Kopelman et al. |
| 2007/0031790 A1 | 2/2007 | Raby et al. |
| 2007/0065777 A1 | 3/2007 | Becker |
| 2007/0077532 A1 | 4/2007 | Harter |
| 2007/0092854 A1* | 4/2007 | Powell et al. ................. 433/213 |
| 2007/0141525 A1 | 6/2007 | Cinader, Jr. |
| 2007/0211081 A1 | 9/2007 | Quadling et al. |
| 2007/0218426 A1 | 9/2007 | Quadling et al. |
| 2007/0269769 A1 | 11/2007 | Marchesi |
| 2007/0281277 A1 | 12/2007 | Brajnovic |
| 2008/0038692 A1 | 2/2008 | Andersson et al. |
| 2008/0044794 A1 | 2/2008 | Brajnovic |
| 2008/0057467 A1 | 3/2008 | Gittelson |
| 2008/0070181 A1 | 3/2008 | Abolfathi et al. |
| 2008/0085489 A1 | 4/2008 | Schmitt |
| 2008/0090210 A1 | 4/2008 | Brajnovic |
| 2008/0114371 A1 | 5/2008 | Kluger |
| 2008/0118895 A1 | 5/2008 | Brajnovic |
| 2008/0124676 A1 | 5/2008 | Marotta |
| 2008/0153060 A1 | 6/2008 | De Moyer |
| 2008/0153061 A1 | 6/2008 | Marcello |
| 2008/0153065 A1 | 6/2008 | Brajnovic et al. |
| 2008/0153069 A1 | 6/2008 | Holzner et al. |
| 2008/0176189 A1 | 7/2008 | Stonisch |
| 2008/0206714 A1 | 8/2008 | Schmitt |
| 2008/0233537 A1 | 9/2008 | Amber et al. |
| 2008/0233539 A1 | 9/2008 | Rossler et al. |
| 2008/0241798 A1 | 10/2008 | Holzner et al. |
| 2008/0261165 A1 | 10/2008 | Steingart et al. |
| 2008/0261176 A1* | 10/2008 | Hurson ........................ 433/174 |
| 2008/0286722 A1 | 11/2008 | Berckmans, III et al. |
| 2008/0300716 A1 | 12/2008 | Kopelman et al. |
| 2009/0017418 A1 | 1/2009 | Gittelson |
| 2009/0026643 A1 | 1/2009 | Wiest et al. |
| 2009/0042167 A1 | 2/2009 | Van Der Zel |
| 2009/0081616 A1 | 3/2009 | Pfeiffer |
| 2009/0087817 A1 | 4/2009 | Jansen et al. |
| 2009/0092948 A1 | 4/2009 | Gantes |
| 2009/0098510 A1 | 4/2009 | Zhang |
| 2009/0098511 A1 | 4/2009 | Zhang |
| 2009/0123045 A1 | 5/2009 | Quadling et al. |
| 2009/0123887 A1 | 5/2009 | Brajnovic |
| 2009/0130630 A1 | 5/2009 | Suttin et al. |
| 2009/0186319 A1 | 7/2009 | Sager |
| 2009/0187393 A1 | 7/2009 | Van Lierde et al. |
| 2009/0220134 A1 | 9/2009 | Cahill et al. |
| 2009/0220916 A1 | 9/2009 | Fisker et al. |
| 2009/0220917 A1 | 9/2009 | Jensen |
| 2009/0239197 A1 | 9/2009 | Brajnovic |
| 2009/0239200 A1 | 9/2009 | Brajnovic et al. |
| 2009/0253097 A1 | 10/2009 | Brajnovic |
| 2009/0263764 A1 | 10/2009 | Berckmans, III et al. |
| 2009/0287332 A1 | 11/2009 | Adusumilli et al. |
| 2009/0298009 A1 | 12/2009 | Brajnovic |
| 2009/0298017 A1 | 12/2009 | Boerjes et al. |
| 2009/0317763 A1 | 12/2009 | Brajnovic |
| 2009/0325122 A1 | 12/2009 | Brajnovic et al. |
| 2010/0009314 A1 | 1/2010 | Tardieu et al. |

(56) References Cited

U.S. PATENT DOCUMENTS

| | | |
|---|---|---|
| 2010/0028827 A1 | 2/2010 | Andersson et al. |
| 2010/0038807 A1 | 2/2010 | Brodkin et al. |
| 2010/0075275 A1 | 3/2010 | Brajnovic |
| 2010/0092904 A1 | 4/2010 | Esposti et al. |
| 2010/0105008 A1 | 4/2010 | Powell et al. |
| 2010/0151420 A1 | 6/2010 | Ranck |
| 2010/0151423 A1 | 6/2010 | Ranck et al. |
| 2010/0173260 A1 | 7/2010 | Sogo et al. |
| 2010/0209877 A1 | 8/2010 | Hogan et al. |
| 2010/0280798 A1 | 11/2010 | Pattijn et al. |
| 2011/0008751 A1 | 1/2011 | Pettersson |
| 2011/0060558 A1 | 3/2011 | Pettersson |
| 2011/0129792 A1 | 6/2011 | Berckmans, III et al. |
| 2011/0183289 A1 | 7/2011 | Powell et al. |
| 2011/0191081 A1 | 8/2011 | Malfliet et al. |
| 2011/0244426 A1 | 10/2011 | Amber et al. |
| 2011/0269104 A1 | 11/2011 | Berckmans, III et al. |
| 2011/0275032 A1 | 11/2011 | Tardieu et al. |
| 2011/0306008 A1 | 12/2011 | Suttin et al. |
| 2011/0306009 A1 | 12/2011 | Suttin et al. |
| 2011/0306014 A1 | 12/2011 | Conte et al. |
| 2012/0010740 A1 | 1/2012 | Swaelens et al. |
| 2012/0135370 A1 | 5/2012 | Ranck et al. |
| 2012/0164593 A1 | 6/2012 | Bavar |
| 2012/0164893 A1 | 6/2012 | Misuzuka et al. |
| 2012/0214130 A1 | 8/2012 | Krivoruk |
| 2012/0330315 A1 | 12/2012 | Ranck et al. |
| 2013/0296813 A2* | 11/2013 | Park .............................. 604/318 |

FOREIGN PATENT DOCUMENTS

| | | |
|---|---|---|
| WO | WO 99/32045 | 7/1999 |
| WO | WO 00/08415 | 2/2000 |
| WO | WO 01/58379 | 8/2001 |
| WO | WO 02/053055 | 7/2002 |
| WO | WO 03/024352 | 3/2003 |
| WO | WO 2004/030565 | 4/2004 |
| WO | WO 2004/075771 | 9/2004 |
| WO | WO 2004/087000 | 10/2004 |
| WO | WO 2004/098435 | 11/2004 |
| WO | WO 2006/014130 | 2/2006 |
| WO | WO 2006/062459 | 6/2006 |
| WO | WO 2006/082198 | 8/2006 |
| WO | WO 2007/005490 | 1/2007 |
| WO | WO 2007/033157 | 3/2007 |
| WO | WO 2007/104842 | 9/2007 |
| WO | WO 2007/129955 | 11/2007 |
| WO | WO 2008/057955 | 5/2008 |
| WO | WO2008/083857 | 7/2008 |
| WO | WO2009/146164 | 12/2009 |

OTHER PUBLICATIONS

Francois Goulette, "A New Method and a Clinical case for Computer Assisted Dental Implantology." Retrieved from Summer European university in surgical Robotics URL:www.lirmm.fr/manifs/UEE/docs/students/goulette.pdf, Sep. 6, 2003 (7 pages).

International Search Report for International Application No. PCT/US2009/034463, filed Feb. 19, 2009, dated Apr. 30, 2009 (2 pages).

Jakob Brief, "Accuracy of image-guided implantology." Retrieved from Google, <URL:sitemaker.umich.edu/sarmentlab/files/robodent_vs_denx_coir_05.pdf, Aug. 20, 2004 (7 pages).

Machine Design: "Robots are ready for medical manufacturing." Retrieved from MachineDesign.Com, <URL: http://machinedesign.com/article/robots-are-ready-for-medical-manufacturing-0712>, Jul. 12, 2007 (7 pages).

MedNEWS: "'Surgical Glue' May Help to Eliminate Suturing for Implants." Retrieved from MediNEWS.Direct, URL:http://www.medinewsdircet.com/?p=377, Dec. 21, 2007 (1 page).

Written Opinion of International Application No. PCT/US2009/034463, filed Feb. 19, 2009, dated Apr. 30, 2009 (6 pages).

International Search Report for International Application No. PCT/US2012/038097, filed May 16, 2012, dated Sep. 7, 2012 (2 pages).

International Written Opinion for International Application No. PCT/US2012/038097, filed May 16, 2012, dated Sep. 7, 2012 (9 pages).

* cited by examiner

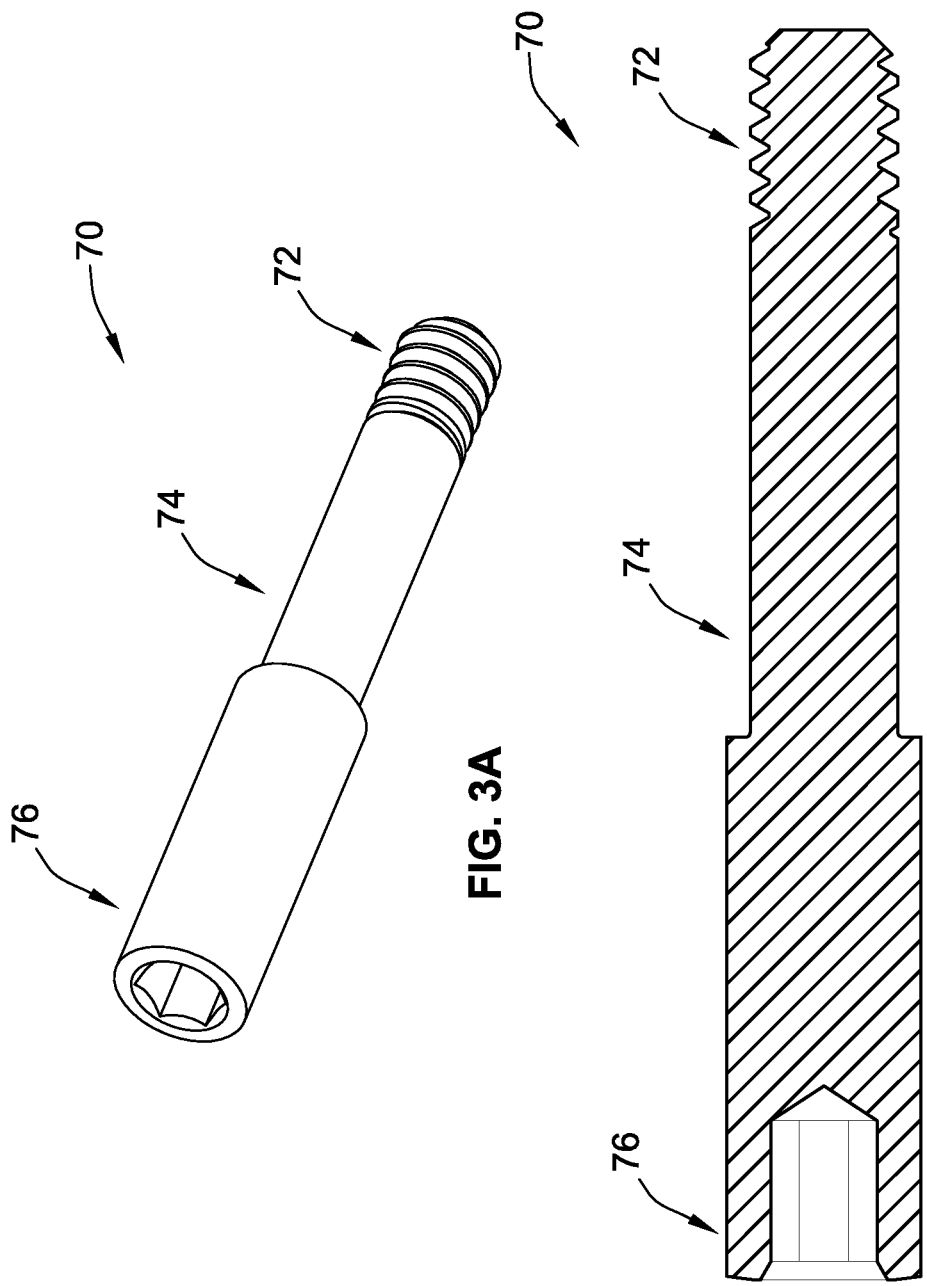

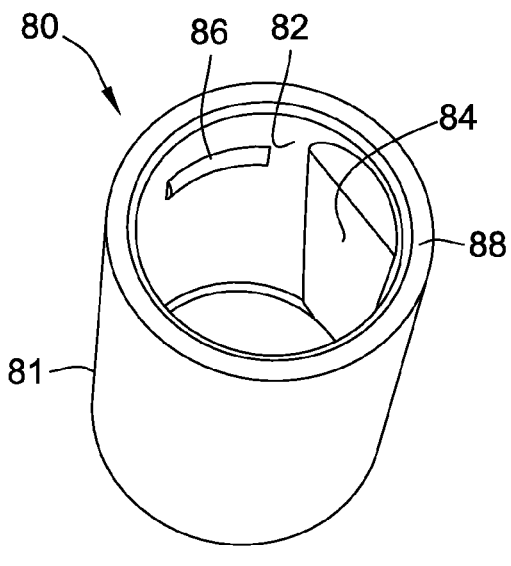
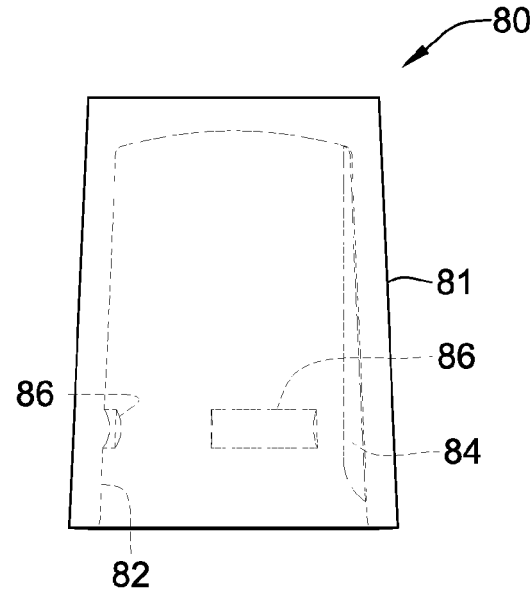
FIG. 4A    FIG. 4B
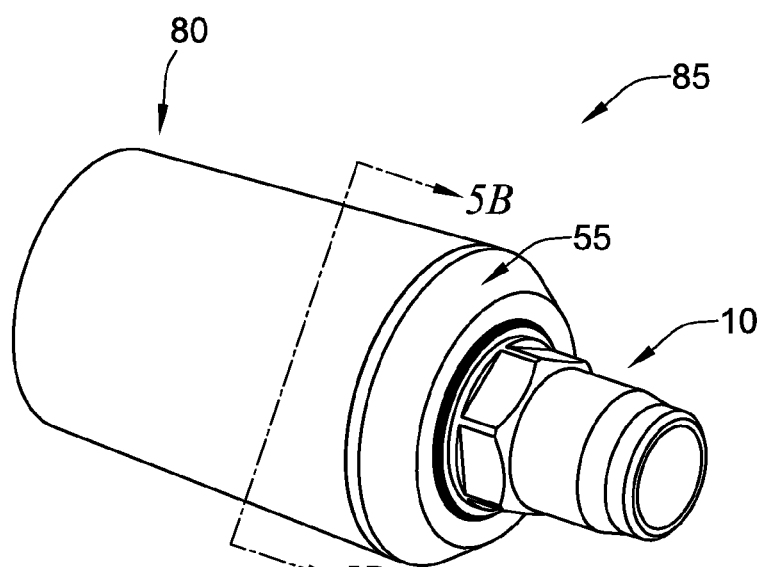
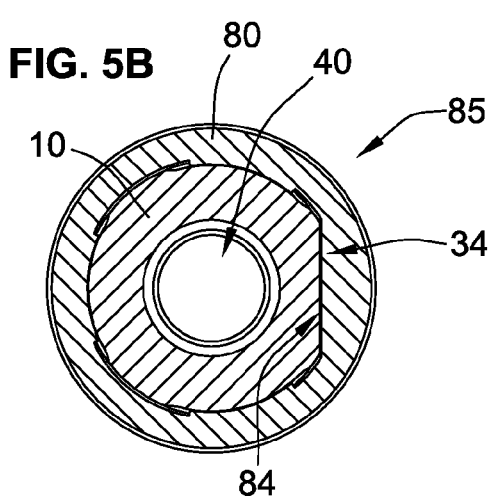
FIG. 5A
FIG. 5B

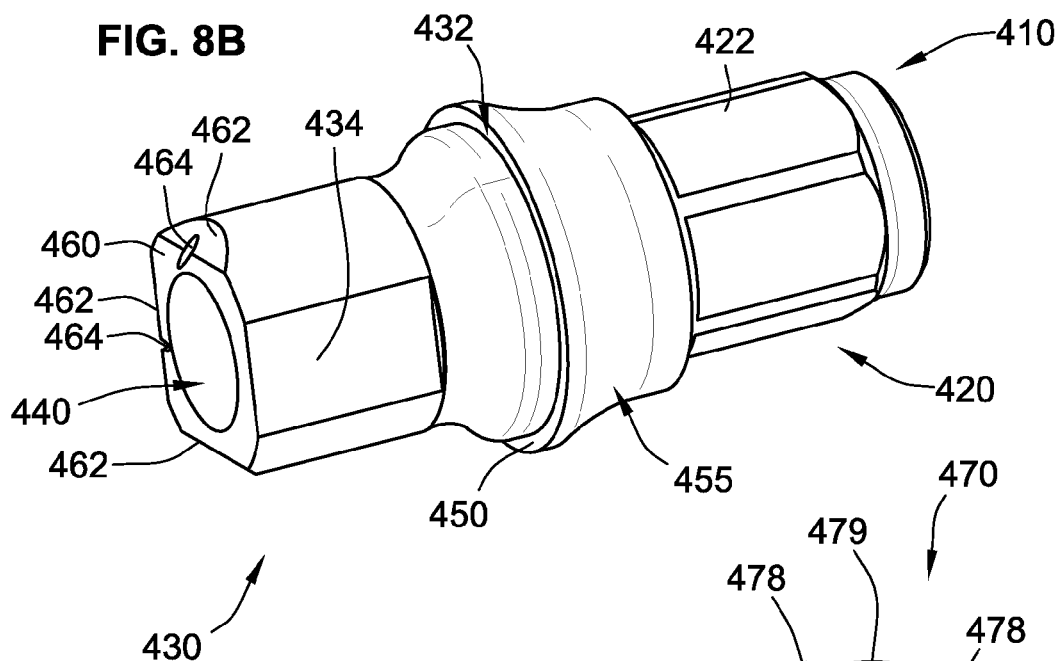
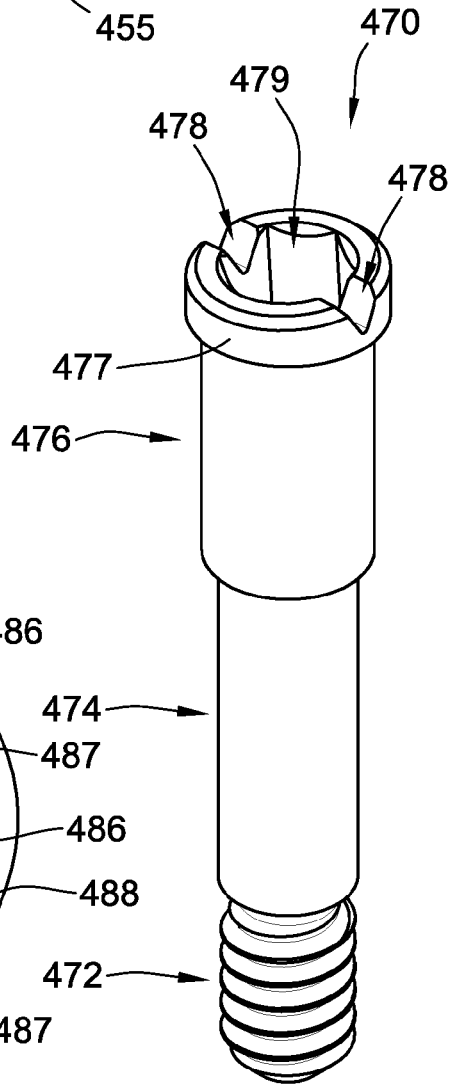
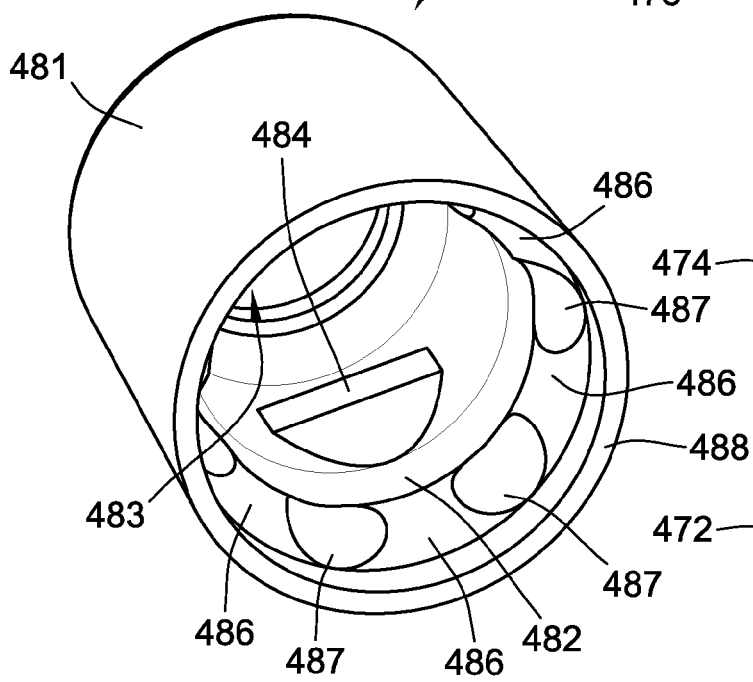
FIG. 8B
FIG. 8C
FIG. 8D

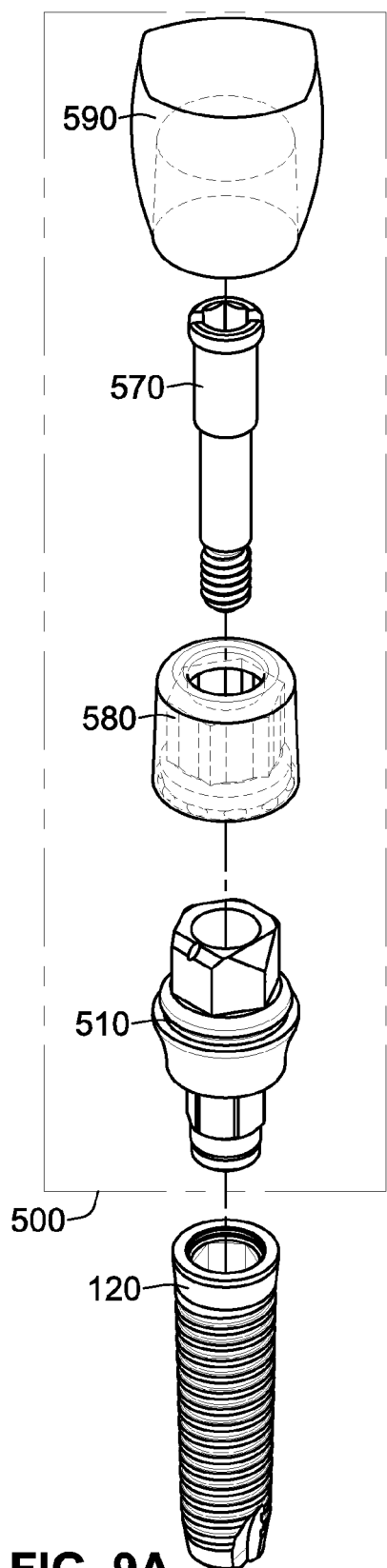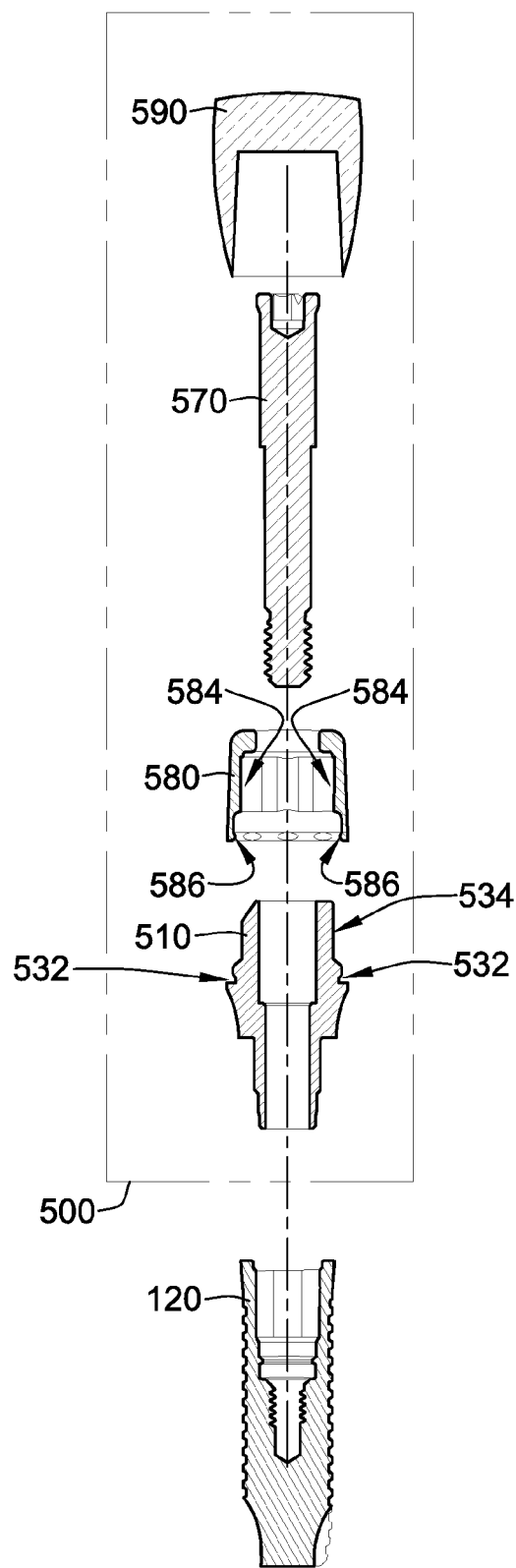
FIG. 9A
FIG. 9D

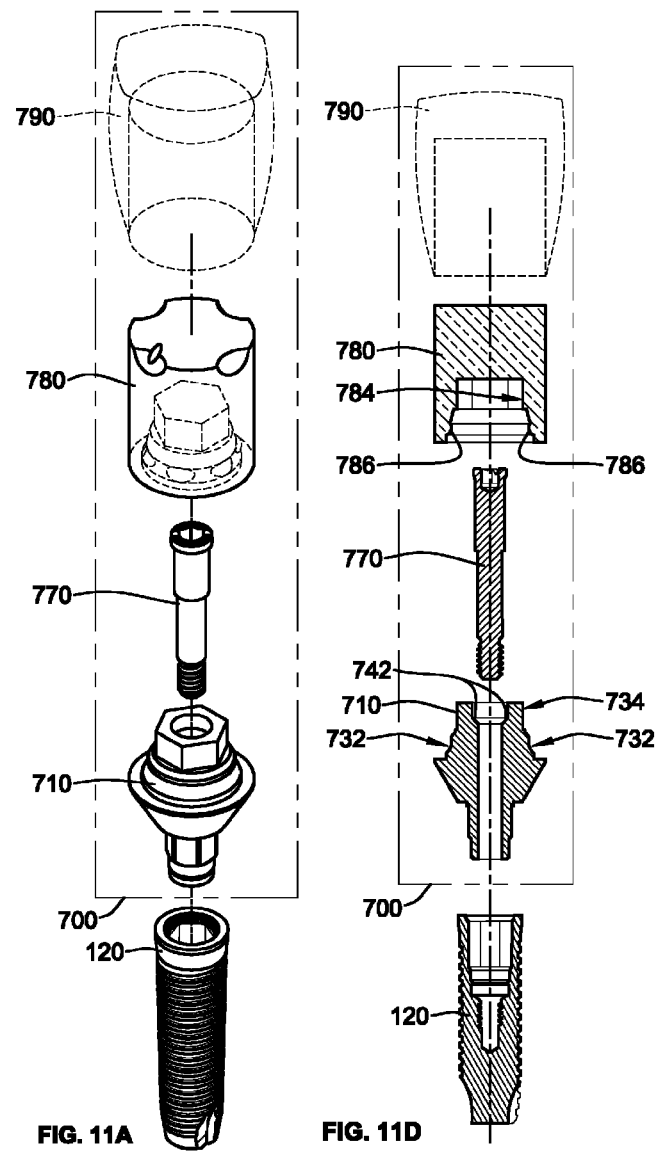

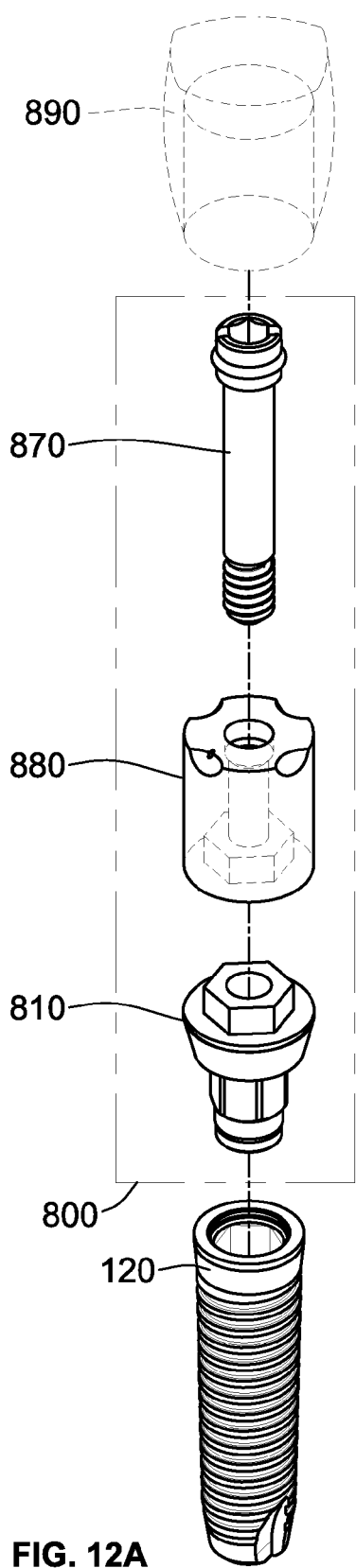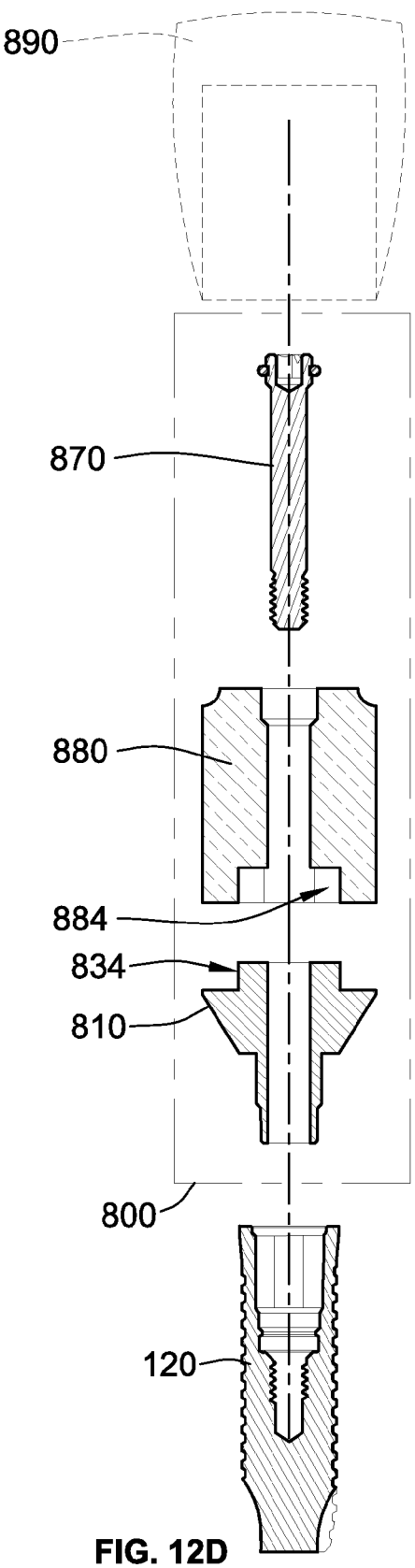
FIG. 12A
FIG. 12D

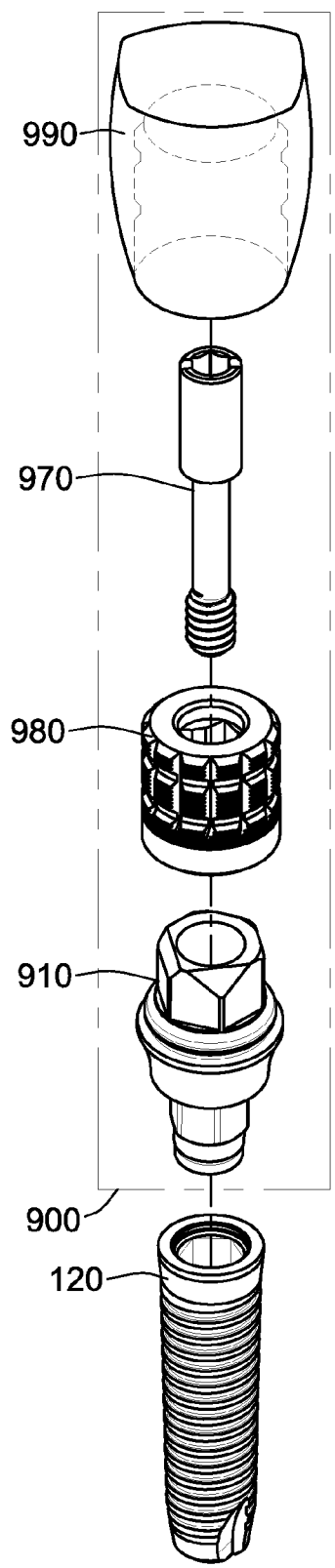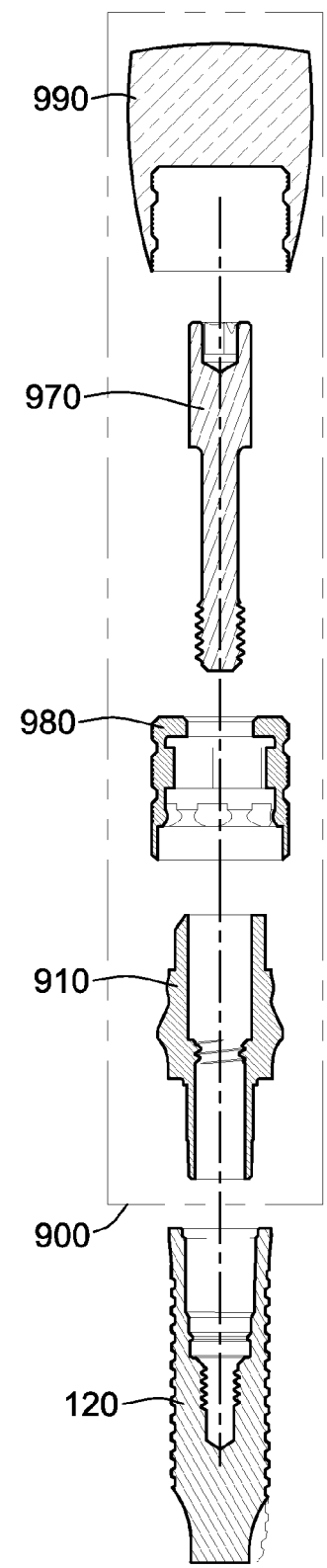
FIG. 13A  FIG. 13F

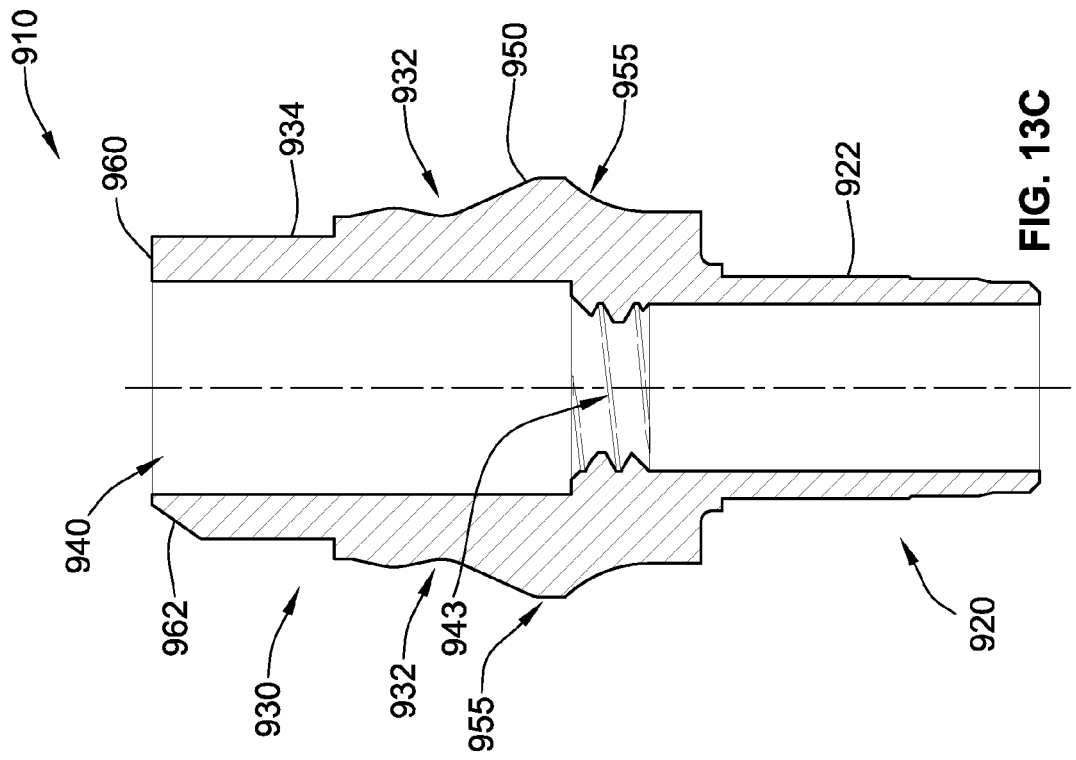
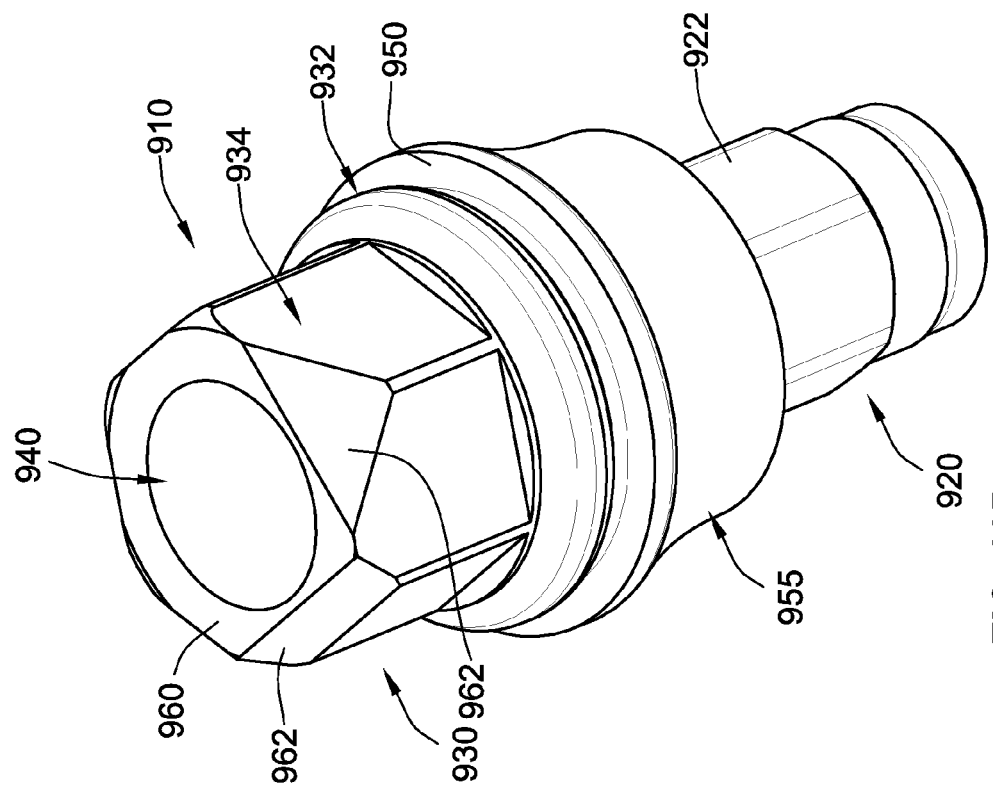

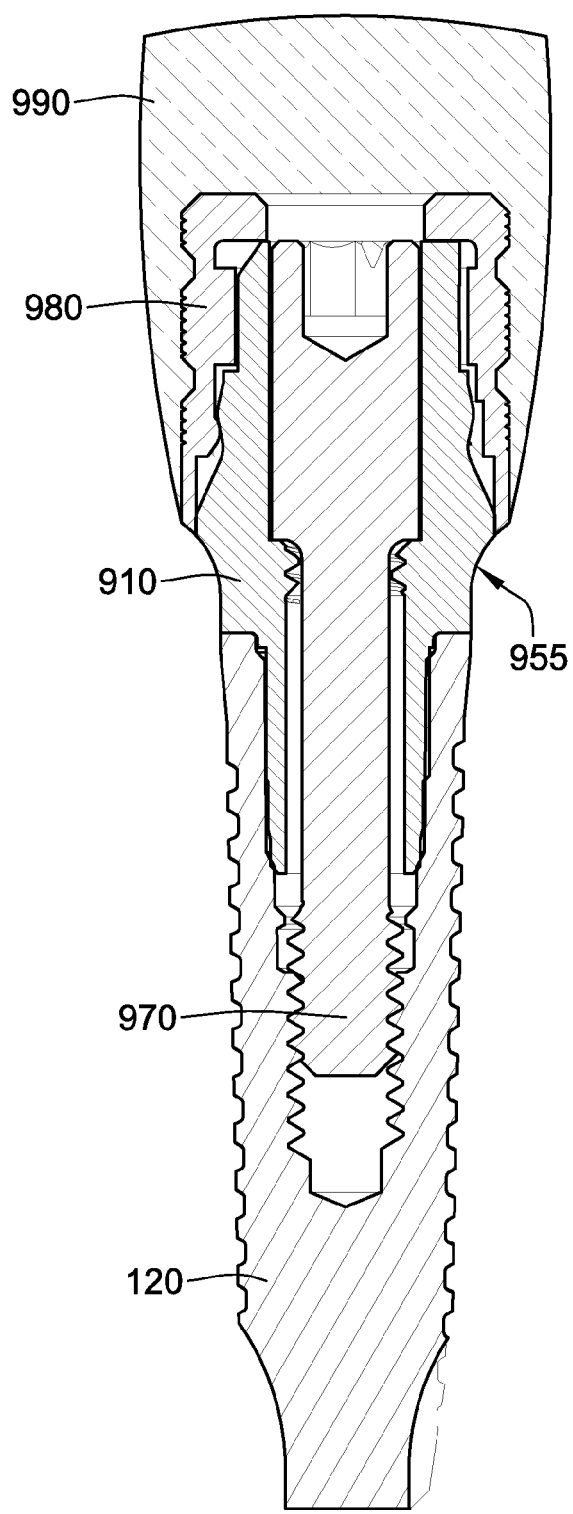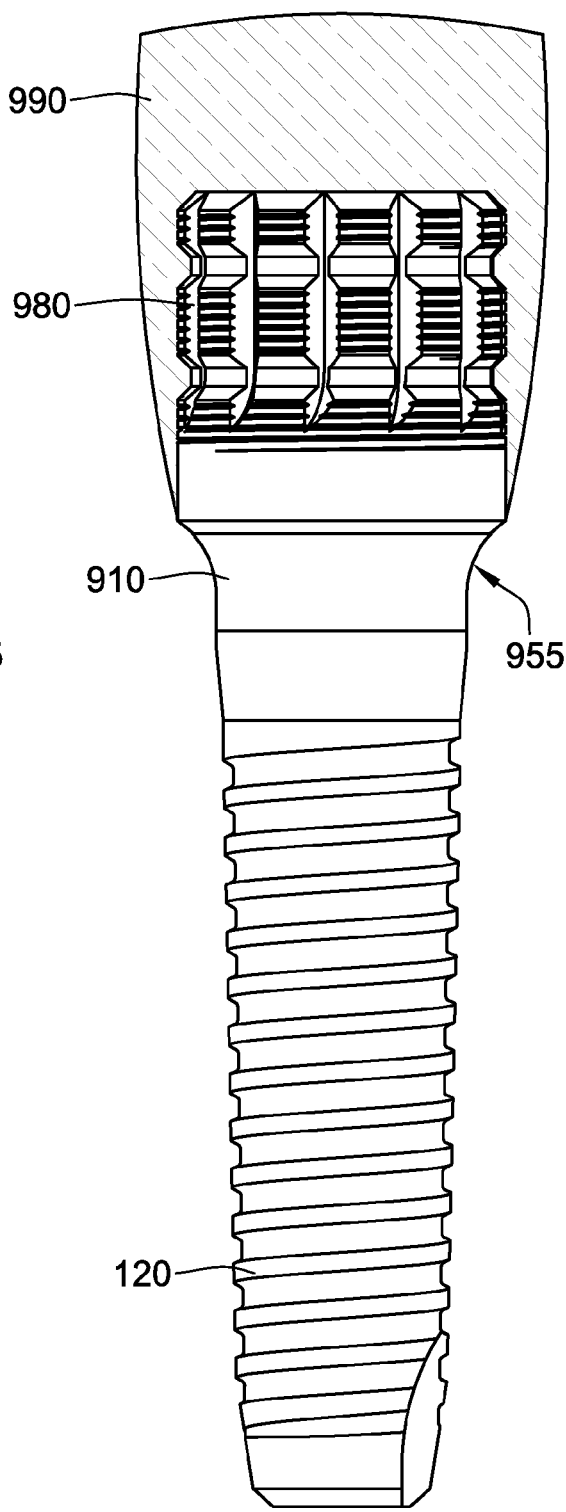
FIG. 13G            FIG. 13H

TEMPORARY ABUTMENT WITH COMBINATION OF SCANNING FEATURES AND PROVISIONALIZATION FEATURES

CROSS-REFERENCE TO RELATED APPLICATION

This application claims the benefit of U.S. Provisional Application No. 61/486,630, filed May 16, 2011, which is hereby incorporated by reference herein in its entirety. This application is related to copending U.S. Ser. No. 13/473,219, filed on May 16, 2012, entitled "Temporary Abutment with Combination of Scanning Features and Provisionalization Features".

FIELD OF THE INVENTION

The present invention relates generally to a temporary abutment in a dental implant system. More particularly, the present invention relates to a temporary abutment having scanning features and provisionalization features.

BACKGROUND OF THE INVENTION

The dental restoration of a partially or wholly edentulous patient with artificial dentition is typically done in two stages. In the first stage, an incision is made through the gingiva to expose the underlying bone. An artificial tooth root, in the form of a dental implant, is placed in the jawbone for osseointegration. The dental implant generally includes a threaded bore to receive a retaining screw for holding mating components thereon. During the first stage, the gum tissue overlying the implant is sutured and heals as the osseointegration process continues.

Once the osseointegration process is complete, the second stage is initiated. Here, the gingival tissue is re-opened to expose an end of the dental implant. A healing component or healing abutment is fastened to the exposed end of the dental implant to allow the gingival tissue to heal therearound. It should be noted that the healing abutment can be placed on the dental implant immediately after the implant has been installed and before osseointegration. In recent years, for some situations, the osseointegration step and gingival healing steps have been combined into a one-step process.

Prior healing abutments were generally round in profile, but the artificial teeth or prostheses that eventually replaced the healing abutments were not. Thus, the gingival tissue would heal around the healing abutments creating an emergence profile that approximated the size and contour of the healing abutment and not the size and contour of the prosthesis that was eventually attached to the implant. The resulting discrepancies between the emergence profile of the patient's gingiva and the installed prosthesis could sometimes require additional visits with the dentist or clinician to finalize the installation process and/or compromise the aesthetic outcome of the installed prosthesis. The present disclosure is directed to solving this and other problems with the prior healing abutments. There is also a need to resolve problems related to temporization of a prosthesis, as often times, prior to placing a permanent prosthesis, it is desirable to place a temporary prosthesis at the same location on the implant.

In more recent years, scanning technologies have been used to aid in the development of permanent prostheses. The present disclosure is also directed at solving problems with tying in the scanning technologies with the temporization of prostheses.

SUMMARY OF THE INVENTION

An abutment assembly for attachment to a dental implant includes a temporary abutment and a temporary abutment cap. The temporary abutment has a lower region and an upper region. The lower region includes an anti-rotational feature for non-rotationally mating with the dental implant. The upper region includes a first anti-rotational structure and at least one retention groove. A top surface of the temporary abutment includes one or more informational markers that provide information concerning the dental implant. The temporary abutment cap is configured to be coupled to the upper region of the temporary abutment. The temporary abutment cap has at least one projection configured to mate with the at least one retention groove of the temporary abutment. The temporary abutment cap has a second anti-rotational structure that is configured to slidably engage the first anti-rotational structure of the temporary abutment. An outer surface of the temporary abutment cap is configured to be coupled with a temporary prosthesis such that the temporary prosthesis and the temporary abutment cap are removable from the temporary abutment permitting access to the informational markers.

A temporary prosthesis assembly for attachment to a dental implant includes a temporary abutment, a temporary abutment cap, and a temporary prosthesis. The temporary abutment includes an anti-rotational feature for non-rotationally mating with the dental implant. The temporary abutment includes one or more informational markers. The temporary abutment cap is configured to be removably coupled to the temporary abutment so as to cover the informational markers. The temporary prosthesis is configured to be coupled the temporary abutment cap. The combination of the temporary prosthesis and the temporary abutment cap is removably coupled to the temporary abutment.

An abutment for attachment to a dental implant includes a lower region, an upper region, and an internal bore. The lower region includes an anti-rotational feature for non-rotationally mating with the dental implant. The upper region includes an anti-rotational structure and at least one axial retention structure. The anti-rotational structure and the at least one axial retention structure is for engagement with a tooth-shaped prosthetic component. The upper region includes one or more informational markers for providing information concerning the dental implant that are revealed after the tooth-shaped prosthetic component has been removed from the abutment. The internal bore is configured to receive a fastening device for coupling the abutment to the dental implant.

A temporary abutment system for attachment to different types of dental implants includes a plurality of temporary abutments and a temporary abutment cap. Each of the temporary abutments includes a lower region and an upper region. The lower region includes an anti-rotational feature for non-rotationally mating with one of the dental implants. The upper region includes a first anti-rotational structure and a first axial retention structure. The upper region further includes informational markers for providing information concerning (i) the type of dental implant to which the temporary abutment is to be attached and (ii) positional or dimensional information related to the attached dental implant. The temporary abutment cap has a second anti-rotational structure for mating with the first anti-rotational structure and a second axial retention structure for mating with the first axial retention structure. The temporary abutment cap is configured to be mated with any of the temporary abutments such that the temporary abutment cap covers the informational markers.

A method of creating a patient-specific abutment to be coupled to an implant installed in a mouth of a patient includes non-rotationally attaching a temporary abutment to the implant. The temporary abutment includes at least one informational marker indicative of one or more characteristics of the implant. A temporary prosthetic assembly is non-rotationally attached to the temporary abutment such that the temporary prosthetic assembly is removable therefrom. After a sufficient period of time during which gingival tissue surrounding the temporary prosthetic assembly has healed, the temporary prosthetic assembly is removed from the temporary abutment. After the removing, at least a portion of the mouth is scanned including the temporary abutment to generate scan data. From the scan data, emergence profile information for the gingival tissue adjacent to the temporary abutment is obtained and informational marker information from the temporary abutment is obtained. Based on the emergence profile information for the gingival tissue and the informational marker information, a three-dimensional model of at least a portion of the mouth is created. A patient-specific abutment is designed from the three-dimensional model.

A method of creating a patient-specific abutment to be coupled to an implant installed in a mouth of a patient includes attaching a non-round temporary prosthesis to the implant. The temporary prosthesis includes a temporary abutment that has at least one informational marker indicative of one or more characteristics of the implant. After gingival tissue surrounding the temporary prosthesis has healed in a non-round fashion, the temporary prosthesis is disassembled to expose the at least one informational marker on the temporary abutment without removing the temporary abutment from the implant. A scanning process is used to scan the at least one informational marker to obtain data including data associated with information about the implant. A patient-specific abutment is created from the data obtained via the scanning process.

A method of creating a patient-specific abutment to be coupled to an implant installed in a mouth of a patient includes non-rotationally attaching a temporary abutment to the dental implant. The temporary abutment includes at least one informational marker indicative of one or more characteristics of the implant. At least a portion of the mouth including the temporary abutment is scanned to generate a first set of scan data. After a shape for a temporary prosthesis has been selected, a temporary prosthesis is scanned outside of the mouth to generate a second set of scan data. The temporary prosthesis is attached to the temporary abutment such that the temporary prosthesis is removable therefrom. The first and the second sets of scan data is analyzed to obtain informational marker information and to obtain predicted anatomically shaped emergence gingiva profile information. A three-dimensional model of at least a portion of the mouth from the first and the second sets of scan data is created. A patient-specific abutment is designed from the three-dimensional model.

A method of creating a patient-specific abutment to be coupled to an implant installed in a mouth of a patient includes non-rotationally attaching a temporary abutment to the implant. The temporary abutment includes at least one informational marker indicative of one or more characteristics of the implant. A temporary abutment cap is snap-fitted on the temporary abutment such that the temporary abutment cap is removable therefrom and at least partially obscures the at least one informational marker of the temporary abutment. A temporary prosthesis is attached to the temporary abutment cap. After a sufficient period of time during which gingival tissue surrounding the temporary prosthesis, the temporary abutment cap, and the temporary abutment has healed, the temporary prosthesis and the temporary abutment cap are removed from the temporary abutment. After the removing, at least a portion of the mouth is scanned including the temporary abutment to generate scan data. From the scan data, emergence profile information for the gingival tissue adjacent to the temporary abutment is obtained and informational marker information from the temporary abutment is obtained. Based on the emergence profile information for the gingival tissue and the informational marker information, a three-dimensional model of at least a portion of the mouth is created. A patient-specific abutment is designed from the three-dimensional model.

BRIEF DESCRIPTION OF THE DRAWINGS

The foregoing and other advantages of the invention will become apparent upon reading the following detailed description and upon reference to the drawings.

FIG. 3A is a perspective view of a fastening device used for holding the temporary abutments of the present disclosure on a dental implant;

FIG. 3B is a side cross-sectional view of the fastening device shown in FIG. 3A;

FIG. 4A is a perspective view of a temporary abutment cap;

FIG. 4B is a side view of the temporary abutment cap shown in FIG. 4A;

FIG. 5A is a perspective view of an abutment assembly;

FIG. 5B is a top cross-sectional view of the abutment assembly as shown in FIG. 5A;

FIG. 8B is a perspective view of a temporary abutment of the prosthesis assembly of FIG. 8A.

FIG. 8C is a perspective view of a screw of the prosthesis assembly of FIG. 8A;

FIG. 8D is a perspective view of a temporary abutment cap of the prosthesis assembly of FIG. 8A;

FIG. 9A is an exploded perspective view of a prosthesis assembly and an implant according to another alternative embodiment of the invention;

FIG. 9D is an exploded cross-sectional view of the prosthesis assembly and the implant of FIG. 9A;

FIG. 11A is an exploded perspective view of a prosthesis assembly and an implant according to yet another alternative embodiment of the invention;

FIG. 11D is an exploded cross-sectional view of the prosthesis assembly and the implant of FIG. 11A;

FIG. 12A is an exploded perspective view of a prosthesis assembly and an implant according to yet another alternative embodiment of the invention;

FIG. 12D is an exploded cross-sectional view of the prosthesis assembly and the implant of FIG. 12A;

FIG. 13A is an exploded perspective view of a prosthesis assembly and an implant according to yet another alternative embodiment of the invention;

FIG. 13B is a perspective view of a temporary abutment of the prosthesis assembly of FIG. 13A;

FIG. 13C is a cross-sectional view of the temporary abutment of FIG. 13B;

FIG. 13F is an exploded cross-sectional view of the prosthesis assembly and the implant of FIG. 13A;

FIG. 13G is an assembled cross-sectional view of the prosthesis assembly and the implant of FIG. 13A;

FIG. 13H is an assembled partial cross-sectional view of the prosthesis assembly and the implant of FIG. 13A;

Figure 1A:
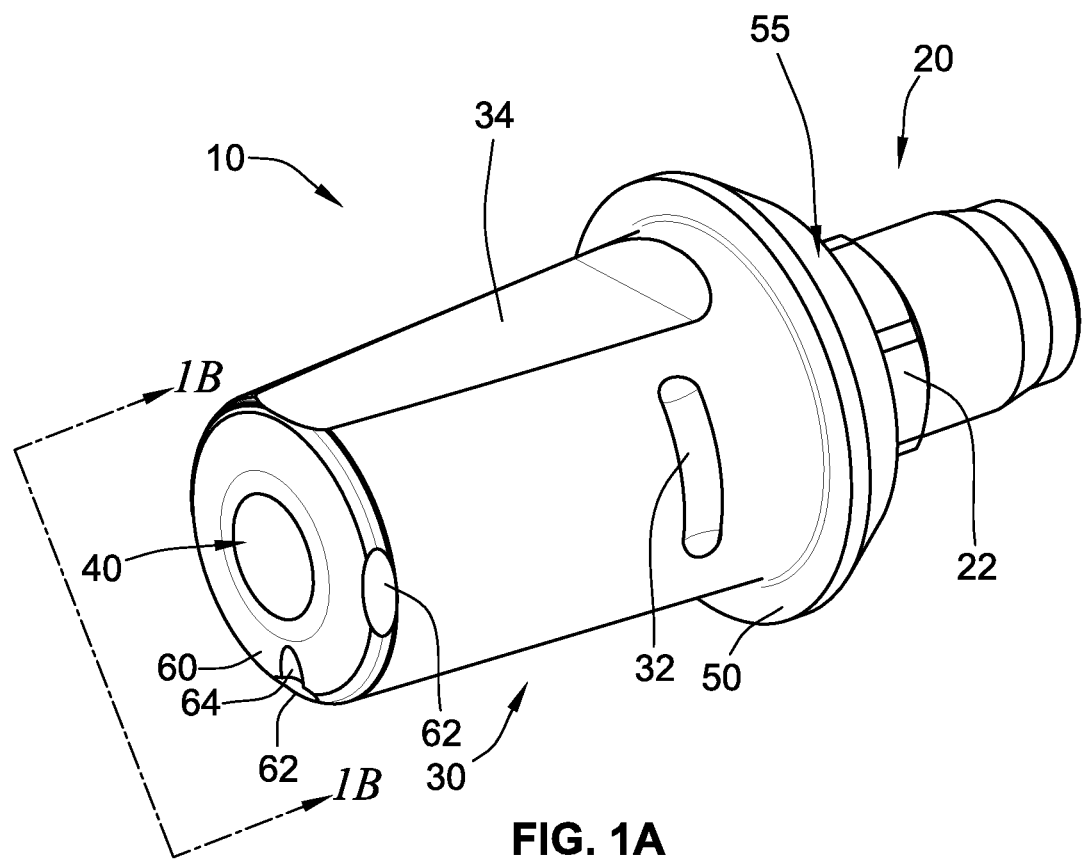
FIG. 1A is a perspective view of a temporary abutment.

While the present disclosure is susceptible to various modifications and alternative forms, specific embodiments have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DESCRIPTION OF ILLUSTRATIVE EMBODIMENTS

Figure 1B:
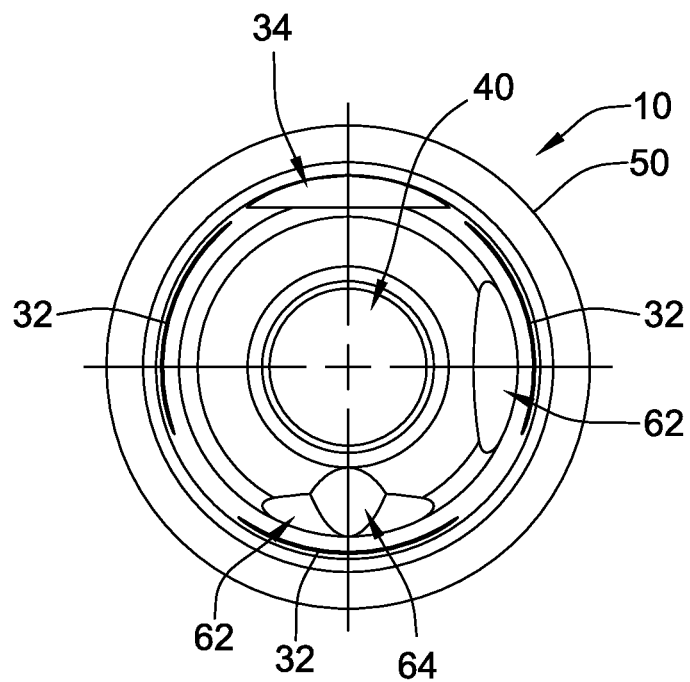
FIG. 1B is a top view of the temporary abutment shown in FIG. 1A.

Referring to FIGS. 1A and 1B, a temporary abutment 10 of the present disclosure (like other temporary abutments of the present disclosure) may be used for at least four purposes, which will be explained in more detail below. First, the temporary abutment 10 may serve as a gingival healing abutment as its exterior surface is contoured to aid in the healing of a patient's gingival tissue. Second, the temporary abutment 10 may serve as a temporary prosthesis (i.e., it provides a convenient mount for removably attaching an acrylic portion having an anatomical tooth shape). Third, the temporary abutment 10 serves as a scanning member to permit a clinician to use one or more scanning techniques to obtain necessary information about the underlying implant's location and orientation for use in developing permanent prosthetic components. And fourth, the temporary abutment 10 may serve as a permanent abutment providing a convenient mount for a permanent prosthesis having an anatomical tooth shape.

The temporary abutment 10 has a subgingival region 20 and a supragingival region 30, which are separated by a flange 50. An outer surface 55 (best shown in FIG. 5A) of the flange 50 is positioned to engage and aid in forming a patient's gingival tissue during the healing process. The subgingival region 20 includes an anti-rotational feature 22 (e.g., a hexagonal section) for mating with a corresponding anti-rotational feature of an implant (e.g., implant 120 in FIG. 6A). The anti-rotational feature 22 of the temporary abutment 10 can be any type of boss (e.g., polygonal boss, star boss, clover boss, etc.) or socket (e.g., polygonal socket, star socket, clover socket, etc.) such that it corresponds with an anti-rotational feature of the underlying implant to prevent relative rotation of the temporary abutment 10 with respect to the implant 120. It is contemplated that the temporary abutment 10 (and the other temporary abutments of the present disclosure) can be fashioned from gold, titanium, plastic, ceramic, or other similar metals or composites.

The supragingival region 30 includes one or more retention grooves or structures 32 and an anti-rotational structure 34 (e.g., a flat wall or surface). The retention grooves 32 are configured to mate in a snap-type axial holding engagement with corresponding male circumferential features or structures 86 (shown in FIGS. 4A and 4B) of a temporary abutment cap 80 (shown in FIGS. 4A and 4B). The one or more retention grooves 32 are configured to mate with the male circumferential features 86 with a retention force between about one and about ten pounds of force. That is, it takes between about one and about ten pounds of force to remove the temporary abutment cap 80 from its snap-fit type engagement with the temporary abutment 10. Alternatively, the supragingival region 30 of the temporary abutment 10 can include male circumferential features that are configured to mate in a snap-type axial holding engagement with corresponding retention grooves on an inside surface of the temporary abutment cap 80 (not shown).

The anti-rotational structure 34 is configured to mate in a slidable engagement with a corresponding anti-rotational structure 84 (shown in FIGS. 4A and 4B) to prevent relative rotation of the temporary abutment cap 80 and the temporary abutment 10. In the illustrated implementation, the anti-rotational structure 34 generally extends from a top surface 60 of the temporary abutment 10 to the flange 50. While the anti-rotational structure 34 is shown as a flat wall on the supragingival region 30, the anti-rotational structure 34 can be one of a variety of known anti-rotational structures, such as, for example, one or more grooves, slots, projections, or any combination thereof. Examples of anti-rotational structures for dental posts are shown in U.S. Pat. Nos. 6,120,293, 6,159,010, and 8,002,547, each of which is commonly owned by the assignee of the present application and is hereby incorporated by reference herein in its entirety. Regardless of the type of anti-rotational structure 34 chosen for the supragingival region 30 of the temporary abutment 10, the temporary abutment cap 80 has a correspondingly shaped structural surface (e.g., anti-rotational structure 84) for engaging the anti-rotational structure 34 so as to prevent relative rotation between the two components.

The temporary abutment 10 is generally cylindrical in shape with an internal bore 40 for receiving a screw 70 (shown in FIGS. 3A and 3B) to removably couple the temporary abutment 10 to the implant 120. The top surface 60, which is best shown in FIG. 1B, includes two informational marker locations 62. The informational marker locations 62 are positioned circumferentially around the top surface 60 of the temporary abutment 10. While the temporary abutment 10 is shown with informational marker locations 62 only at locations of 3 o'clock, and 6 o'clock with respect to the anti-rotational structure 34 being at 12 o'clock, it is contemplated that additional informational marker locations (not shown) can be placed at 9 o'clock, 12 o'clock, and/or at any positions therebetween.

Each of the informational marker locations 62 is configured to include one or more informational markers 64. The informational marker 64 is shown as one notch; however, the present disclosure contemplates that the informational markers 64—for all of the embodiments disclosed herein—can be positive informational markers, negative informational markers, raised projections/pimples, recesses or dimples, notches, lines, etching, alphanumeric characters, etc. It is further contemplated that the cross-section of the informational markers 64 can be rectangular, triangular, or various other shapes. Further, the informational marker locations 62 themselves can act as informational markers and provide and/or indicate information.

The informational markers 64 are indicative of one or more characteristics of the temporary abutment 10 itself and/or of the underlying implant 120 (shown in FIG. 6A) to which the temporary abutment 10 is attached. For example, one or more of the informational markers 64 can be geometrically aligned with a flat of the non-rotational feature 22 of the temporary abutment 10 and/or a flat on the underlying implant to indicate the rotational orientation of the non-rotational features of the temporary abutment 10 and/or of the underlying implant. It is also contemplated that one or more of the informational markers 64 may correspond to the height of the temporary abutment 10 and, hence, a height or vertical position (i.e., z-axis location) of a table or seating surface of the underlying implant. For another example, the informational markers 64 can be indicative of the x-y location of the table or seating surface of the underlying implant. For another example, the informational markers 64 can be indicative of the angle that the underlying implant rests with respect to vertical within the patient's jawbone (e.g., pitch and yaw). For another example, the informational markers 64 can be indicative of the size and/or shape of the temporary abutment 10 and/or the underlying implant. For another example, the informational markers 64 can be indicative of the manufacturer of the underlying implant.

The informational markers 64 can be part of a binary marking system that identifies unique characteristics of the temporary abutment 10 and/or the underlying implant 120. As is well known, a binary-coded system exists as an array of digits, where the digits are either "1" or "0" that represent two states, respectively, ON and OFF. For each informational marking location 62, the presence of an informational marker 64 ("ON") is a 1 and the absence of an informational marker 64 ("OFF") is a 0. By grouping sets of 1's and 0's together starting from a known starting location (e.g., 3 o'clock or the first location in the clockwise direction from the anti-rotational structure 34), information about each temporary abutment 10 is known. For the temporary abutment 10, the two informational marker locations 62 can provide four different combinations. Additional details on informational markers and the characteristics of the underlying implant and/or the abutment that are identified by the informational markers (e.g., informational markers 64) can be found in U.S. Pat. No. 7,988,449, which is hereby incorporated by reference herein in its entirety.

Figure 2A:
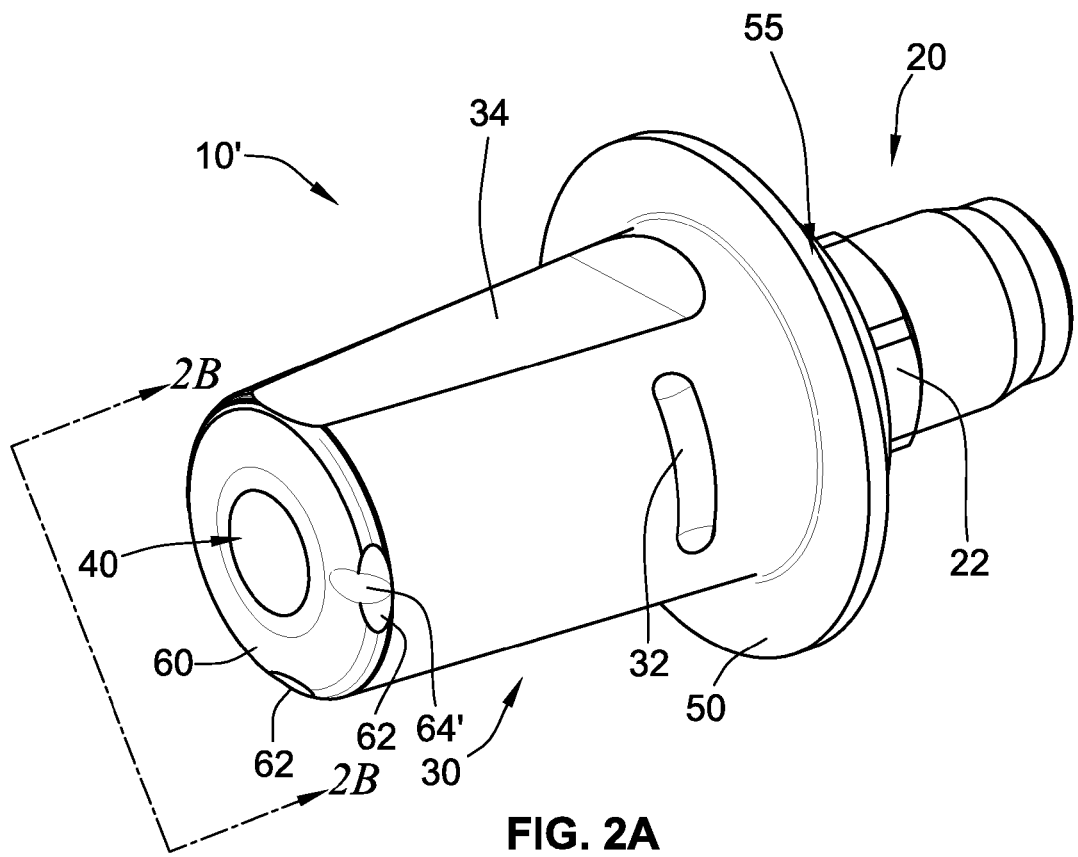
FIG. 2A is a perspective view of a second temporary abutment.
Figure 2B:
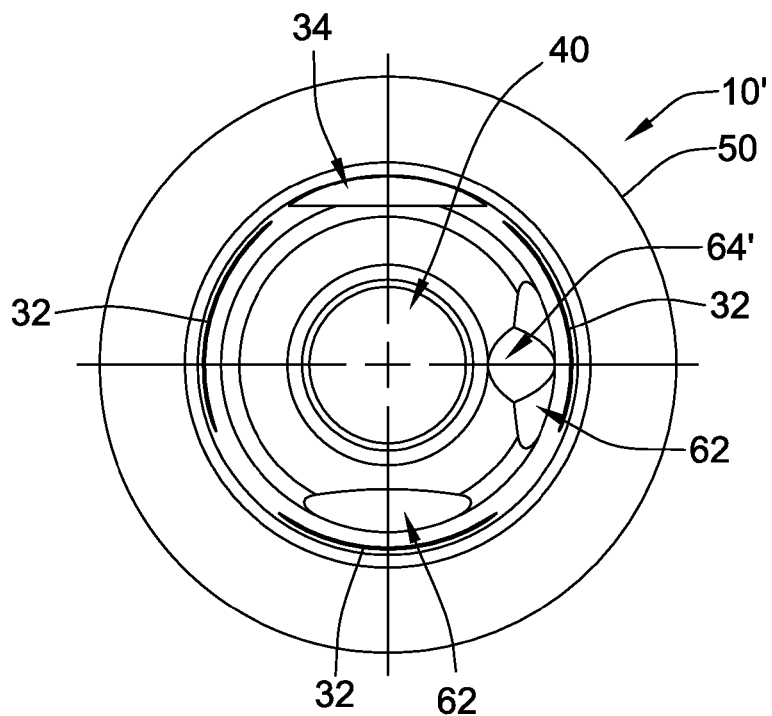
FIG. 2B is a top view of the second temporary abutment shown in FIG. 2A.

Referring to FIGS. 2A and 2B, a temporary abutment 10' is shown. The temporary abutment 10' includes all of the same features as the temporary abutment 10, where like reference numbers are used for like components; however, the temporary abutment 10' is a different size of temporary abutment. The difference is noticeable by reference to the orientation or positioning of the informational marker 64' and the informational marker locations 62' on the top surface 60 of the temporary abutment 10'. A quick comparison of the top surface 60 of the temporary abutment 10 with the top surface 60 of the temporary abutment 10' reveals that the informational marker 64' is in a different orientation, which indicates that the temporary abutment 10' has at least one characteristic that is different from the temporary abutment 10. For example, the temporary abutment 10' has a larger or wider subgingival region 20 and flange 50 than the subgingival region 20 and flange 50 of the temporary abutment 10. For another example, the outer surface 55 of the flange 50 of the temporary abutment 10' can have a different curve and/or profile than the outer surface 55 of the flange 50 of the temporary abutment 10.

Referring to FIGS. 3A and 3B, a fastening device such as the screw or attaching bolt 70 includes a threaded portion 72, a shaft portion 74, and a head portion 76 including a socket. The head portion 76 on the exposed surface of a head of the screw 70 is shaped to accept a wrench (not shown) for threadably engaging the screw 70 into a threaded bore of an implant 120 (shown in FIG. 6A). It is contemplated that each of the temporary abutments described herein and shown in the figures can be secured to an implant by means of the screw 70, or by means of a similar screw, as is known in the art. It is further contemplated that one or more washers (e.g., locking washer) and/or O-rings (e.g., sealing O-ring) can be placed on the screw 70 (e.g., below the head portion 76 on the shaft portion 74 and/or about or on the head portion 76) prior to installation of the same. While not shown in FIGS. 3A and 3B, the head portion 76 of the screw 70 can include one or more informational marker locations and/or informational markers that are the same as, or similar to, the informational marker locations 62 and the informational markers 64 described above in reference to the temporary abutment 10 (see e.g., notches 478 of screw 470 in FIG. 8C). Such informational markers on the screw 70 can provide and/or be indicative of information such as, for example, a connection type of the underlying implant (e.g., implant 120 of FIG. 6A), a manufacturer of the underlying implant, a height, a width, a pitch, a yaw, or a combination thereof, of the screw 70 itself, of the temporary abutment 10, and/or of the underlying implant.

Now referring to FIGS. 4A and 4B, the temporary abutment cap 80 has a generally cylindrical outer surface 81 (or it could have a slight taper) and is configured to fit over the supragingival region 30 of the temporary abutment 10 after the screw 70 is installed. Alternatively, it is contemplated that the temporary abutment cap 80 includes an aperture (see e.g., aperture 483 in temporary abutment cap 480 in FIG. 8D) in a top portion thereof to provide access for the screw 70 to be installed after the temporary abutment cap 80 is installed on the temporary abutment 10.

The temporary abutment cap 80 includes an anti-rotational structure 84 that projects inward from an inner surface 82 of the temporary abutment cap 80. The anti-rotational structure 84 is configured to engage with and/or abut the anti-rotational structure 34 of the temporary abutment 10 in a slidable manner as the temporary abutment cap 80 is slid over the temporary abutment 10. The outer dimensions (e.g., diameter) of the supragingival region 30 of the temporary abutment 10 and the inner dimensions of the inner surface 82 of the temporary abutment cap 80 are configured such that the temporary abutment cap 80 can be slid over the supragingival region 30 in only one rotational orientation. Such a design prevents the temporary abutment cap 80 from rotating with respect to the supragingival region 30 of the temporary abutment 10 once installed. It is contemplated that the temporary abutment cap 80 can include more than one anti-rotational structure 84 configured to mate with a corresponding number of anti-rotational structures 34 of the temporary abutment 10.

The temporary abutment cap 80 includes one or more male circumferential features 86 that are configured to mate with the temporary abutment 10 in a snap-fit type engagement. The one or more male circumferential features 86 are circumferential projections that mate with corresponding ones of the retention grooves 32 on the supragingival region 30 of the temporary abutment 10. Such a mating of the male circumferential features 86 with the retention grooves 32 removably couples the temporary abutment cap 80 to the temporary abutment 10. It is contemplated that such a removable snap-fit type engagement provides a clinician installing the temporary abutment cap 80 with mechanical and/or audible feedback that a bottom end 88 (FIG. 4A) of the temporary abutment cap 80 is properly seated on the flange 50 (FIG. 1A) of the temporary abutment 10.

Now referring to FIGS. 5A and 5B, an abutment assembly 85 includes the temporary abutment 10 engaged with the temporary abutment cap 80 in a snap-fit type engagement. As shown in FIG. 5A, the temporary abutment cap 80 is installed on the temporary abutment 10 such that the bottom end 88 (FIG. 4A) of the temporary abutment cap 80 abuts and/or contacts the flange 50 (FIGS. 1A and 1B) of the temporary abutment 10 and the male circumferential projections 86 (FIGS. 4A and 4B) of the temporary abutment cap 80 engage the retention grooves 32 (FIGS. 1A and 1B) of the temporary abutment 10. As shown in FIG. 5B, the anti-rotational structure 34 of the temporary abutment 10 is positioned adjacent to the anti-rotational structure 84.

Figure 6A:
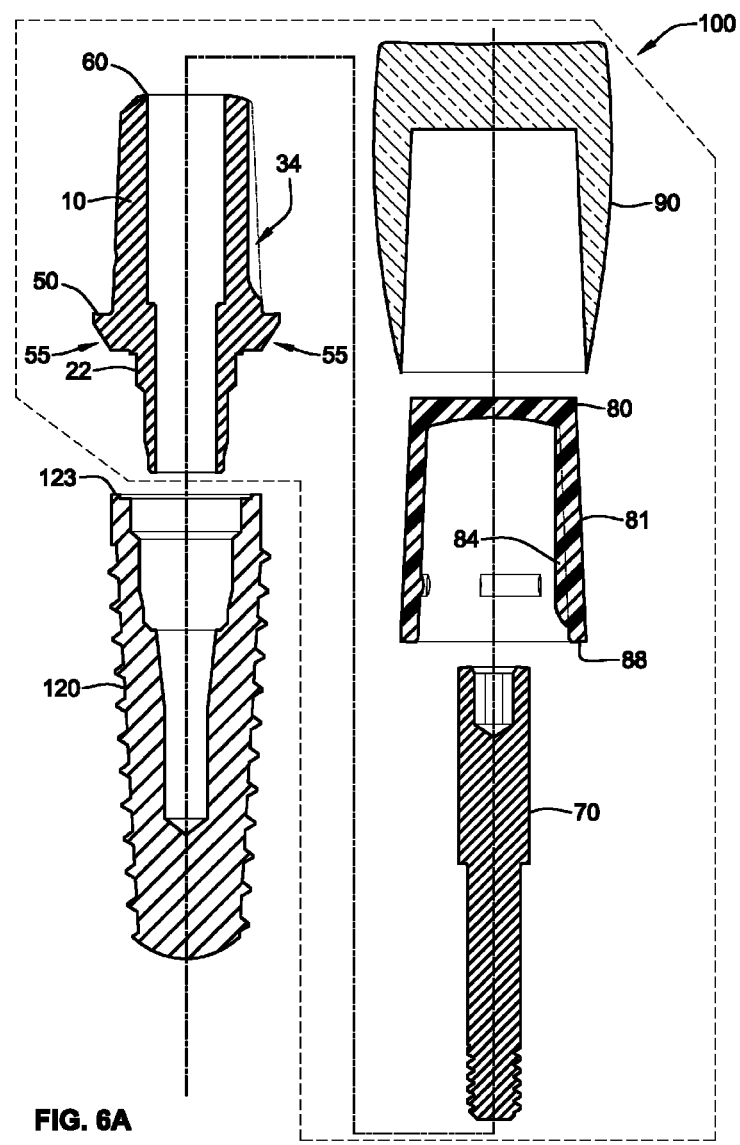
FIG. 6A is an exploded cross-sectional view of a prosthesis assembly and a dental implant.
Figure 6B:
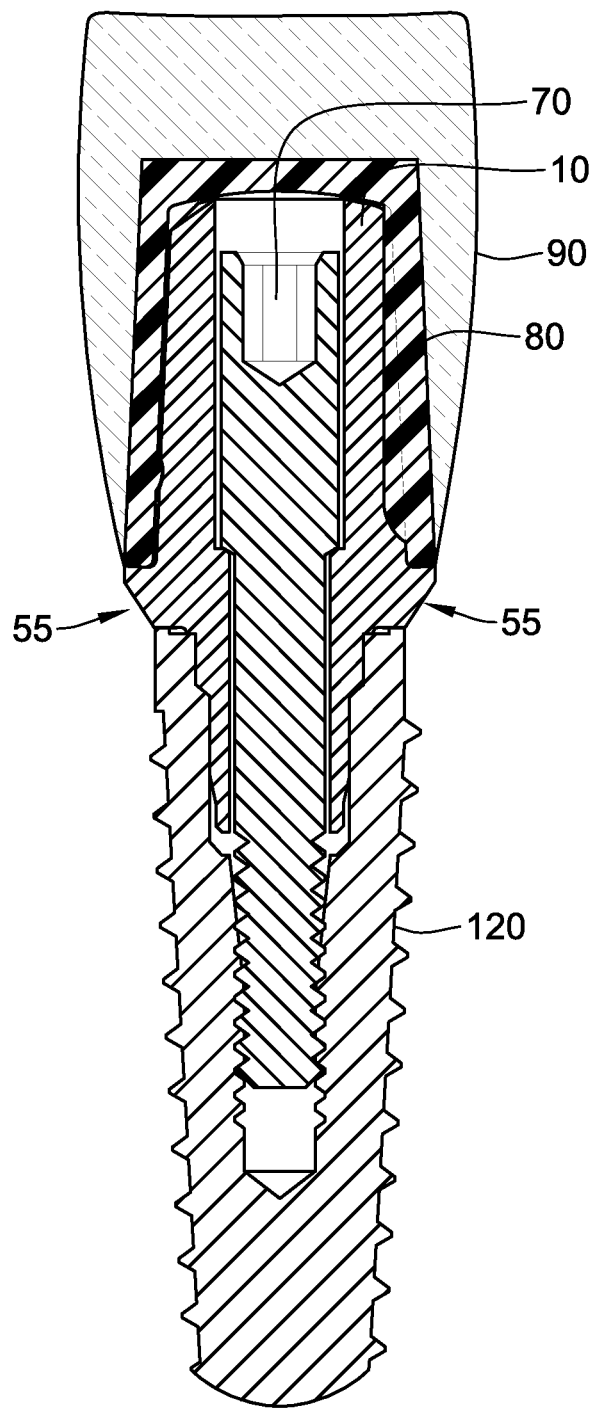
FIG. 6B is an assembled cross-sectional view of the prosthesis assembly coupled to the dental implant shown in FIG. 6A.

Referring to FIGS. 6A and 6B, an exploded view (FIG. 6A) and an assembled view (FIG. 6B) of a temporary prosthesis assembly or a prosthesis assembly 100 and dental implant 120 is shown. The prosthesis assembly 100 includes the temporary abutment 10 and the temporary abutment cap 80 coupled to a temporary prosthesis 90 (e.g., a temporary tooth). The implant 120 is installed in the jawbone (not shown) of a patient, and then the temporary abutment 10 is non-rotationally attached to the implant 120 via the non-rotational feature 22 and the screw 70. The temporary abutment 10 is attached to the implant 120 such that a bottom portion of the flange 50 of the temporary abutment 10 abuts and/or rests upon a table or seating surface 123 of the dental implant 120. The temporary abutment cap 80 is snap-fitted onto the temporary abutment 10 and then the temporary prosthesis 90 is coupled to the temporary abutment cap 80.

The outer surface 81 of the temporary abutment cap 80 is configured to mate with and/or to be bonded with the temporary prosthesis 90. It is contemplated that the temporary prosthesis 90 is coupled to the temporary abutment cap 80 using cement (e.g., dental cement), glue, bonding agent, a press-fit engagement, a snap or click-type engagement, a screw or bolt, or a combination thereof. It is further contemplated that the temporary prosthesis 90 is removably or permanently coupled to the temporary abutment cap 80 such that the temporary prosthesis 90 and the temporary abutment cap 80 can be removed separately or in unison from the temporary abutment 10. Removal of the temporary prosthesis 90 and the temporary abutment cap 80 exposes the top surface of the temporary abutment 10 including the informational markers 64, which can be scanned directly or indirectly (e.g., from an impression and/or stone/plaster model) to generate scan data that is at least used to determine the location and orientation of the implant 120, which, as explained herein, is used when developing a permanent patient-specific abutment and/or prosthesis.

The outer surface of the temporary prosthesis 90 and/or the outer surface 55 of the flange 50 are configured to be suitable for replicating the gingival emergence profile formed by a natural tooth (e.g., in a non-round shape). As such, after the temporary prosthesis 90 is installed, the patient's gingiva is permitted to heal around the temporary prosthesis 90 and/or the temporary abutment 10. Such a prosthesis assembly 100 results in a gingival emergence profile approximating that of what would be around a natural tooth and/or that of what a clinician determined to be most appropriate for the given implant installation site (e.g., an ovular shape). In other words, the prosthesis assembly 100 also acts as a gingival healing abutment. This is advantageous because, after the patient's mouth has an opportunity to heal and is ready to be processed (e.g., intra-oral direct scanning, impression scanning, or scanning of a model formed from the impression) for creating a permanent patient-specific abutment and prosthesis, the temporary prosthesis 90 and the temporary abutment cap 80 are removed to reveal the temporary abutment 10 and the resulting emergence profile of the adjacent gingiva. Because the resulting emergence profile approximates that of a natural tooth, the permanent patient-specific abutment and prosthesis can be accurately created from the scan data and/or from known data associated with the temporary abutment 10 (e.g., the known contours of the outer surface 55 of the flange 50 of the temporary abutment 10). For example, the permanent patient-specific abutment and prosthesis can be created and attached to the underlying implant 120 such that the permanent patient-specific abutment and prosthesis (not shown) are highly aesthetic and fit closely within the gingiva emergence profile adjacent to the implant 120 that was formed by the prosthesis assembly 100.

To create a permanent patient-specific abutment and prosthesis (not shown), after the temporary abutment cap 80 and attached temporary prosthesis 90 are removed, the dental region of the patient's mouth including the temporary abutment 10 is scanned from a stone model (i.e., a replica of the patient's dental conditions), from impression material of an impression of the patient's dental conditions including the temporary abutment 10, or directly in the mouth of the patient. Scanning can be accomplished using a laser scanning technique, a photographic scanning technique, or a mechanical sensing technique. These methods of scanning directly in a patient's mouth, an impression of the same, and a model of the same, using any of the aforementioned techniques, are described in further detail in U.S. Pat. No. 7,988,449, which was previously incorporated by reference herein in its entirety.

The scanned data or information obtained from the scanning process is then transferred to a graphical imaging program for analysis. The graphical imaging software program, due to the information markers 64 on the top surface 60 of the temporary abutment 10, can aid in performing a wide variety of functions. For example, the graphical imaging program can scan an opposing cast in order to develop an opposing occlusal scheme and relate this information back to the primary model. This feature is extremely important because many clinical patients have implants in both maxillary and mandibular locations. Each of the features of the temporary abutment 10 and underlying implant 120 is analyzed and determined based on the presence/absence of the information markers 64 and the orientation/location of the informational markers 64 on the top surface 60 of the temporary abutment 10. And, as mentioned above, the emergence contour or profile of the gingival tissue that was created by the prosthesis assembly 100 is also received in the scan.

Final dimensional information determined by the graphical imaging computer program is transferred from the computer to a milling machine (e.g., a 5 axis milling machine) to fabricate the permanent patient-specific abutment and/or permanent prosthesis. It is contemplated that the permanent patient-specific abutment and/or permanent prosthesis can be fashioned from gold, titanium, plastic, ceramic, or other similar metals or composites.

Alternatively and/or additionally, one or more rapid prototype models of the patient's mouth, including a replica of the gingival contours, can be fabricated based on the dimensional information and/or the original scanned information/data. The rapid prototype model(s) can be used by a clinician to develop, for example, the permanent prosthesis. Additional details on rapid prototype models and rapid prototyping in general can be found in U.S. Pat. No. 8,185,224, which is hereby incorporated by reference herein in its entirety.

Figure 7A:
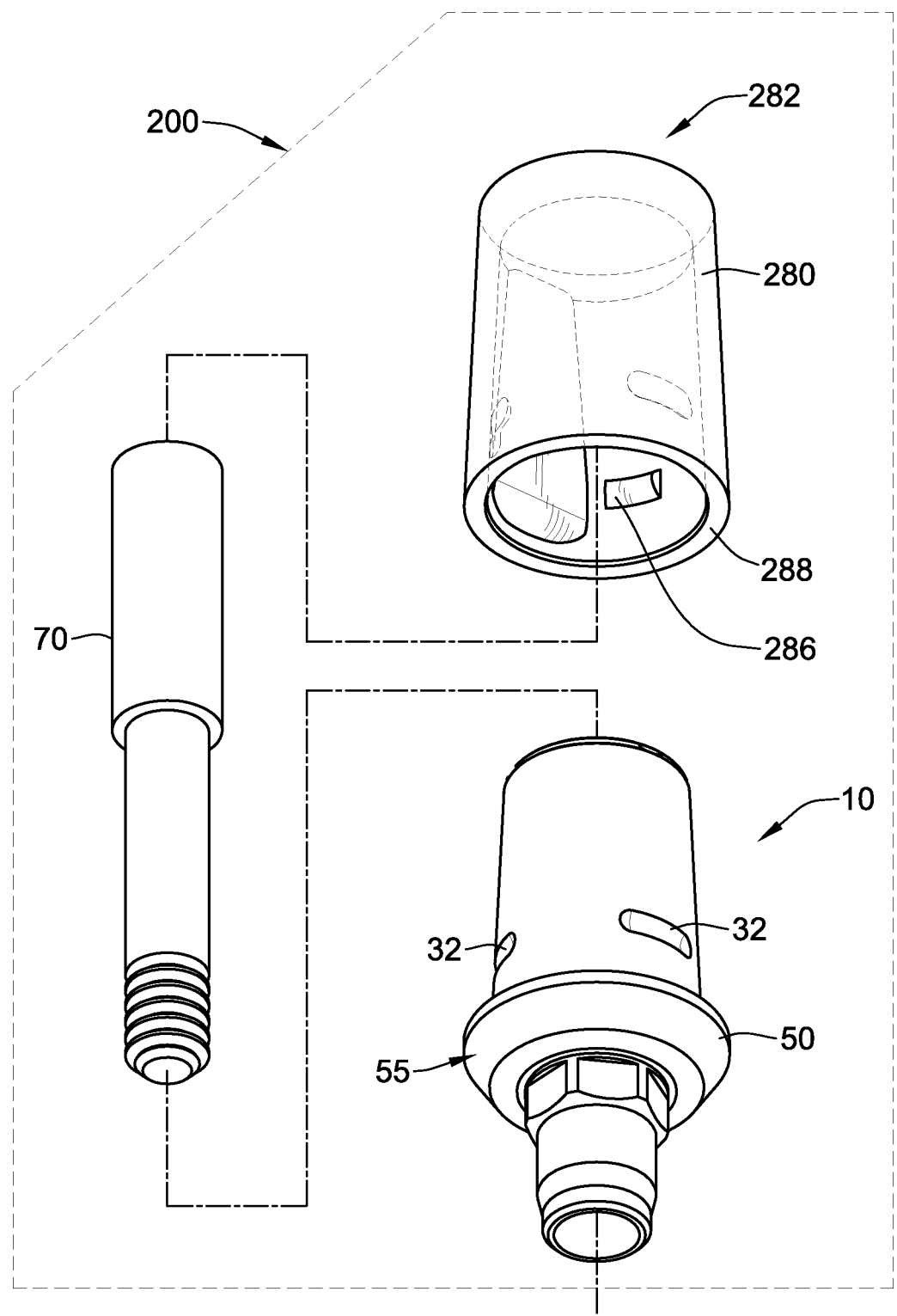
FIG. 7A is an exploded perspective view of an unmodified temporary abutment assembly including a temporary abutment, an unmodified temporary abutment cap, and a fastening device.
Figure 7B:
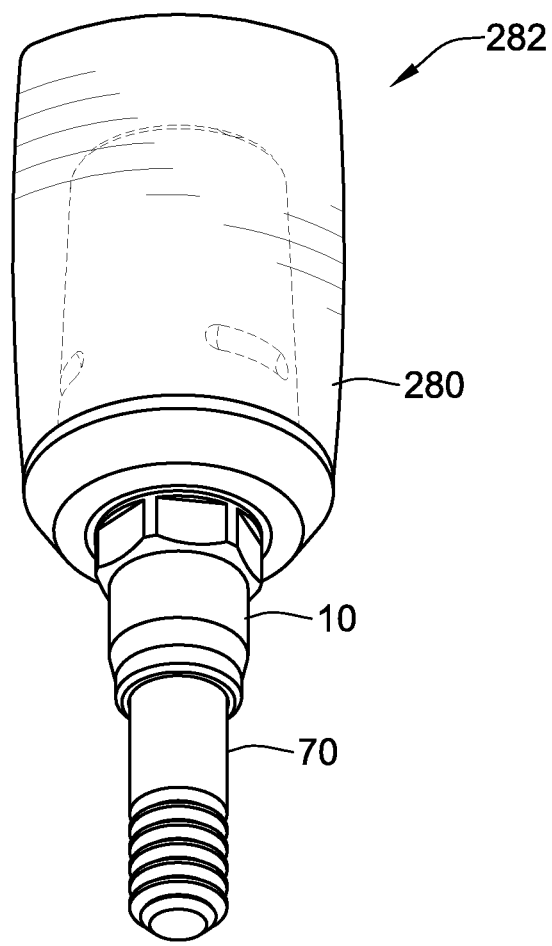
FIG. 7B is an assembled perspective view of the assembly shown in FIG. 7A with the temporary abutment cap modified.

FIGS. 7A-7B illustrate an alternative abutment assembly 200. FIG. 7A shows an exploded view of the abutment assembly 200 including the temporary abutment 10 and a temporary abutment cap 280. The temporary abutment cap 280 is configured to be installed on the temporary abutment 10 such that (1) a bottom end 288 of the temporary abutment cap 280 abuts and/or contacts a top portion of the flange 50 of the temporary abutment 10 and (2) male circumferential projections 286 of the temporary abutment cap 280 engage the retention grooves 32 of the temporary abutment 10 in a snap-fit type engagement.

The temporary abutment cap 280 is similar to the temporary abutment cap 80, described herein and shown in FIGS. 4A and 4B, except that the temporary abutment cap 280 includes additional material 282 configured to be cut or shaved or otherwise modified by a clinician to approximate the size, shape, position, and general likeness of an anatomically shaped tooth when attached to the temporary abutment 10. For example, as shown in FIG. 7B, the additional material 282 of the temporary abutment cap 280 is modified to look like an anatomically shaped tooth when attached to the temporary abutment 10 installed on the dental implant 120 (not shown in FIG. 7B) in the mouth of a patient. The embodiment of FIGS. 7A and 7B is different from FIGS. 4A and 4B in which material (e.g., the temporary prosthesis 90) is added to the temporary abutment cap 80 to form the emergence profile of the gingival tissue.

Alternatively, the additional material 282 can be modified such that the modified portion of the temporary abutment cap 280 is configured to be coupled with a temporary prosthesis or crown (not shown) in a manner similar to how the temporary prosthesis 90 is coupled to the temporary abutment cap 80, described above and shown in FIGS. 6A and 6B.

According to some additional alternative implementations of the present aspects, in lieu of a clinician modifying the additional material 282 of the temporary abutment cap 280, a temporary abutment cap can be supplied with a shape and size such that the temporary abutment cap includes an outer surface that approximates the size and shape of an anatomically shaped tooth when attached to the temporary abutment 10 installed on the dental implant 120 in the mouth of a patient. That is, it is contemplated that a temporary abutment cap can be formed with an outer surface that includes a preformed anatomically shaped tooth (e.g., a tooth prosthesis) that is configured to be attached to the temporary abutment 10 in a similar manner as the temporary abutment cap 80 is attached to the temporary abutment 10 described herein.

It is further contemplated that a kit or package of temporary abutment caps, where each temporary abutment cap includes an outer surface with an anatomically shaped tooth (not shown), can be supplied and/or packaged together for use by, for example, clinicians. In such alternatives, the clinician is supplied with a variety of temporary abutment caps including different anatomically shaped teeth that can be attached to the temporary abutment 10 as described herein and used directly as temporary prostheses without further modification or attachment of additional components. In each of these alternatives, the temporary abutment 10 is still useful for scanning.

In some implementations of the disclosed concepts, the retention grooves 32 and the male circumferential features 86 can be formed to provide a fixed rotational orientation between the temporary abutment 10, 10' and the temporary abutment cap 80. For example, one or more of the retention grooves 32 can have a unique length and/or size (as compared with the other ones of the retention grooves 32) that is designed to mate with a corresponding one of the male circumferential features 86 having a corresponding unique length and/or size (as compared with the other ones of the male circumferential features 86) such that the temporary abutment cap 80 can only be attached (e.g., via snap-fit connection) to the temporary abutment 10, 10' in one rotational orientation.

Figure 8A:
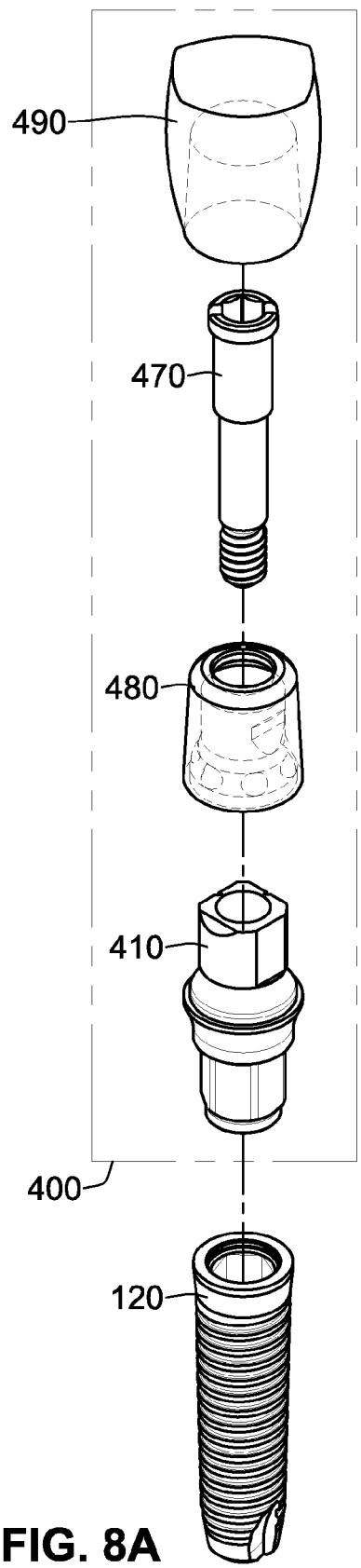
FIG. 8A is an exploded perspective view of a prosthesis assembly and an implant according to an alternative embodiment of the invention.

Referring to FIGS. 8A to 8F, various views of components of an alternative prosthesis assembly 400 and the dental implant 120 are shown. As shown in FIG. 8A, the prosthesis assembly 400 includes a temporary abutment 410, a temporary abutment cap 480, a screw 470, and a temporary prosthesis 490, each of which is similar to, or the same as, corresponding components of the previously described prosthesis assemblies. In FIGS. 8A to 8F, each of the components and features is identified by a 400-series reference numeral, and those 400-series reference numerals correspond to like features of the various components and features of the previously described prosthesis assemblies. For example, reference numeral 434 is used to describe the non-rotational structure 434 (FIG. 8B), which is the same as, or similar to, the non-rotational structure 34 (FIG. 1A). Additionally, reference numerals 440, 460, 472, 474, and 481 are used in the figures to illustrate features that are the same as, or similar to, previously described features with reference numbers 40, 60, 72, 74, and 81, respectively.

Referring to FIG. 8B, the temporary abutment 410 generally includes all of the same features as the temporary abutment 10, which is most similar to the temporary abutment 410; however, the temporary abutment 410 has a different overall shape and/or size. Specifically, the temporary abutment 410 includes a continuous retention groove 432 that circumscribes the entire supragingival region 430 of the temporary abutment 410 instead of including the retention grooves 32 (FIG. 1A) of the temporary abutment 10. Additionally, the continuous retention groove 432 (FIG. 8B) is positioned completely below the non-rotational structure 434 of the temporary abutment 410 as compared to the positioning of the retention grooves 32 of the temporary abutment 10 which are positioned adjacent to a central region of the non-rotational structure 34 of the temporary abutment 10 (e.g., the retention grooves 32 are relatively higher on the temporary abutment 10). Irrespective of the placement of the continuous retention groove 432 on the supragingival region 430 of the temporary abutment 410, the continuous retention groove 432 (FIG. 8B) functions in the same, or similar, manner as the retention grooves 32 (FIG. 1A) in that the continuous retention groove 432 is configured to mate with one or more projections 486 of the temporary abutment cap 480 (FIG. 8D) in a snap-fit type engagement (shown in FIG. 8F).

Figure 8E:
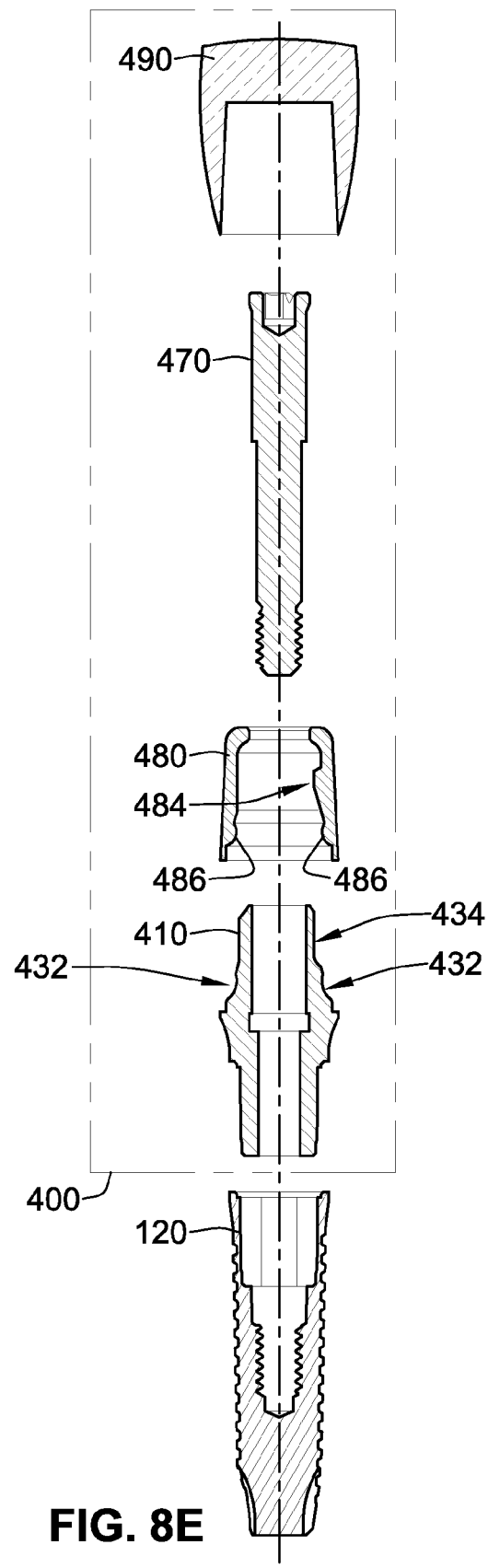
FIG. 8E is an exploded cross-sectional view of the prosthesis assembly and the implant of FIG. 8A.
Figure 8F:
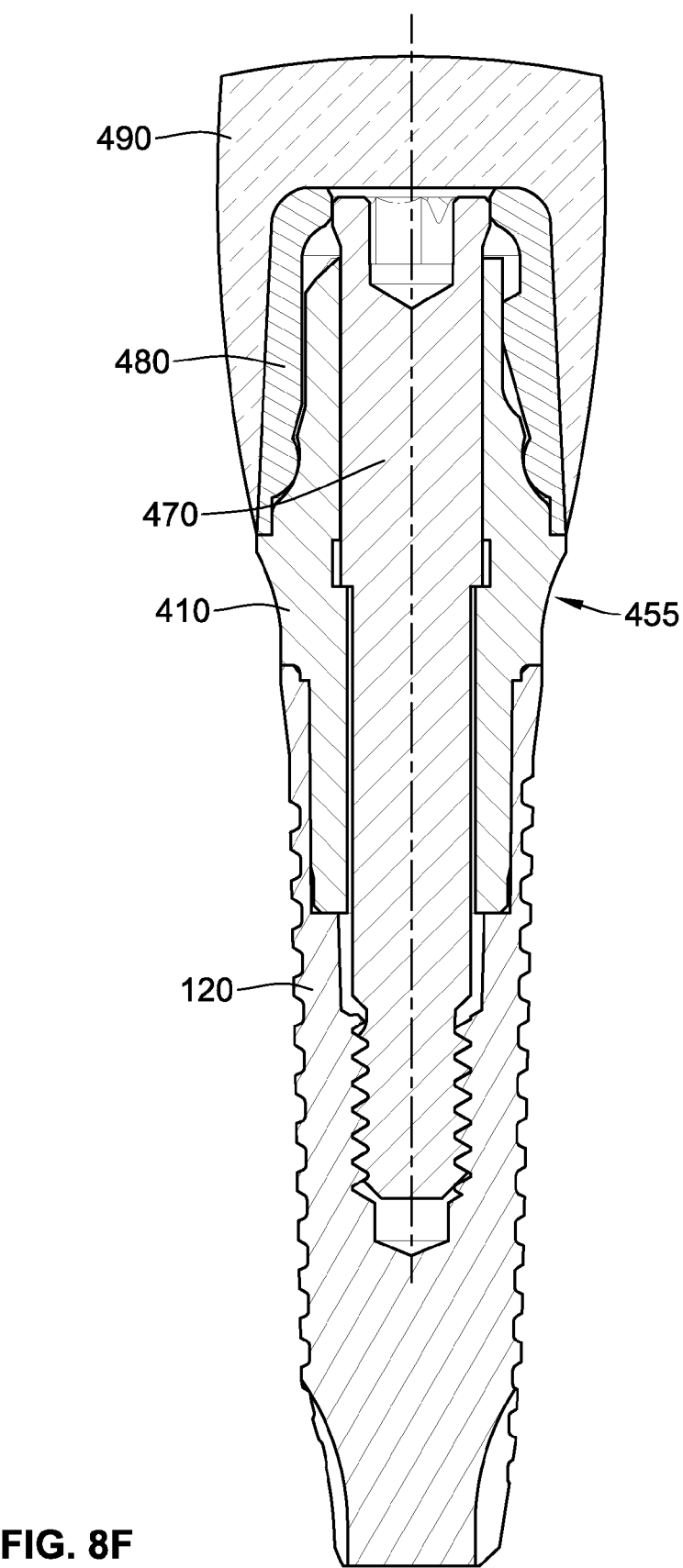
FIG. 8F is an assembled cross-sectional view of the prosthesis assembly and the implant of FIG. 8A.

An outer surface 455 of a flange 450 of the temporary abutment 410 (e.g., portion of 410 that separates a subgingival region 420 and a supragingival region 430) also differs from the outer surface 55 of the flange 50 of the temporary abutment 10, which is best seen by comparing FIG. 6B with FIG. 8F. Specifically, the outer surface 455 of the flange 450 of the temporary abutment 410 has a differently shaped contour for engaging and aiding in forming a patient's gingival tissue during the healing process. Various other contours of the outer surface 455 of the flange 450 can be used depending on the particular conditions present in the patient's mouth.

A further difference between the temporary abutment 410 (FIG. 8B) and the temporary abutment 10 (FIG. 1A) is that the temporary abutment 410 includes three informational marker locations 462 and two informational markers 464 as compared to the two informational marker locations 62 and the one informational marker 64 of the temporary abutment 10. The additional informational marker location 462 can aid in providing additional information about the temporary abutment 410 and/or the underlying dental implant 120 by providing, for example, additional potential binary combinations (e.g., three binary informational markers provide the ability to identify eight different configurations).

Referring to FIG. 8C, the screw 470 generally includes all of the same features as the screw 70; however, an upper part of a head portion 476 of the screw 470 is modified. Specifically, in addition to the head portion 476 including a socket 479 to accept a wrench (not shown) for threadably engaging the screw 470 into the threaded bore of the implant 120 (see FIGS. 8A, 8E, and 8F), the head portion 476 includes a lip 477 and one or more notches 478.

The lip 477 has a larger outer diameter than the outer diameter of the rest of the head portion 476 such that the lip 477 engages with the temporary abutment cap 480 when the temporary abutment cap 480 is engaged with (e.g., snapped onto) the temporary abutment 410 as best shown in FIG. 8F. Such an engagement between the lip 477 and the temporary abutment cap 480 provides additional rigidity to the prosthesis assembly 400 in its assembled configuration (FIG. 8F). Alternatively, the screw 470 can be sized and shaped such that the head portion 476 does not engage the temporary abutment cap 480 (see e.g., FIG. 6B).

The one or more notches 478 in the head portion 476 can act as informational marker locations and/or informational markers in the same, or similar, manner as the informational marker locations 62, 462 and the informational markers 64, 464 described herein. Specifically, the notches 478 can indicate information regarding one or more aspects of the prosthesis assembly 400 and/or the dental implant 120, such as, for example, a connection type of the underlying implant, the type of prosthesis assembly, a manufacturer of the underlying implant, a height, a width, a pitch, a yaw, or a combination thereof of the temporary abutment 410 and/or of the underlying implant 120, etc.

Referring to FIG. 8D, the temporary abutment cap 480 generally includes all of the same features as the temporary abutment cap 80, which is most similar to the temporary abutment cap 480; however, the temporary abutment cap 480 has a different overall shape and/or size to correspond with the temporary abutment 410. Specifically, while the temporary abutment cap 480 includes one or more projections 486 (similar to the projections 86 of the temporary abutment cap 80 in FIG. 4A), the projections 486 (FIG. 8D) are formed by a continuous projection that circumscribes an inner surface 482 of the temporary abutment cap 480 that is separated into the projections 486 by a plurality of notches 487. The notches 487 allow for the temporary abutment cap 480 to be removed from the temporary abutment 410, when engaged in the snap-fit type engagement shown in FIG. 8F, with relatively less force then if the projections 486 were continuous (e.g., not separated by the notches 487). Alternatively, the projections 486 (FIG. 8D) of the temporary abutment cap 480 can be formed in the same, or similar manner as the projections 86 (FIG. 4A) of the temporary abutment cap 80 (e.g., without the notches 487).

Additionally, the projections 486 (FIG. 8D) are positioned completely below the non-rotational structure 484 of the temporary abutment cap 480 as compared to the positioning of the projections 86 (FIG. 4A) of the temporary abutment cap 80 which are positioned adjacent to a central region of the non-rotational structure 84 of the temporary abutment cap 80 (e.g., the projections 86 of the temporary abutment cap 80 are relatively higher). The positioning of the projections 486 (FIG. 8D) can aid in providing a seal between a lower or apical end (e.g., a bottom end 488) of the temporary abutment cap 486 and the temporary abutment 410 (e.g., by forcing the lower end downwardly). Irrespective of the placement of the projections 486 on the inner surface 482 of the temporary abutment cap 480, the projections 486 (FIG. 8D) function in the same, or similar, manner as the projections 86 (FIG. 4A) in that the projections 486 (FIG. 8D) are configured to mate with the continuous retention groove 432 of the temporary abutment 410 (FIG. 8B) in a snap-fit type engagement (best shown in FIG. 8F).

A further difference between the temporary abutment cap 480 (FIG. 8D) and the temporary abutment cap 80 (FIG. 4A) is that the temporary abutment cap 480 includes an aperture 483 in a top portion thereof to provide access for the screw 470 to be installed after the temporary abutment cap 480 is installed on (e.g., snapped onto) the temporary abutment 410. As described above in reference to the screw 470 of FIG. 8C, the wall of the aperture 483 can engage with the lip 477 of the screw 470 for additional rigidity of the prosthesis assembly 400.

Referring to FIGS. 8E and 8F, a cross-sectional exploded view (FIG. 8E) and a cross-sectional assembled view (FIG. 8F) of the prosthesis assembly 400 and the dental implant 120 are shown for illustrating how the various components of the prosthesis assembly 400 are assembled and attached to the dental implant 120. The dental implant 120 is installed in a patient's jawbone (not shown) and then the temporary abutment 410 is non-rotationally attached to the implant 120 via a non-rotational feature 422 (FIG. 8B) and the screw 470. The temporary abutment cap 480 is snap-fitted onto the temporary abutment 410 in a non-rotational manner such that the non-rotational structure 434 (FIG. 8B) of the temporary abutment 410 engages the non-rotational structure 484 (FIG. 8D) of the temporary abutment cap 480. The temporary prosthesis 490 is coupled to the temporary abutment cap 480 in the same, or similar, manner as described herein in reference to the temporary prosthesis 90 being coupled to the temporary abutment 80 (FIGS. 6A and 6B). Alternatively, as the temporary abutment cap 480 includes the aperture 483 (FIG. 8D), the temporary abutment cap 480 can be snap-fitted onto the temporary abutment 410 prior to the screw 470 being installed. Then, the screw 470 can be installed through the aperture 483, which is followed by the temporary prosthesis 490 being coupled to the temporary abutment cap 480.

Figure 9B:
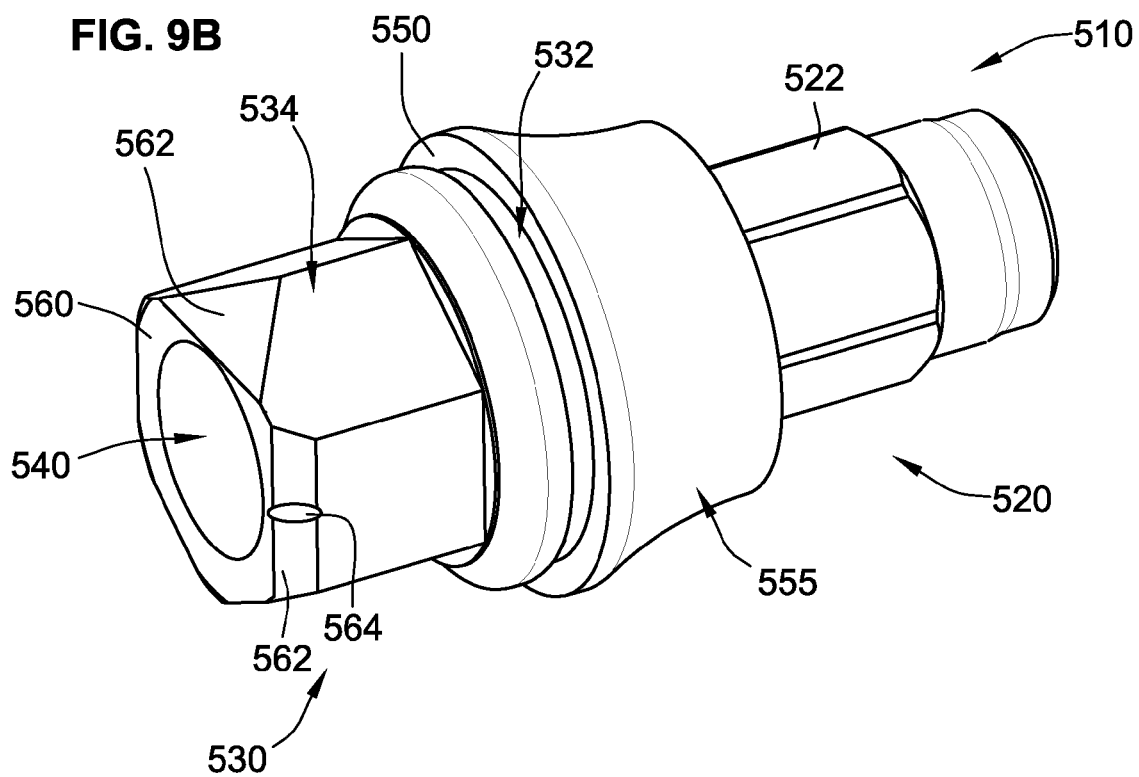
FIG. 9B is a perspective view of a temporary abutment of the prosthesis assembly of FIG. 9A.

Referring to FIGS. 9A to 9E, various views of components of an alternative prosthesis assembly 500 and the dental implant 120 are shown. As shown in FIG. 9A, the prosthesis assembly 500 includes a temporary abutment 510, a temporary abutment cap 580, a screw 570, and a temporary prosthesis 590, each of which is similar to, or the same as, corresponding components of the previously described prosthesis assemblies. In FIGS. 9A to 9E, each of the components and features is identified by a 500-series reference numeral, and those 500-series reference numerals correspond to like features of the various components and features of the previously described prosthesis assemblies. For example, reference numeral 534 is used to describe the non-rotational structure 534 (FIG. 9B), which is the same as, or similar to, the non-rotational structure 34 (FIG. 1A) and the non-rotational structure 434 (FIG. 8B). Additionally, reference numerals 520, 540, 555, 560, 581, and 587 are used in the figures to illustrate features that are the same as, or similar to, previously described features with reference numbers 20, 40, 55, 60, 81, and 487 respectively.

Referring to FIG. 9B, the temporary abutment 510 generally includes all of the same features as the temporary abutments 10 and 410; however, several differences exist between the temporary abutment 510 and the temporary abutment 410, which is most similar to the temporary abutment 510. Specifically, the temporary abutment 510 includes a continuous retention groove 532 (FIG. 9B) that is positioned directly above a flange 550 as compared to the positioning of the continuous retention groove 432 of the temporary abutment 410 (best shown by comparing FIG. 8E with 9D). Irrespective of the placement of the continuous retention groove 532 on a supragingival region 530 of the temporary abutment 510, the continuous retention groove 532 (FIG. 9B) functions in the same, or similar, manner as the continuous retention groove 432 (FIG. 8B) in that the continuous retention groove 532 is configured to mate with one or more projections 586 of the temporary abutment cap 580 (FIG. 9C) in a snap-fit type engagement (shown in FIG. 9E).

A non-rotational structure 534 of the temporary abutment 510 is a six-sided hexagonal boss as compared to the single flat surface of the non-rotational structures 34, 434 (see e.g., FIGS. 1A and 8B). Various other non-rotational structures can be used to prevent relative rotation between the temporary abutment 510 and the temporary abutment cap 580 (e.g., three-sided polygonal boss, four-sided polygonal boss, clover boss, etc.).

A further difference between the temporary abutment 510 (FIG. 9B) and the temporary abutment 410 (FIG. 8B) is that the temporary abutment 510 includes two informational marker locations 562 and one informational marker 564 as compared to the three informational marker locations 462 and the two informational marker 464 of the temporary abutment 410. Moreover, the informational marker locations 562 of the temporary abutment 510 are in the shape of a rectangular surface and a triangular surface. The differently shaped informational marker locations 562 themselves can aid in providing information about the temporary abutment 510 and/or the underlying dental implant 120. For example, a sole triangular informational marker location 562 can indicate a particular manufacturer and, for another example, both a rectangular and a triangular informational marker 562 on a temporary abutment can indicate a different manufacturer.

Figure 9C:
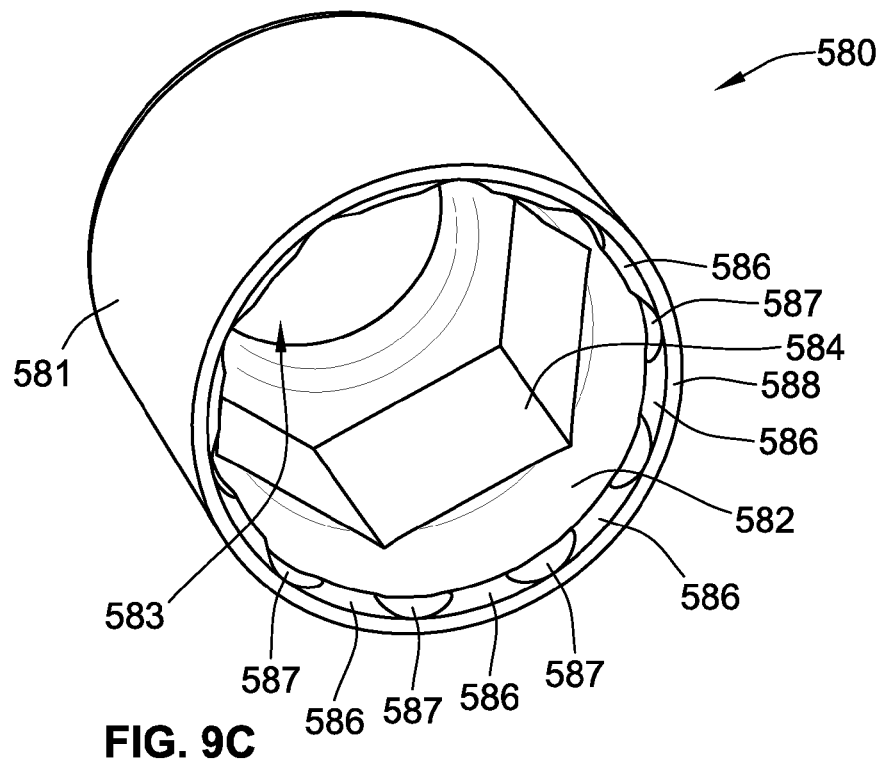
FIG. 9C is a perspective view of a temporary abutment cap of the prosthesis assembly of FIG. 9A.

Referring to FIG. 9C, the temporary abutment cap 580 generally includes all of the same features as the temporary abutment caps 80 and 480 except for a few differences. One or more projections 586 of the temporary abutment cap 580 are positioned relatively lower as compared to the positioning of the projections 486 of the temporary abutment cap 480 (best shown by comparing FIG. 8F with FIG. 9E). Irrespective of the placement of the projections 586 on an inner surface 582 of the temporary abutment cap 580, the projections 586 (FIG. 9C) function in the same, or similar, manner as the projections 86 (FIG. 4A) in that the projections 586 (FIG. 9C) are configured to mate with the continuous retention groove 532 of the temporary abutment 510 in a snap-fit type engagement (best shown in FIG. 9E).

A further difference between the temporary abutment cap 580 (FIG. 9C) and the temporary abutment cap 480 (FIG. 8D) is that the temporary abutment cap 580 includes a non-rotational structure 584 that is a six-sided hexagonal socket (FIG. 9C) as compared to the single flat surface of the non-rotational structure 484 of the temporary abutment cap 480 (FIG. 8D). The non-rotational structure 584 can be any of a variety of structures that corresponds with the non-rotational structure 534 to prevent relative rotation between the temporary abutment 510 and the temporary abutment cap 580.

Figure 9E:
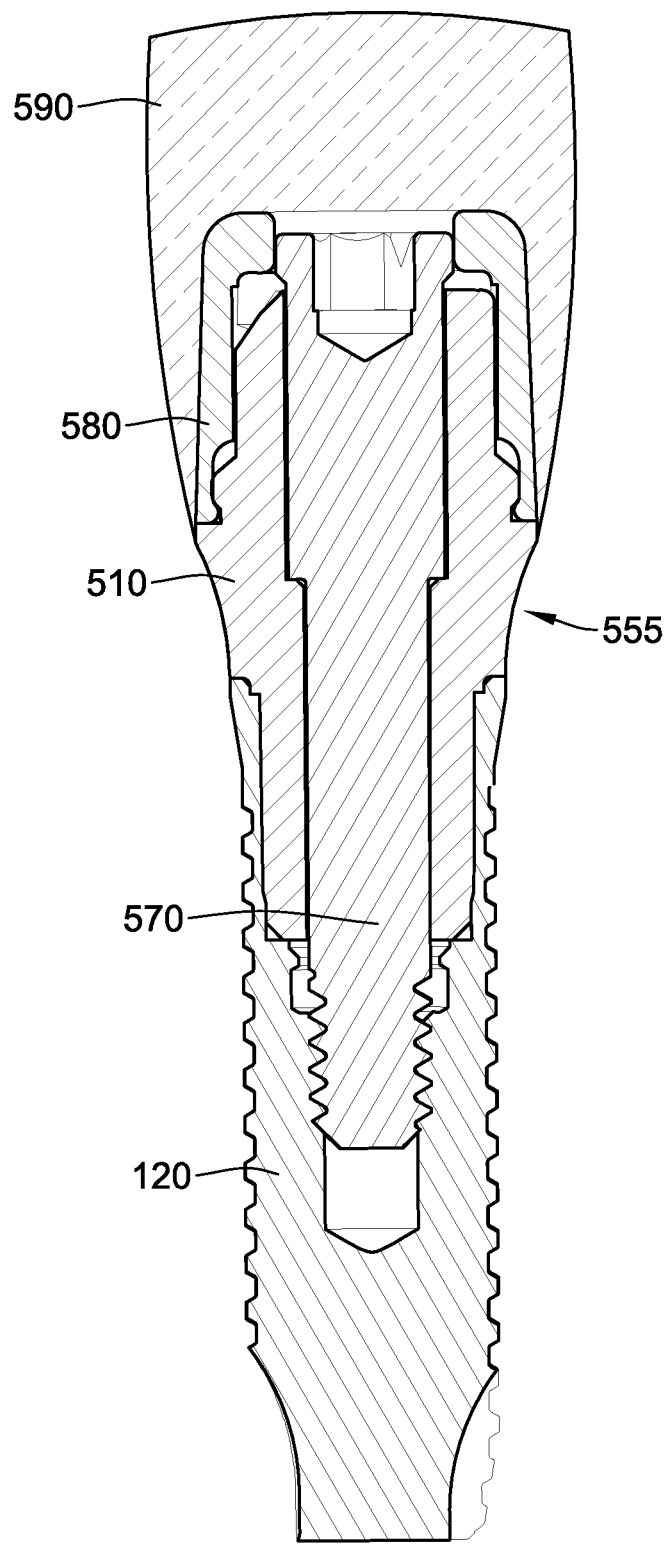
FIG. 9E is an assembled cross-sectional view of the prosthesis assembly and the implant of FIG. 9A.

Referring to FIGS. 9D and 9E, a cross-sectional exploded view (FIG. 9D) and a cross-sectional assembled view (FIG. 9E) of the prosthesis assembly 500 and the dental implant 120 are shown for illustrating how the various components of the prosthesis assembly 500 are assembled and attached to the dental implant 120. The dental implant 120 is installed in a patient's jawbone (not shown) and then the temporary abutment 510 is non-rotationally attached to the implant 120 via the non-rotational feature 522 (FIG. 9B) and the screw 570. The temporary abutment cap 580 is snap-fitted onto the temporary abutment 510 in a non-rotational manner such that the non-rotational structure 534 (FIG. 9B) of the temporary abutment 510 engages the non-rotational structure 584 (FIG. 9C) of the temporary abutment cap 580. The temporary prosthesis 590 is coupled to the temporary abutment cap 580 in the same, or similar, manner as described herein in reference to the temporary prosthesis 90 being coupled to the temporary abutment 80 (FIGS. 6A and 6B). Alternatively, as the temporary abutment cap 580 includes an aperture 583 (FIG. 9C), the temporary abutment cap 580 can be snap-fitted onto the temporary abutment 510 prior to the screw 570 being installed. Then, the screw 570 can be installed through the aperture 583, which is followed by the temporary prosthesis 590 being coupled to the temporary abutment cap 580.

Figure 10A:
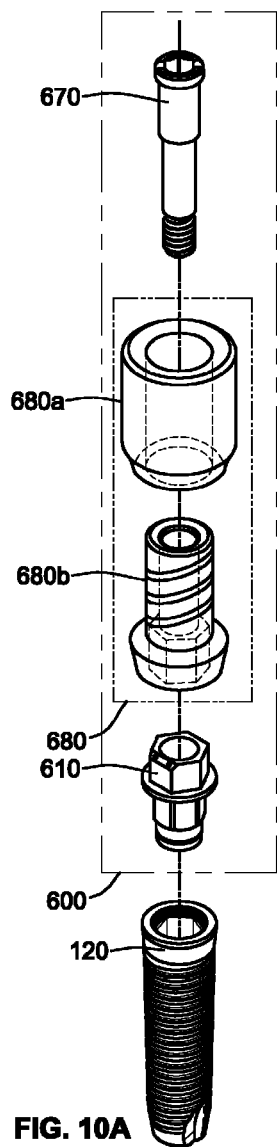
FIG. 10A is an exploded perspective view of a prosthesis assembly and an implant according to yet a further alternative embodiment of the invention.

Referring to FIGS. 10A to 10E, various views of components of an alternative prosthesis assembly 600 and the dental implant 120 are shown. As shown in FIG. 10A, the prosthesis assembly 600 includes a temporary abutment 610, a temporary abutment cap 680, and a screw 670, each of which is similar to, or the same as, corresponding components of the previously described prosthesis assemblies. In FIGS. 10A to 10E, each of the components and features is identified by a 600-series reference numeral, and those 600-series reference numerals correspond to like features of the various components and features of the previously described prosthesis assemblies. For example, reference numeral 634 is used to describe the non-rotational structure 634 (FIG. 10B), which is the same as, or similar to, the non-rotational structure 34 (FIG. 1A).

Figure 10D:
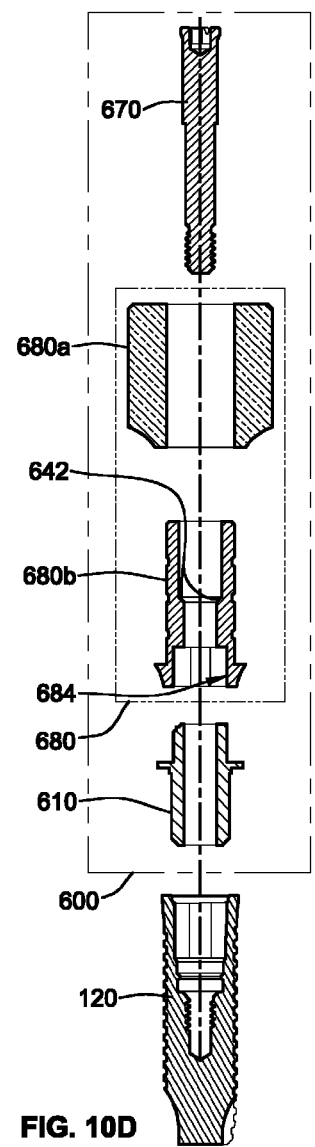
FIG. 10D is an exploded cross-sectional view of the prosthesis assembly and the implant of FIG. 10A.
Figure 10B:
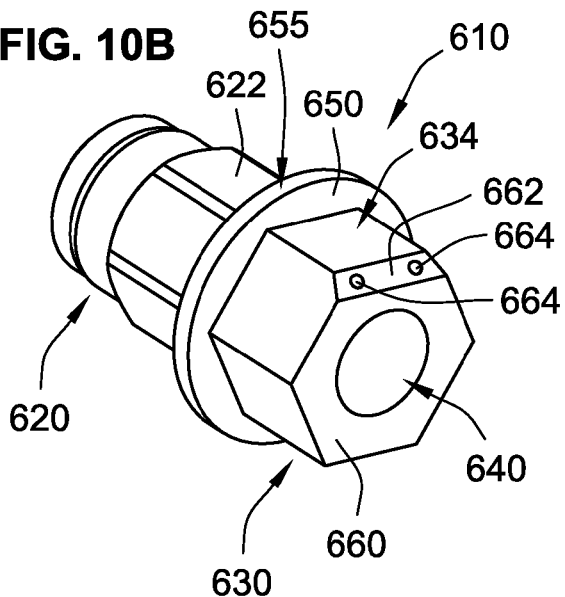
FIG. 10B is a perspective view of a temporary abutment of the prosthesis assembly of FIG. 10A.
Figure 10E:
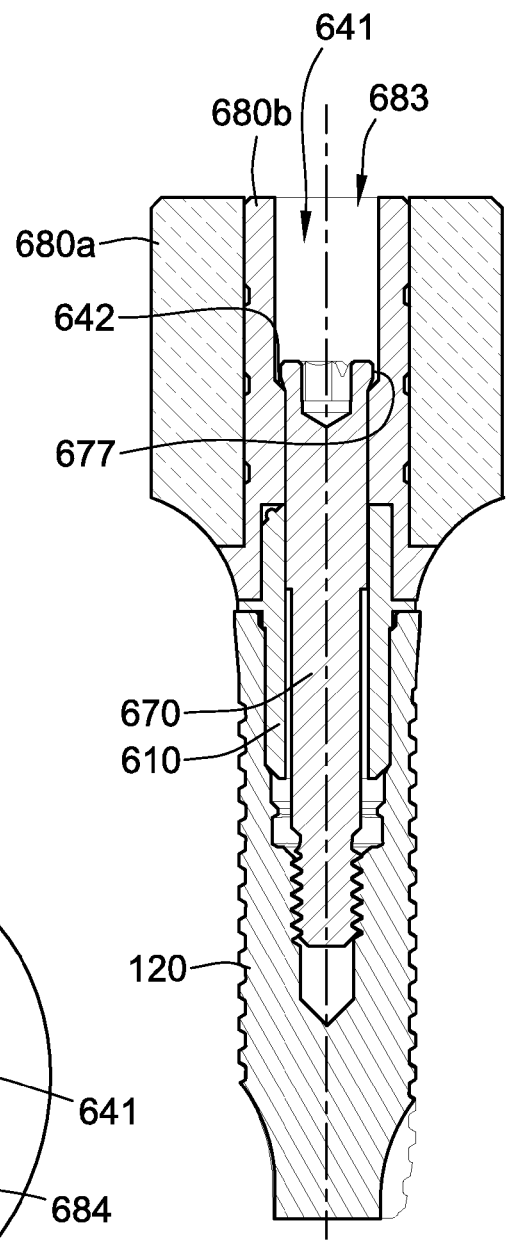
FIG. 10E is an assembled cross-sectional view of the prosthesis assembly and the implant of FIG. 10A.

Referring to FIG. 10B, the temporary abutment 610 generally includes most of the same features as the temporary abutments 10, 410, 510; however, several differences exist between the temporary abutment 610 and the temporary abutment 510, which is most similar to the temporary abutment 610. Specifically, an outer surface 655 of a flange 650 of the temporary abutment 610 (e.g., the portion of the temporary abutment 610 between a subgingival region 620 and a supragingival region 630) is relatively shorter as compared to the previous embodiments. A longer flange with an outer surface 655 having a relatively longer contour is not provided by the temporary abutment 610 as the shaping of contour of the patient's gingiva during healing is based mostly on the outer contours of the lower portion of the temporary abutment cap 680, the contours of which are best seen in FIG. 10E. Various other contours of the lower portion of the temporary abutment 680 can be used depending on the particular conditions present in the patient's mouth.

The temporary abutment 610 lacks the continuous retention groove 532 of the temporary abutment 510 as the temporary abutment cap 680 does not engage the temporary abutment 610 in a snap-fit type engagement. Rather, the temporary abutment cap 680 is coupled to the implant 120 and the temporary abutment 610 via the screw 670 as best shown in FIG. 10E.

A further difference between the temporary abutment 610 (FIG. 10B) and the temporary abutment 510 (FIG. 9B) is that the temporary abutment 610 includes one informational marker location 662 with two informational markers 664 thereon as compared to the two informational marker locations 562 and the one informational marker 564 of the temporary abutment 510. The multiple informational markers 664 on the single informational marker location 662 results in the need for less informational marker locations 662, which, depending on the size of the temporary abutment 610, can be beneficial as the available real estate on a top surface 660 of the temporary abutment 610 is minimal due to, for example, an internal bore 640 of the temporary abutment 610.

Figure 10C:
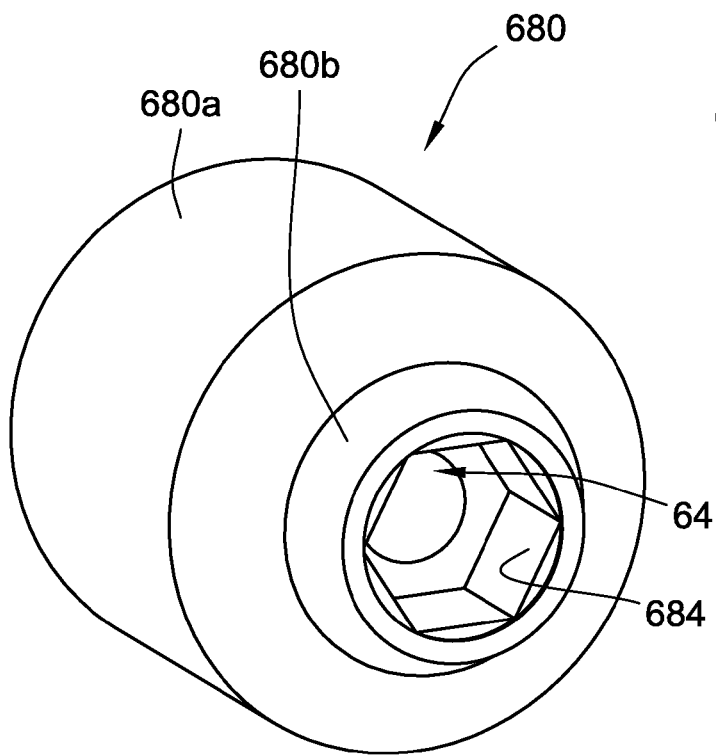
FIG. 10C is a perspective view of a temporary abutment cap of the prosthesis assembly of FIG. 10A.

Referring to FIG. 10C, unlike the single-piece temporary abutment caps 80, 280, 480, and 580, the temporary abutment cap 680 includes two pieces—a customizable portion 680a and a rigid portion 680b (best seen when separated in FIGS. 10A and 10D). The customizable portion 680a is similar to the additional material 282 of the temporary abutment cap 280 described above in reference to FIGS. 7A and 7B. That is, the customizable portion 680a can be sculpted into a custom shape for a particular patient and/or come preformed having an anatomical tooth shape. The rigid portion 680b is generally made from metal, such as, for example, titanium, and includes a non-rotational structure 684 and an internal bore 641. Alternatively, the rigid portion 680b can be made from a rigid plastic. The customizable portion 680a is permanently attached to the rigid portion 680b. However, in an alternative implementation, a kit of customizable portions 680a can be packaged with one or more rigid portions 680b such that a clinician selects one of the customizable portions 680a and then permanently attaches the selected one with a selected rigid portion 680b for attachment to the temporary abutment 610.

The temporary abutment cap 680 lacks a snap-fit type engagement to the temporary abutment 610. Rather, the temporary abutment cap 680 is coupled to the implant 120 and the temporary abutment 610 via the screw 670 as best shown in FIG. 10E.

The temporary abutment cap 680 includes the non-rotational structure 684 that is a six-sided hexagonal socket (FIG. 10C) as compared to the single flat surface of the non-rotational structure 84 of the temporary abutment cap 80 (FIG. 4A). However, the non-rotational structure 684 can be any of a variety of structures that corresponds with the non-rotational structure 634 to prevent relative rotation between the temporary abutment 610 and the temporary abutment cap 680.

Similar to the temporary abutment 580 (FIG. 9C), the temporary abutment cap 680 includes an aperture 683 (FIG. 10E) in a top portion thereof to provide access for the screw 670 to be installed after the temporary abutment cap 680 is installed on (e.g., non-rotationally mounted on) the temporary abutment 610. As best shown in FIG. 10E, a lip 677 of the screw 670 engages with an internal shoulder 642 of the internal bore 641 of the temporary abutment cap 680 to hold the prosthesis assembly 600 on the implant 120. After installation of the screw 670, a plug (not shown) of like material to the customizable portion 680a (e.g., plastic, acrylic, etc.) can be inserted through the aperture 683 and above the lip 677 of the screw 670 into the internal bore 641 to seal the aperture 683.

Referring to FIGS. 10D and 10E, a cross-sectional exploded view (FIG. 10D) and a cross-sectional assembled view (FIG. 10E) of the prosthesis assembly 600 and the dental implant 120 are shown for illustrating how the various components of the prosthesis assembly 600 are assembled and attached to the dental implant 120. The dental implant 120 is installed in a patient's jawbone (not shown) and then the temporary abutment 610 is non-rotationally attached to the implant 120 via a non-rotational feature 622 (FIG. 10B). The two-piece temporary abutment cap 680 is non-rotationally coupled to the temporary abutment 610 such that the non-rotational structure 634 (FIG. 10B) of the temporary abutment 610 engages the non-rotational structure 684 (FIG. 10C) of the temporary abutment cap 680. The screw 670 is then installed through the aperture 683 to hold the prosthesis assembly 600 on the implant 120.

Figure 11C:
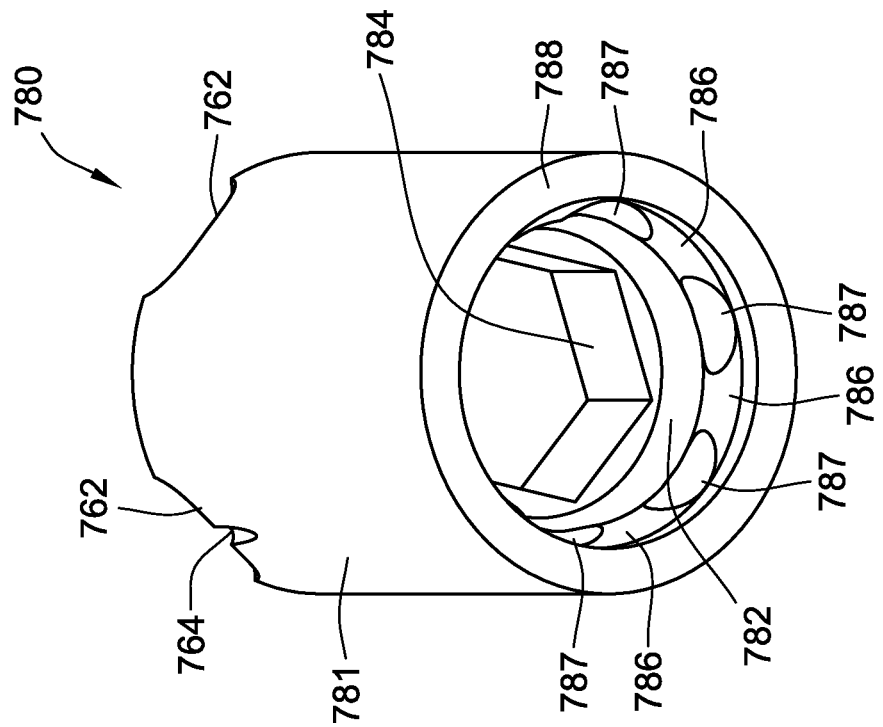
FIG. 11C is a perspective view of a temporary abutment cap of the prosthesis assembly of FIG. 11A.

Referring to FIGS. 11A to 11E, various views of components of an alternative prosthesis assembly 700 and the dental implant 120 are shown. As shown in FIG. 11A, the prosthesis assembly 700 includes a temporary abutment 710, a screw 770, a temporary abutment cap 780, and a temporary prosthesis 790, each of which is similar to, or the same as, corresponding components of the previously described prosthesis assemblies. In FIGS. 11A to 11E, each of the components and features is identified by a 700-series reference numeral, and those 700-series reference numerals correspond to like features of the various components and features of the previously described prosthesis assemblies. For example, reference numeral 734 is used to describe the non-rotational structure 734 (FIG. 11B), which is the same as, or similar to, the non-rotational structure 34 (FIG. 1A) and the non-rotational structure 534 (FIG. 9B). Additionally, reference numerals 720, 730, 740, 750, 755, 760, 781, 782, 787, and 788 are used in the figures to illustrate features that are the same as, or similar to, previously described features with reference numbers 20, 30, 40, 50, 55, 60, 81, 82, 487, and 88, respectively.

Figure 11B:
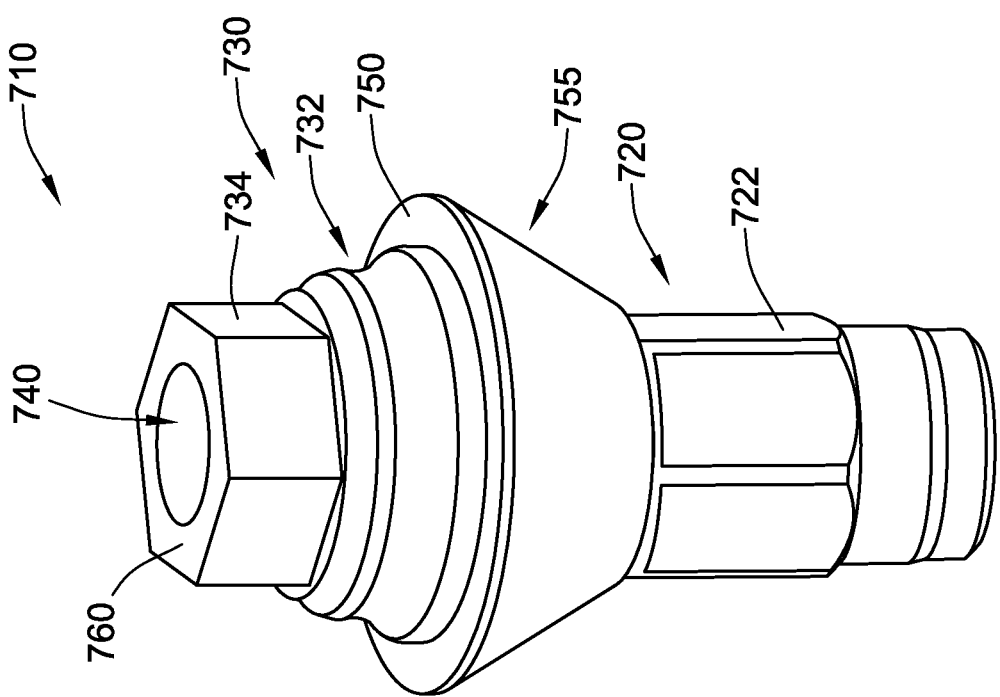
FIG. 11B is a perspective view of a temporary abutment of the prosthesis assembly of FIG. 11A.

Referring to FIG. 11B, the temporary abutment 710 generally includes all of the same features as the previous temporary abutments 10, 410, 510, 610, but lacks the informational marker locations 562 and the informational markers 564 of the temporary abutment 510. Rather, the temporary abutment cap 780 (FIG. 11C) of the prosthesis system 700 includes informational marker locations 762 and informational markers 764.

Further, a continuous retention groove 732 (FIG. 11B) of the temporary abutment 710 is positioned relatively higher (e.g., relatively further from the flange 50) as compared to the positioning of the continuous retention groove 532 of the temporary abutment 510 (best shown by comparing FIG. 9D with 11D). The continuous retention groove 732 (FIG. 11B) functions in the same, or similar, manner as the continuous retention grooves previously described herein in that the continuous retention groove 732 is configured to mate with one or more projections 786 of the temporary abutment cap 780 (FIG. 11C) in a snap-fit type engagement (shown in FIG. 11E).

Referring to FIG. 11C, the temporary abutment cap 780 includes the informational marker locations 762 and the informational markers 764. The information indicated by the informational marker locations 762 and/or the informational markers 764 (e.g., location and orientation of the underlying implant 120) can be gathered by scanning the temporary abutment cap 780 as opposed to scanning the temporary abutment 710.

Further, the temporary abutment cap 780 lacks the aperture 583 of the temporary abutment cap 580 in a similar fashion to the temporary abutment cap 80 lacking the aperture 583. Alternatively, the temporary abutment cap 780 can include an aperture (not shown) similar to the aperture 583 of the temporary abutment cap 580.

Figure 11E:
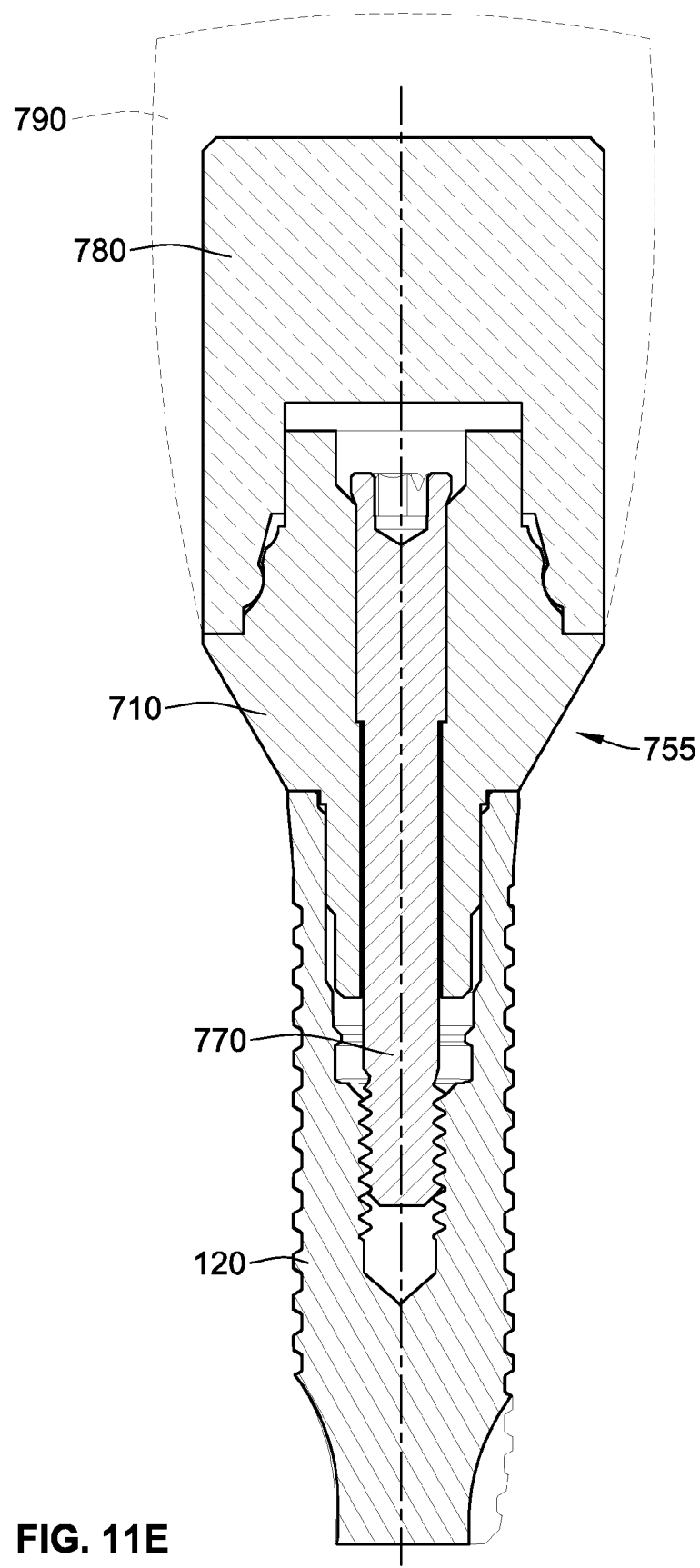
FIG. 11E is an assembled cross-sectional view of the prosthesis assembly and the implant of FIG. 11A.

Referring to FIGS. 11D and 11E, a cross-sectional exploded view (FIG. 11D) and a cross-sectional assembled view (FIG. 11E) of the prosthesis assembly 700 and the dental implant 120 are shown for illustrating how the various components of the prosthesis assembly 700 are assembled and attached to the dental implant 120. The dental implant 120 is installed in a patient's jawbone (not shown) and then the temporary abutment 710 is non-rotationally attached to the implant 120 via a non-rotational feature 722 (FIG. 11B) and the screw 770. The temporary abutment cap 780 is snap-fitted onto the temporary abutment 710 in a non-rotational manner such that the non-rotational structure 734 (FIG. 11B) of the temporary abutment 710 engages a non-rotational structure 784 (FIG. 11C) of the temporary abutment cap 780.

Optionally, a temporary prosthesis 790 can be coupled to the temporary abutment cap 780 in the same, or similar, manner as described herein in reference to the temporary prosthesis 90 being coupled to the temporary abutment 80 (FIGS. 6A and 6B). In such an alternative implementation, the informational marker locations 762 and/or the informational markers 764 can also mate with correspondingly shaped internal surfaces (not shown) of the temporary prosthesis 790 to provide for anti-rotation between the temporary abutment cap 780 and the temporary prosthesis 790. In the case that the temporary prosthesis 790 is not coupled to the temporary abutment cap 780, the temporary abutment cap 780 itself can have an anatomically shaped tooth structure and act as a temporary prosthesis.

Figure 12C:
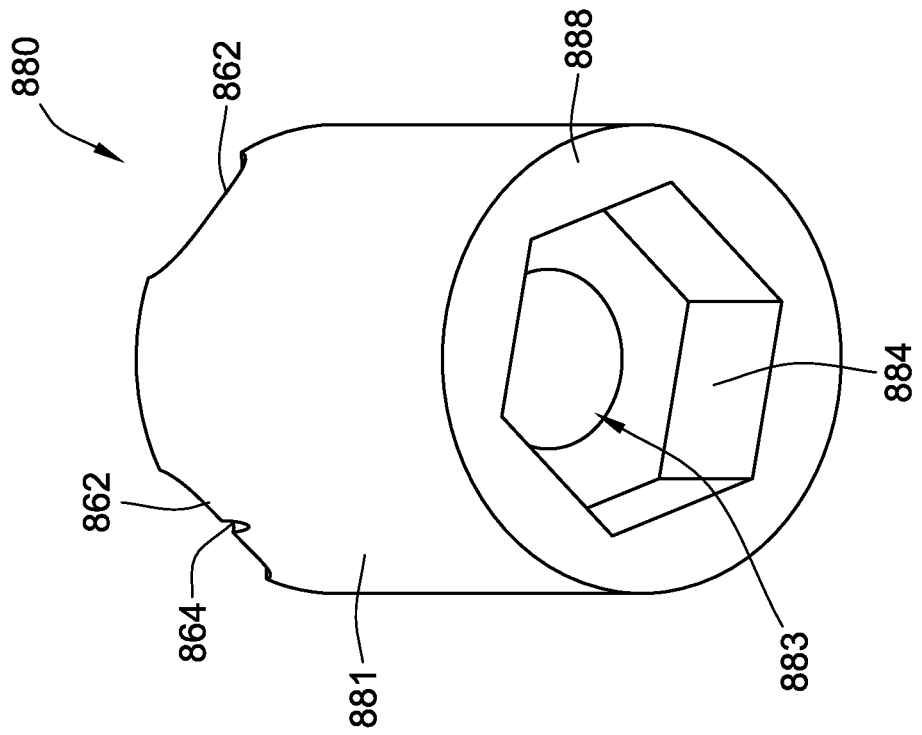
FIG. 12C is a perspective view of a temporary abutment cap of the prosthesis assembly of FIG. 12A.

Referring to FIGS. 12A to 12E, various views of components of an alternative prosthesis assembly 800 and the dental implant 120 are shown. As shown in FIG. 12A, the prosthesis assembly 800 includes a temporary abutment 810, a temporary abutment cap 880, a screw 870, and a temporary prosthesis 890, each of which is similar to, or the same as, corresponding components of the previously described prosthesis assemblies. In FIGS. 12A to 12E, each of the components and features is identified by a 800-series reference numeral, and those 800-series reference numerals correspond to like features of the various components and features of the previously described prosthesis assemblies. For example, reference numeral 834 is used to describe the non-rotational structure 834 (FIG. 12B), which is the same as, or similar to, the non-rotational structure 34 (FIG. 1A) and the non-rotational structure 534 (FIG. 9B). Additionally, reference numerals 820, 830, 850, 855, 860, 881, and 888 are used in the figures to illustrate features that are the same as, or similar to, previously described features with reference numbers 20, 30, 50, 55, 60, 81, and 88, respectively.

Figure 12B:
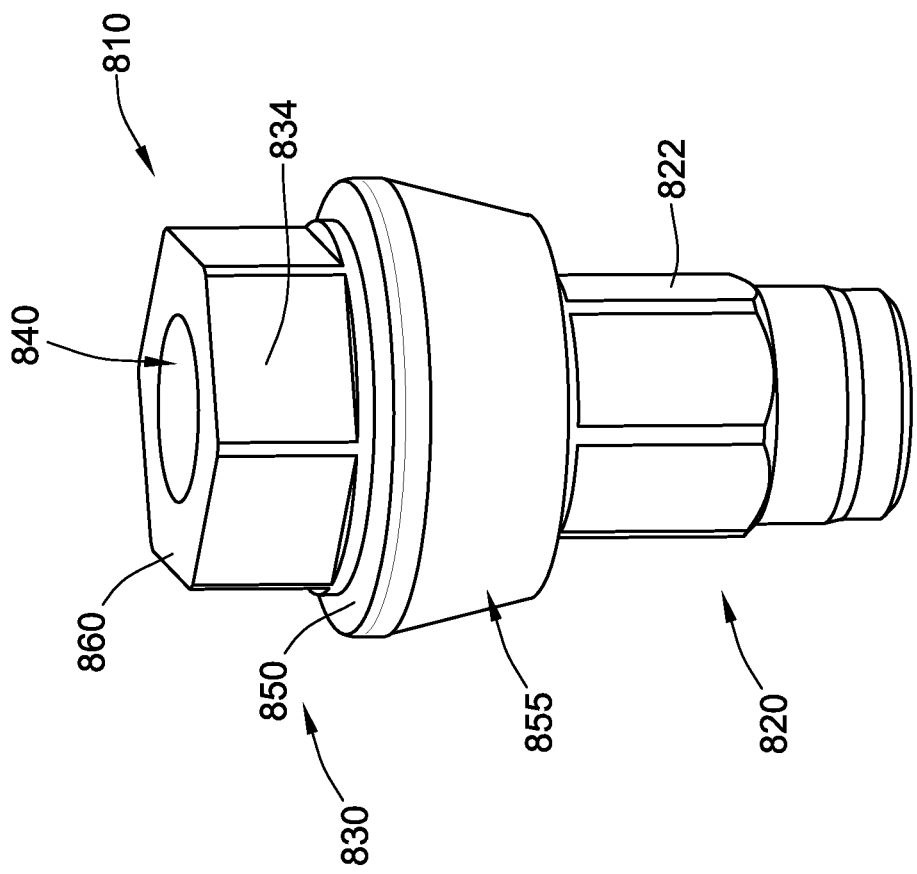
FIG. 12B is a perspective view of a temporary abutment of the prosthesis assembly of FIG. 12A.
Figure 12E:
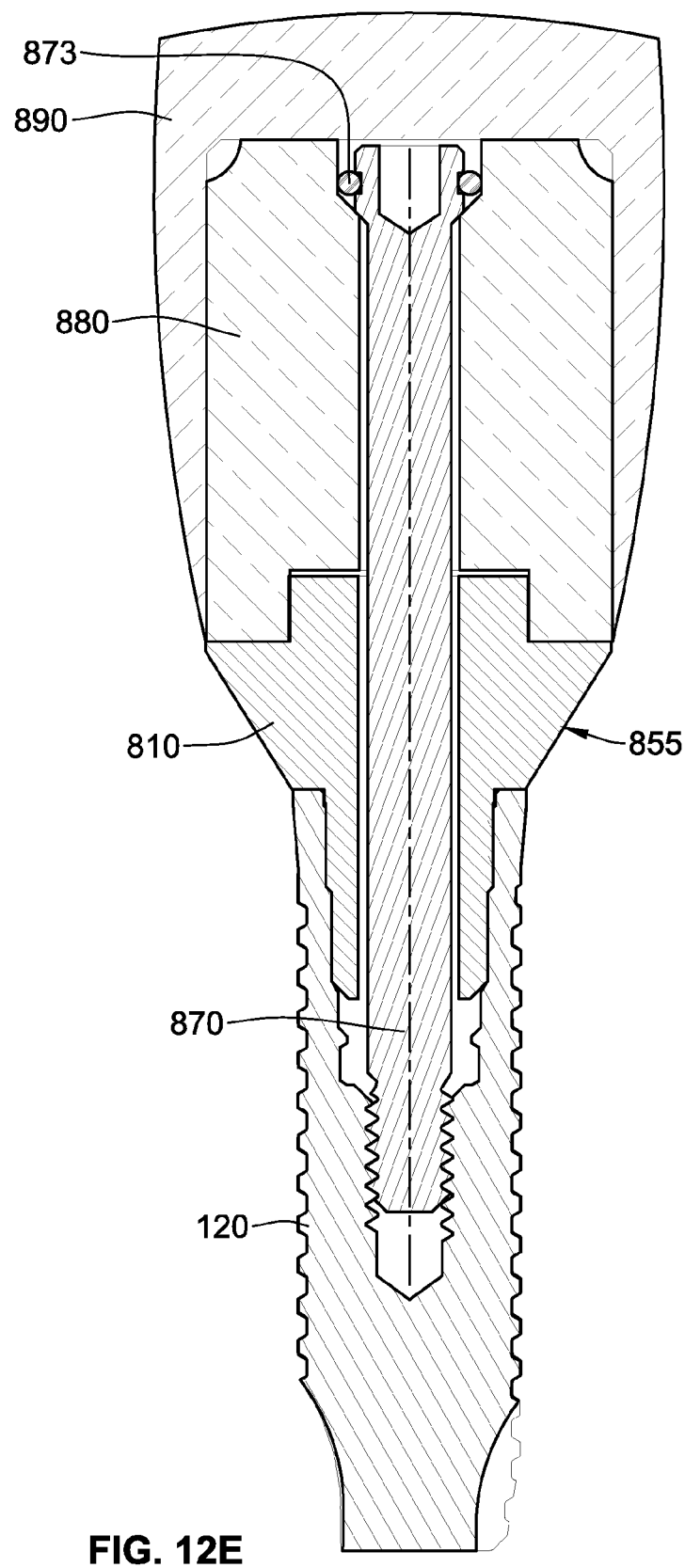
FIG. 12E is an assembled cross-sectional view of the prosthesis assembly and the implant of FIG. 12A.

Referring to FIG. 12B, the temporary abutment 810 generally includes all of the same features as the temporary abutments of the previous embodiments except the temporary abutment 810 lacks the continuous retention groove 732 (FIG. 11B) of the temporary abutment 710 such that the temporary abutment 810 does not couple with the temporary abutment cap 880 (FIG. 12C) in a snap-fit type engagement. Rather, the temporary abutment cap 880 (FIG. 12C) is held in a non-rotational fashion onto the temporary abutment 810 (FIG. 12B) via the screw 870, which is best shown in FIG. 12E. Accordingly, the temporary abutment cap 880 lacks the one or more projections 786 (FIG. 11C) of the temporary abutment cap 780 such that the temporary abutment cap 880 (FIG. 12C) does not couple with the temporary abutment 810 in a snap-fit type engagement.

Additionally, the temporary abutment cap 880 includes an aperture 883 that is similar to the aperture 583 of the temporary abutment cap 580 (FIG. 9C). The aperture 883 provides a path for the screw 870 to mate with the implant 120 through the internal bore 840 of the temporary abutment 810, thereby securing the temporary abutment cap 880 and the temporary abutment 810 onto the implant 120 in a non-rotational fashion, as best shown in FIG. 12E. The screw 870 (FIG. 12A) has a different head as compared to the screw 770. The head of the screw 870 includes a groove for mating with an O-ring 873 (FIG. 12E) that aids in sealing the internal bore 840 (FIG. 12B) of the temporary abutment 810.

Referring to FIGS. 12D and 12E, a cross-sectional exploded view (FIG. 12D) and a cross-sectional assembled view (FIG. 12E) of the prosthesis assembly 800 and the dental implant 120 are shown for illustrating how the various components of the prosthesis assembly 800 are assembled and attached to the dental implant 120. The dental implant 120 is installed in a patient's jawbone (not shown) and then the temporary abutment 810 is non-rotationally attached to the implant 120 via a non-rotational feature 822 (FIG. 12B). The temporary abutment cap 880 is coupled to the temporary abutment 810 in a non-rotational manner such that the non-rotational structure 834 (FIG. 12B) of the temporary abutment 810 engages a non-rotational structure 884 (FIG. 12C) of the temporary abutment cap 880. The screw 870 is inserted through the aperture 883 of the temporary abutment cap 880 and the internal bore 840 of the temporary abutment 810 and is threadingly coupled to the implant 120.

Optionally, a temporary prosthesis 890 is coupled to the temporary abutment cap 880 in the same, or similar, manner as described herein in reference to the temporary prosthesis 90 being coupled to the temporary abutment 80 (FIGS. 6A and 6B). In such an alternative implementation, the informational marker locations 862 and/or the informational markers 864 can also mate with correspondingly shaped internal surfaces (not shown) of the temporary prosthesis 890 to provide for anti-rotation between the temporary abutment cap 880 and the temporary prosthesis 890. In the case that the temporary prosthesis 890 is not coupled to the temporary abutment cap 880, the temporary abutment cap 880 itself can have an anatomically shaped tooth structure and act as a temporary prosthesis.

Figure 13E:
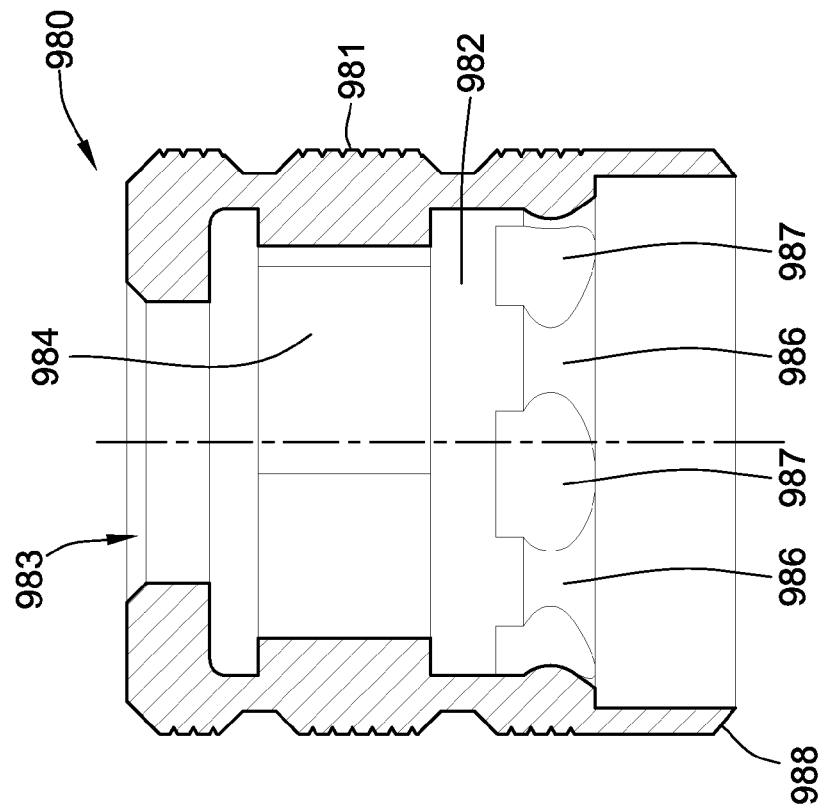
FIG. 13E is a cross-sectional view of the temporary abutment cap of FIG. 13D.

Referring to FIGS. 13A to 13H, various views of components of an alternative prosthesis assembly 900 and the dental implant 120 are shown. As shown in FIG. 13A, the prosthesis assembly 900 includes a temporary abutment 910, a temporary abutment cap 980, a screw 970, and a temporary prosthesis 990, each of which is similar to, or the same as, corresponding components of the previously described prosthesis assemblies. In FIGS. 13A to 13H, each of the components and features is identified by a 900-series reference numeral, and those 900-series reference numerals correspond to like features of the various components and features of the previously described prosthesis assemblies. For example, reference numeral 934 is used to describe the non-rotational structure 934 (FIGS. 13B and 13C), which is the same as, or similar to, the non-rotational structure 34 (FIG. 1A) and the non-rotational structure 534 (FIG. 9B). Additionally, reference numerals 932, 960, 962, 982, 986, 987, and 988 are used in the figures to illustrate features that are the same as, or similar to, previously described features with reference numbers 432, 60, 62, 82, 486, 487, and 88, respectively.

Referring to FIGS. 13B and 13C, the temporary abutment 910 generally includes all of the same features as the temporary abutments of the previous embodiments except an outer surface 955 of a flange 950 (e.g., portion of 910 that separates a subgingival region 920 and a supragingival region 930) of the temporary abutment 910 has a differently shaped contour for mating with a bottom end 988 (FIGS. 13D and 13E) of the temporary abutment cap 980. Rather than the bottom end 988 resting on a substantially flat upper portion of the flange 950 (as the bottom end 588 of the temporary abutment cap 580 rests on the upper portion of the flange 50 shown in FIG. 9E), the bottom end 988 abuts the flange 950 and forms a portion of the contour (best shown in FIG. 13G) that aids in forming a patient's gingival tissue during the healing process. Various other contours of the bottom end 988 and of the outer surface of the flange 950 can be used depending on the particular conditions present in the patient's mouth.

The temporary abutment 910 includes internal capture threads 943 (FIG. 13C) for threadably engaging with and capturing the screw 970. Such threads 943 are particularly useful for temporarily coupling the temporary abutment 910 with the screw 970 prior to installation of the same in a patient's mouth. As the screw 970 is rather small in size, its manipulation can be difficult. Thus, the temporary coupling between the screw 970 and the temporary abutment 910 prior to being installed in the patient's mouth prevents a clinician from having to perform the potentially difficult step of separately placing the screw 970 within an internal bore 940 for attachment with the implant 120 after the temporary abutment 910 is installed in the patient's mouth. While the threads 943 are only shown and described as being included in the temporary abutment 910, the same, or similar, threads can be included in any of the other temporary abutments of the present disclosure.

Figure 13D:
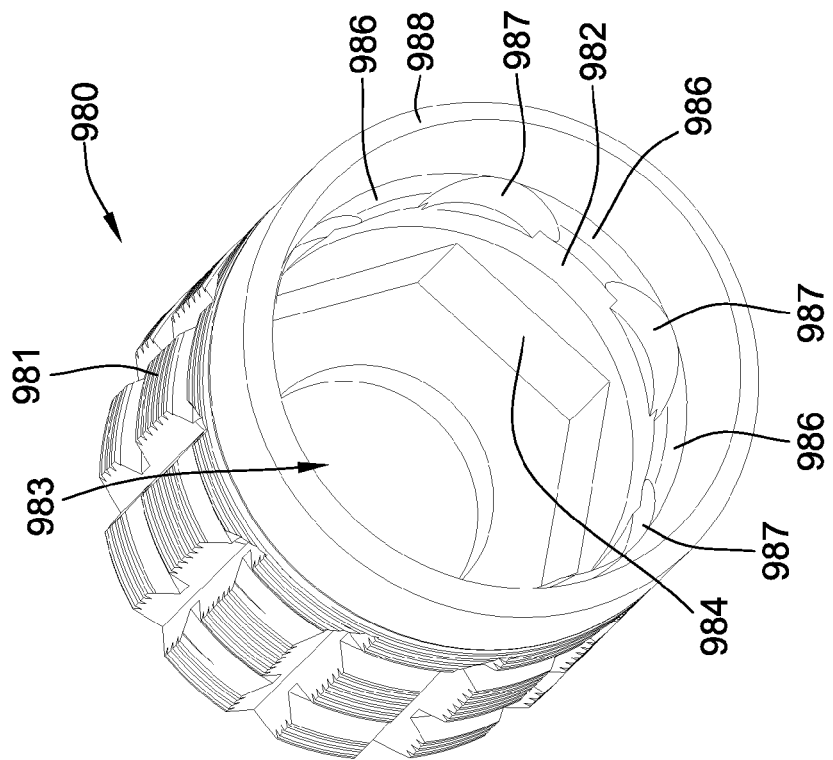
FIG. 13D is a perspective view of a temporary abutment cap of the prosthesis assembly of FIG. 13A.

Referring to FIGS. 13D and 13E, a generally cylindrical outer surface 981 of the temporary abutment cap 980 includes a plurality of grooves, notches, ribs, knurling, etc., or any combination thereof, instead of a substantially smooth generally cylindrical outer surface 581 (FIG. 9C) of the temporary abutment cap 580. The generally cylindrical outer surface 981 provides relatively more surface area as compared to the smooth generally cylindrical outer surface 581. The additional surface area of the generally cylindrical outer surface 981 results in a better adhesion or attachment between the temporary abutment cap 980 and the temporary prosthesis 990 (shown in FIGS. 13G and 13H). Alternatively to an inner bore of the temporary prosthesis 990 being formed to correspond to the contours of the generally cylindrical outer surface 981 of the temporary abutment cap 980 (best shown in FIGS. 13A and 13F), the temporary prosthesis 990 can be sufficiently pliable such that the inner bore of the temporary prosthesis 990 can be formed with one of a variety of shapes (e.g., substantially cylindrical and smooth) and slid over the temporary abutment cap 980.

Referring to FIGS. 13F to 13H, a cross-sectional exploded view (FIG. 13F), a cross-sectional assembled view (FIG. 13G), and a partial front and partial cross-sectional assembled view (FIG. 13H) of the prosthesis assembly 900 and the dental implant 120 are shown for illustrating how the various components of the prosthesis assembly 900 are assembled and attached to the dental implant 120. The dental implant 120 is installed in a patient's jawbone (not shown) and then the temporary abutment 910 is non-rotationally attached to the implant 120 via a non-rotational feature 922 (FIGS. 13B and 13C) and the screw 970. The temporary abutment cap 980 is snap-fitted onto the temporary abutment 910 in a non-rotational manner such that the non-rotational structure 934 (FIGS. 13B and 13C) of the temporary abutment 910 engages a non-rotational structure 984 (FIGS. 13D and 13E) of the temporary abutment cap 980. The temporary prosthesis 990 is coupled to the temporary abutment cap 980 in the same, or similar, manner as described herein in reference to the temporary prosthesis 90 being coupled to the temporary abutment 80 (FIGS. 6A and 6B) and such that the generally cylindrical outer surface 981 (FIGS. 13D and 13E) engages the internal bore of the temporary prosthesis 990. Alternatively, as the temporary abutment cap 980 includes an aperture 983 (FIGS. 13D and 13E), the temporary abutment cap 980 can be snap-fitted onto the temporary abutment 910 prior to the screw 970 being installed. Then, the screw 970 can be installed through the aperture 983, which is followed by the temporary prosthesis 990 being coupled to the temporary abutment cap 980.

Figure 14A:
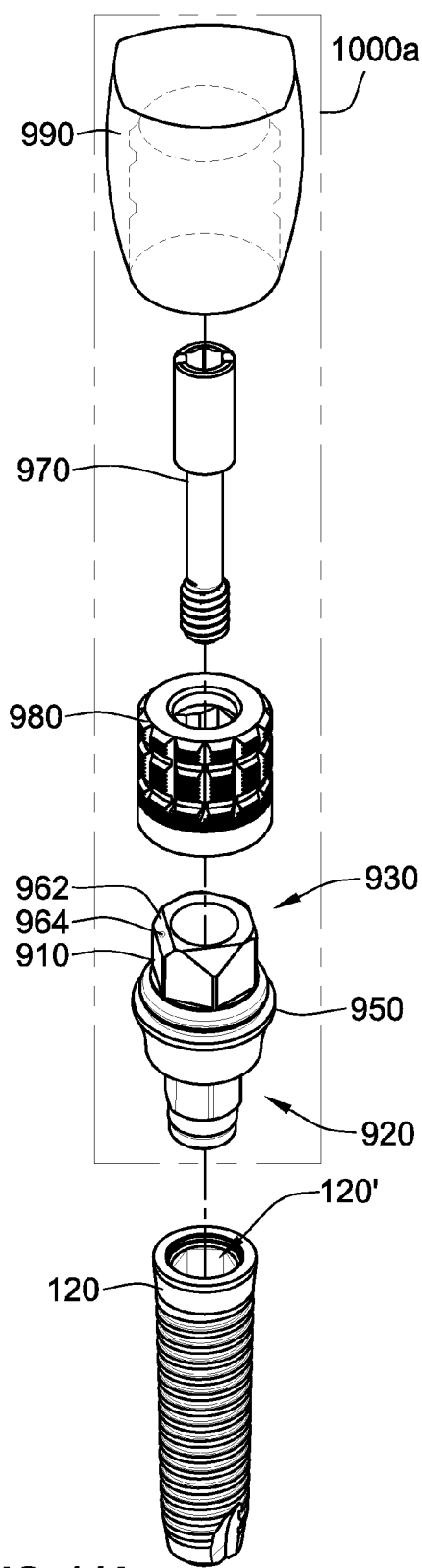
FIG. 14A is an exploded perspective view of a prosthesis assembly and a dental implant according to yet another alternative embodiment of the invention.
Figure 14B:
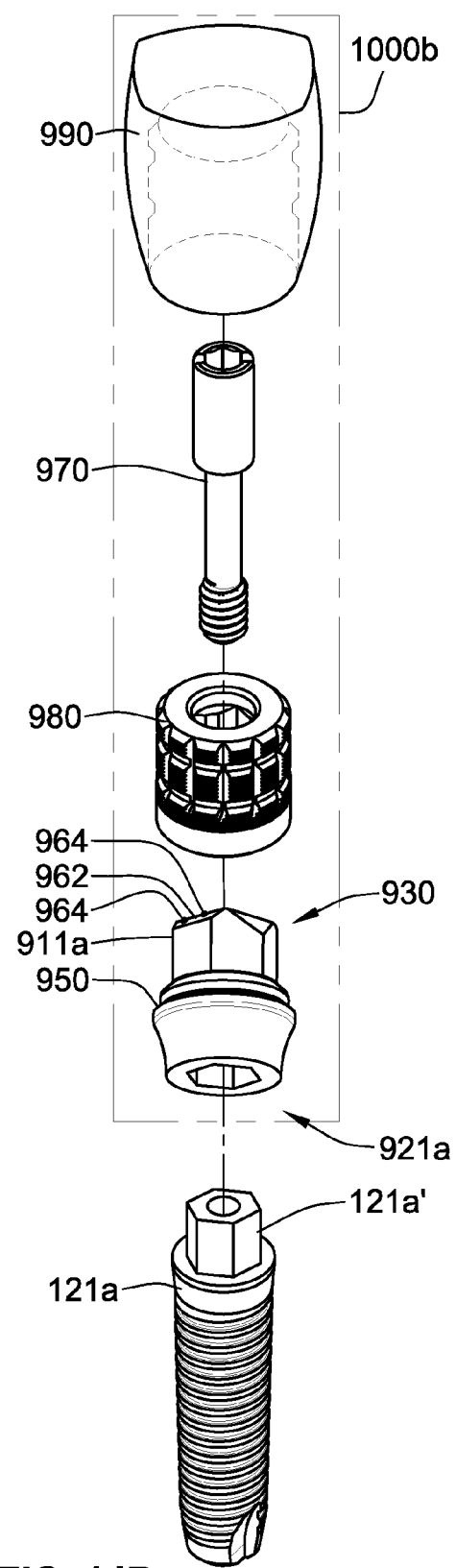
FIG. 14B is an exploded perspective view of a prosthesis assembly and a dental implant according to yet another alternative embodiment of the invention.
Figure 14C:
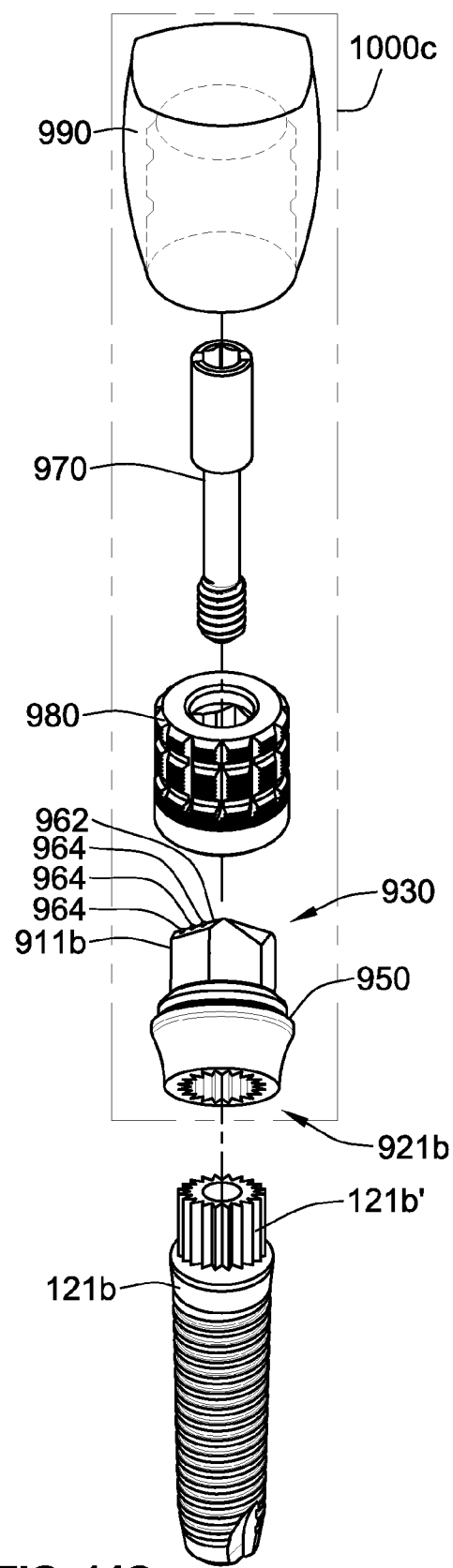
FIG. 14C is an exploded perspective view of a prosthesis assembly and a dental implant according to yet another alternative embodiment of the invention.

Referring to FIGS. 14A-C, three exploded prosthesis assemblies 1000a (FIG. 14A), 1000b (FIG. 14B), and 1000c (FIG. 14C) are shown for connection with three different dental implants 120 (FIG. 14A), 121a (FIG. 14B), and 121b (FIG. 14C), where like reference numbers are used for like components previously described herein. Each of the implants 120, 121a, and 121b includes a different anti-rotational feature for non-rotationally mating with a corresponding anti-rotational feature of a temporary abutment. As shown, the first implant 120 includes a female or socket-type hexagonal anti-rotational feature 120', the second implant 121a includes a male or boss-type hexagonal anti-rotational feature 121a', and the third implant 121b includes a male star anti-rotational feature 121b'. Various other types and shapes of anti-rotational features are contemplated for non-rotationally mating with corresponding anti-rotational features of a temporary abutment (e.g., temporary abutments 910, 911a, and 911b).

Each of the prosthesis assemblies 1000a, 1000b, and 1000c includes an identical temporary prosthesis 990, an identical screw 970, and an identical temporary abutment cap 980. However, while the temporary abutments 910, 911a, and 911b of each of the prosthesis assemblies 1000a, 1000b, and 1000c have identical external supragingival regions 930 and flanges 950, the subgingival regions 920, 921a, and 921b, and the internal arrangements of each of the temporary abutments 910, 921a, and 921b are different for non-rotationally mating with the different anti-rotational features 120', 121a', and 121b' of the implants 120, 121a, and 121b, respectively. Thus, depending on the type and/or manufacturer of the underlying implant, a temporary abutment (e.g., temporary abutments 910, 911a, 911b) can be selected (e.g., from a kit of temporary abutments) having a corresponding subgingival region (e.g., subgingival region 920, 921a, 921b) that non-rotationally couples therewith, but also includes a standard external supragingival region 930 and flange 950 that is configured to be coupled with standard components thereafter (e.g., the temporary prosthesis 990, the screw 970, and the temporary abutment cap 980).

While the supragingival regions 930 and the flanges 950 of the implants 120, 121a, and 121b are described as being identical, the number and/or orientation of the informational markers 964 and/or the informational marker locations 962 can be different. For example, as shown in FIG. 14A, the first temporary abutment 910 includes an informational marker location 962 with a single informational marker 964 thereon, which can, for example, indicate that the underlying implant 120 includes a female/socket-type hexagonal anti-rotational feature 120'. Similarly, as shown in FIG. 14B, the second temporary abutment 911a includes an informational marker location 962 with two informational markers 964 thereon, which can, for example, indicate that the underlying implant 121a includes a male/boss-type hexagonal anti-rotational feature 121a' and, as shown in FIG. 14C, the third temporary abutment 911b includes an informational marker location 962 with three informational markers 964 thereon, which can, for example, indicate that the underlying implant 121b includes a male/boss-type star anti-rotational feature 121b'. The differences in the informational markers 964 of the three temporary abutments 910, 911a, and 911b may alternatively and/or additionally indicate a different line of implants for a single manufacturer, or a different line of different implant manufacturers. Of course, additional informational markers 964 and/or additional informational marker locations 962 on the temporary abutments 910, 911a, and 911b could indicate other aspects of the underlying implants 120, 121a, and 121b (e.g., diameter, anti-rotational feature orientation, location of the table surface, etc.).

While some of the anti-rotational features are shown in the figures and described herein as being a male or boss anti-rotational feature and others are shown in the figures and described herein as being female or socket anti-rotational features, it is contemplated that the male-female anti-rotation features can be swapped on different components as needed.

While the temporary abutments 10, 10', 410, 510, 610, 710, 810, and 910 are shown and described herein as being temporary (i.e., not permanent), the temporary abutments 10, 10', 410, 510, 610, 710, 810, and 910 can, in fact, be permanent abutments that are designed to be coupled with a corresponding permanent prosthesis and/or crown. In such an alternative implementation of the disclosed concepts, the permanent prosthesis is developed and designed to be coupled with the temporary abutment 10, 10', 410, 510, 610, 710, 810, and 910 instead of a separate permanent patient specific abutment.

While the temporary abutments 10, 10', 410, 510, 610, 710, 810, and 910 are shown and described herein as having a subgingival region, a supragingival region and a flange therebetween, any portion of the flange and/or of the supragingival region can be placed subgingival (e.g., below the gingival tissue) for a given installation. Similarly, any portion of the flange and/or of the subgingival region can be placed supragingival (e.g., above the gingival tissue) for a given installation. Moreover, the supragingival regions described herein can be referred to as a post region that is partially subgingival and/or partially supragingival. That is, in some instances, the terms supragingival and post can be used interchangeably when referring to the various portions of the temporary abutments described herein.

All of the temporary prostheses 90, 490, 590, 790, 890, and 990 described herein can be cemented to the respective temporary abutment caps 80, 480, 580, 780, 880, and 980 described herein via normal dental cement.

In the various embodiments of FIGS. 1A to 14C, the temporary abutments, the temporary abutment caps, and the temporary prostheses have several physical and functional differences. However, each embodiment is useful in that it provides an aesthetically pleasing temporary prosthesis that can be installed immediately after implant installation and that can be used to form the adjacent gingival tissue into a desired shape as it heals following surgery. Additionally, the temporary abutment caps and temporary prostheses (which are typically held together via dental cement) can be easily removed from the temporary abutment to reveal the informational markers thereon that provide information about the dimensions and/or orientation of the underlying implant and/or of the temporary abutment itself (or the temporary abutment cap may include the information markers such that removal is not required). Knowing this information regarding the dimensions and/or orientation of the underlying implant and/or the temporary abutment and knowing the actual healed shape of the gingival tissue (or a predicted healed shape, see FIG. 17 below) permits for the design and manufacture of a permanent patient-specific abutment prior to the patient's gingival tissue healing. It also provides for the option of the design and manufacture of the final permanent prosthesis that will fit on the patient-specific abutment.

Regarding one exemplary use of the informational markers disclosed herein (e.g., informational markers 64), an implant line may come in two diameters at the upper table surface (e.g., 4 mm and 5 mm). For each of those two implants, there may be four different types of temporary abutments that can be used. For example, there could be two different overall heights to the temporary abutment (e.g., 8 mm, and 10 mm). And, for each of those two temporary abutments having different heights, there could be two different emergence profiles (e.g., outer surface 55) leading away from the implant to the flange (e.g., flange 50) of the temporary abutment. As such, there are eight potential temporary abutments with different shapes and dimensions. If there are three informational marker locations (e.g., informational marker locations 62) on each of those temporary abutments at which an informational marker may or may not be present, that provides for eight combinations, assuming a binary-type marking system is used. Hence, each of the eight potential temporary abutments would have a unique marking scheme such that the exact temporary abutment can be easily identified by simple inspection (e.g., via scanning) of the informational markers. And, by knowing the exact temporary abutment, important information concerning the implant, such as its table's diameter (i.e., 4 mm or 5 mm) and the exact location of the implant's table (and its angular orientation), is also known. Additionally, by providing another informational marker (or a second type of informational marker location, such as a triangular or rectangular chamfer or flat) on the temporary abutment, the angular orientation of the implant's anti-rotational feature is known, which is also important for developing the permanent patient-specific abutment. In all of these embodiments, the computer system that receives and uses the scan data for developing the patient-specific abutment preferably includes a simple look-up table that, based on the information markers revealed in the scan, indicates the exact temporary abutment mounted on the implant. Then, the implant's information can be modeled in the computer system as well. This is, of course, one exemplary embodiment and more or less information markers may be needed depending on the type of implant system. As another example, the type of implant (e.g., its table's diameter and/or its type of anti-rotational connection) can be identified via informational markers present on the head of the screw that holds the temporary abutment to the implant. And, the informational markers on the temporary abutment indicate information regarding the temporary abutment (e.g., its emergence profile shape, its overall height, its flange diameter, etc.).

Methods of Developing Permanent Patient-Specific Abutments and Tooth Prostheses

Figure 15:
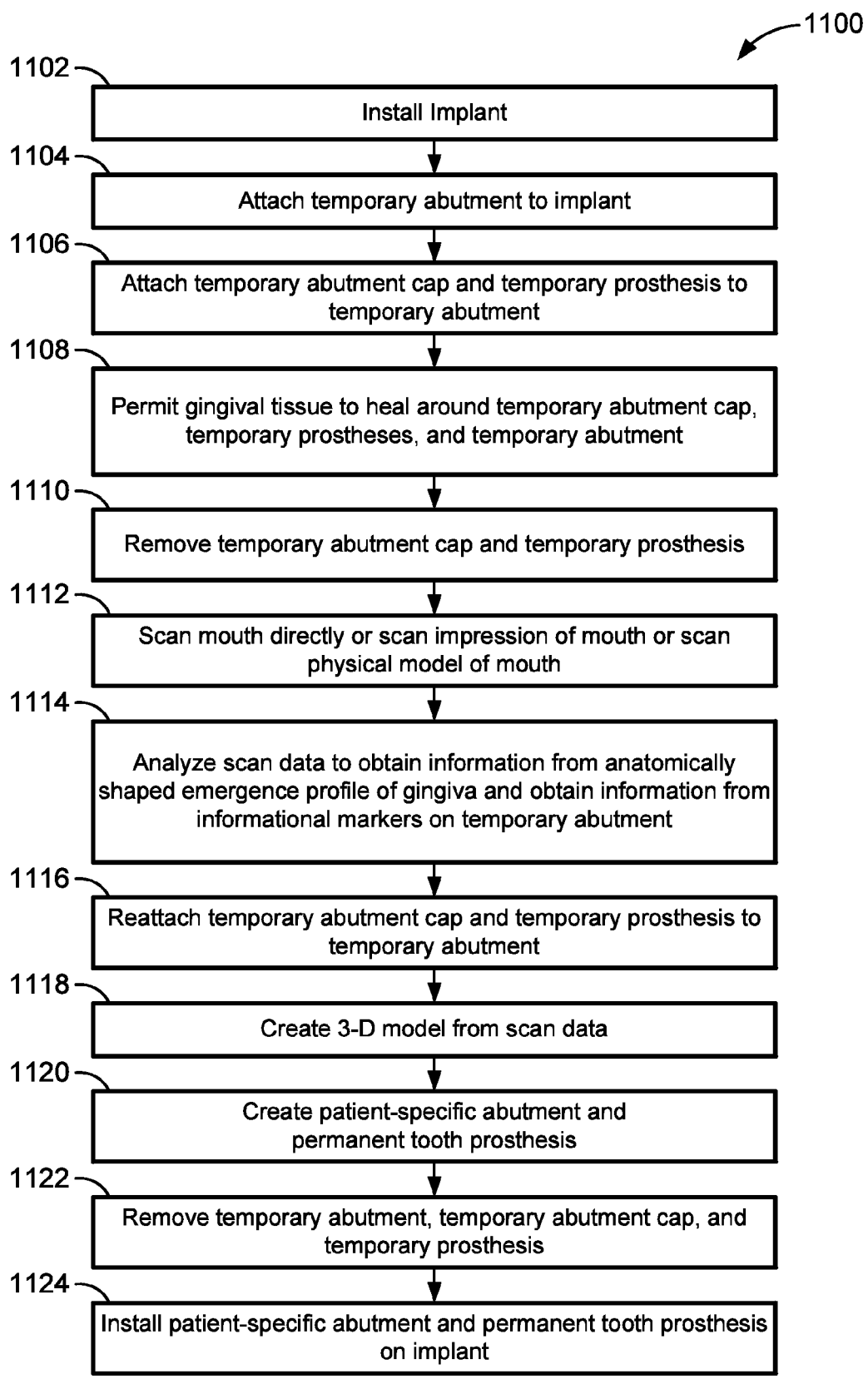
FIG. 15 is a flow chart of a method for making a permanent patient-specific abutment and permanent tooth prosthesis using the prosthesis assembly components of the present invention.

Referring to FIG. 15, a method (1100) of developing a permanent patient-specific abutment ("PSA") and tooth prosthesis typically begins with the installation (1102) of a dental implant (e.g., dental implant 120 shown in FIG. 6A) in the jawbone of a patient. A temporary abutment (e.g., temporary abutment 10, 10', 410, 510, 610, 710, 810, 910) is then installed (1104) in a non-rotational fashion on the implant directly after the implant is installed in the patient's jawbone. The temporary abutment is attached via complementary non-rotational features on the temporary abutment and on the implant. The temporary abutment is axially held in contact with the implant via a fastening device (e.g., fastening device 70, 470, 570, 670, 770, 870, 970) that threadably engages threads in an interior bore of the implant.

A temporary abutment cap (e.g., temporary abutment cap 80, 280, 480, 580, 680, 780, 880, 980) is attached (1106) to the temporary abutment in a removable fashion, such as, for example, via a snap-fit connection. Thereafter, or prior to the temporary abutment cap being attached, a temporary prosthesis, shaped to approximate an anatomically shaped tooth, is attached (1106) to the temporary abutment via the temporary abutment cap. The temporary prosthesis is generally affixed to the temporary abutment cap in a non-removable fashion (e.g., using acrylic, cement, bonding, etc.).

After the temporary components are installed (1104-1106), the patient's gingival tissue is permitted to heal therearound (1108). After the gingival tissue is healed, the temporary abutment cap and the temporary prosthesis are removed from the temporary abutment (1110). Removal of the temporary abutment cap and temporary prosthesis reveals a top surface of the underlying temporary abutment that includes one or more informational markers (e.g., informational markers 64). Additionally, an emergence profile of the healed gingival tissue is exposed, which may be in a non-round anatomical shape.

Both the temporary abutment and the surrounding gingival tissue are scanned using one or more scanning techniques directly in the patient's mouth (1112). Alternatively, an impression of at least the area of the patient's mouth including the temporary abutment is taken and scanned (1112). That is, the impression of the mouth can be scanned instead of scanning directly in the patient's mouth. In a third alternative, a physical model of the patient's dental conditions including the temporary abutment is made from the impression. Then the physical model can be scanned (1112) instead of scanning directly in the mouth or scanning the impression. In any event, scanning directly in the mouth is the preferred method.

Scan data is generated from the scanning that is analyzed via one or more processors and/or computers to obtain information (1114). Specifically, information related to and/or representative of the anatomically shaped emergence profile of the patient's gingival tissue surrounding the temporary abutment and information related to and/or representative of the informational markers on the temporary abutment (1114) is obtained. Additionally, information related to and/or representative of the patient's dental anatomy (e.g., adjacent teeth) surrounding the temporary abutment can be obtained. Further, information related to and/or representative of the geometrical relationships between the patient's emergence profile, the informational markers, and/or the patient's dental anatomy can be obtained.

After the scanning, the temporary abutment cap and the temporary prosthesis are reattached to the temporary abutment (1116). A three-dimensional virtual model of at least a portion of the patient's mouth/dental conditions is created from the scan data (1118). The three-dimensional virtual model includes a virtual model of at least a portion of the patient's gingiva tissue, the patient's teeth, and the temporary abutment. Using one or more software or computer programs in conjunction with determined parameters based on the scanned informational markers, the three-dimensional virtual model can be modified to remove the temporary abutment, thereby providing/illustrating the location and orientation of the underlying implant and its relative position to the patient's gingival tissue. One non-limiting example is CAD-CAM dental software and scanning software available from 3Shape A/S located in Copenhagen, Denmark.

Using the three-dimensional model, a patient-specific abutment and permanent tooth prosthesis is virtually designed (1120). The designed patient-specific abutment and permanent tooth prosthesis can be created by, for example, sending data to a milling machine and/or a rapid prototype machine that is configured to create a physical patient-specific abutment (which would be attached to the implant) and a physical-permanent tooth prosthesis (which would be attached to the physical patient-specific abutment) that are both eventually installed in the mouth of the patient. After the patient-specific abutment and the permanent tooth prosthesis are created, the temporary abutment, the temporary abutment cap, and the temporary prosthesis are removed from the patient's mouth to expose the underlying dental implant (1122). The method is completed by installing the patient-specific abutment and the permanent tooth prosthesis on the dental implant as is known in the art (1124).

Figure 16:
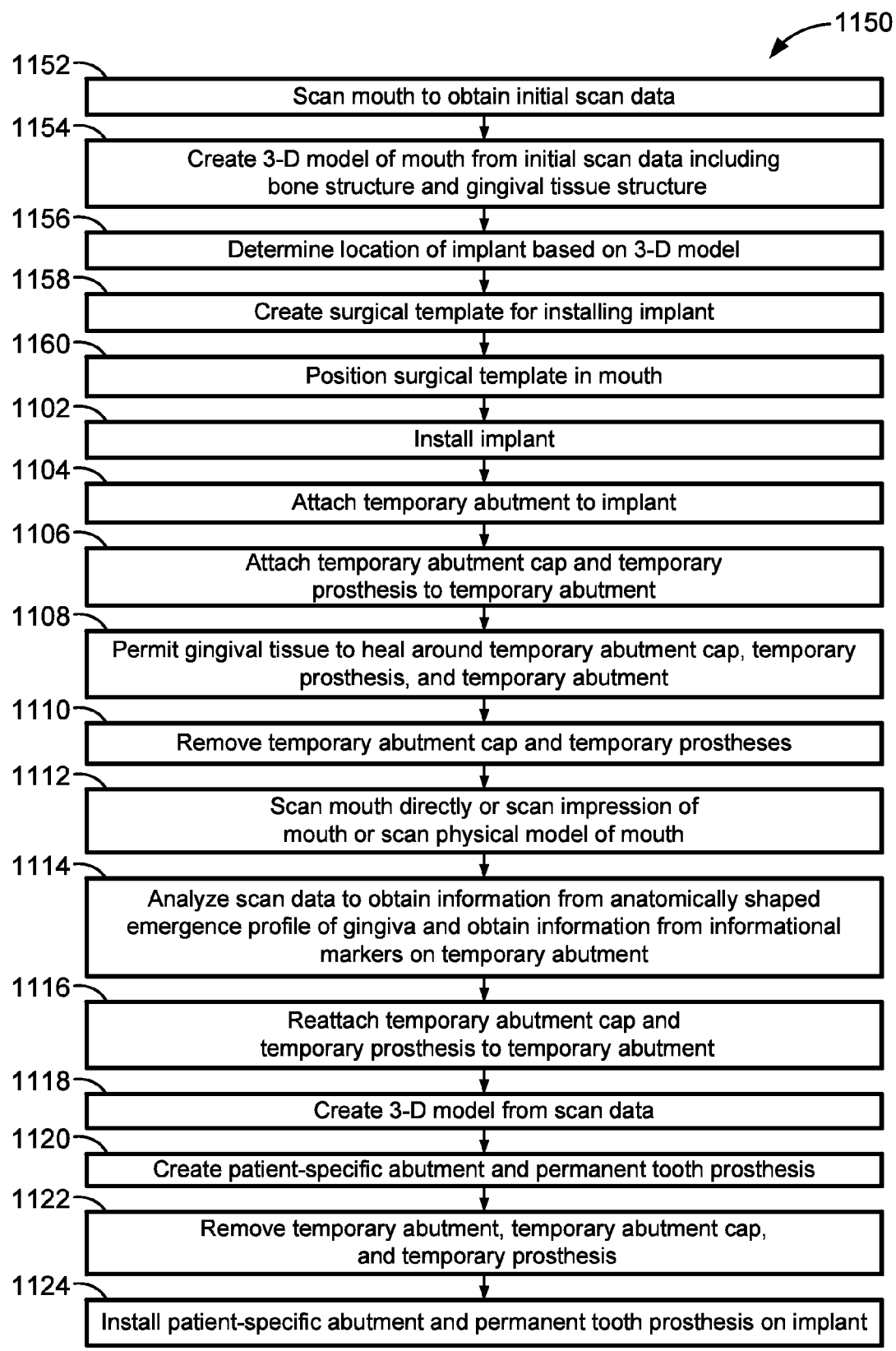
FIG. 16 is a flow chart of a method for making a permanent patient-specific abutment and permanent tooth prosthesis including a method for preparing to install an implant.

Prior to the dental implant being installed in the patient's mouth, several additional steps can be taken to aid in the installation process. Referring to FIG. 16, a method (1150) of creating and installing a patient-specific abutment and a permanent tooth prosthesis including preparation steps is shown. The preparation steps typically begin by scanning the patient's mouth to obtain initial scan data (1152). The scanning includes two types of scans to obtain data related to and/or representative of different types of tissues. A first soft tissue scan includes a scan configured to obtain data representative of soft tissue in the patient's mouth, such as, for example, the gingival tissue. A second hard tissue or bone scan includes a scan configured to obtain data representative of hard tissue or bone or teeth in the patient's mouth, such as, for example, the patient's jawbone and teeth. Additional details on creating accurate bone and soft-tissue digital dental models can be found in US Patent Application Publication No. 2011/0129792, entitled "Method of Creating an Accurate Bone and Soft-Tissue Digital Dental Model," which is hereby incorporated by reference herein in its entirety.

After obtaining the initial scan data, a three-dimensional model of the patient's mouth is created including the patient's bone structure and gingival tissue structure (1154). From the three-dimensional model, using one or more processors and/or computers, a desired location and orientation (e.g., pitch, yaw, depth) of a dental implant to be installed in the patient's mouth is determined (1156). The determined location can be selected or determined based on a number of different variables, such as, for example, the location, position, and orientation of the teeth adjacent to the proposed implant site, the location of nerves or the sinus cavity, and/or the composition and structure of the patient's jawbone. Additional details on surgical guides and methods for using and making the same can be found in U.S. Patent Application Publication 2009/0130630, application Ser. No. 12/271,517, filed Nov. 14, 2008, entitled, "Components for Use with a Surgical Guide for Dental Implant Replacement" and in U.S. Patent Application Publication 2009/0263764, application Ser. No. 12/425,202, filed Apr. 16, 2009, now allowed, entitled, "Method for Pre-Operative Visualization of Instrumentation Used with a Surgical Guide for Dental Implant Placement," each of which is hereby incorporated by reference in its entirety.

After the location is determined, a surgical template for installing the implant is created (1158). The surgical template is used to guide and/or aid a surgeon in drilling an aperture in the patient's mouth to receive the implant in the predetermined desired location. The preparation steps typically conclude with the positioning of the surgical guide in the patient's mouth prior to installation of the implant (1160). The rest of the steps directed to creating and installing the patient-specific abutment and the permanent tooth prosthesis (1102-1124) in the method (1150) are the same as previous described in reference to FIG. 15.

Figure 17:
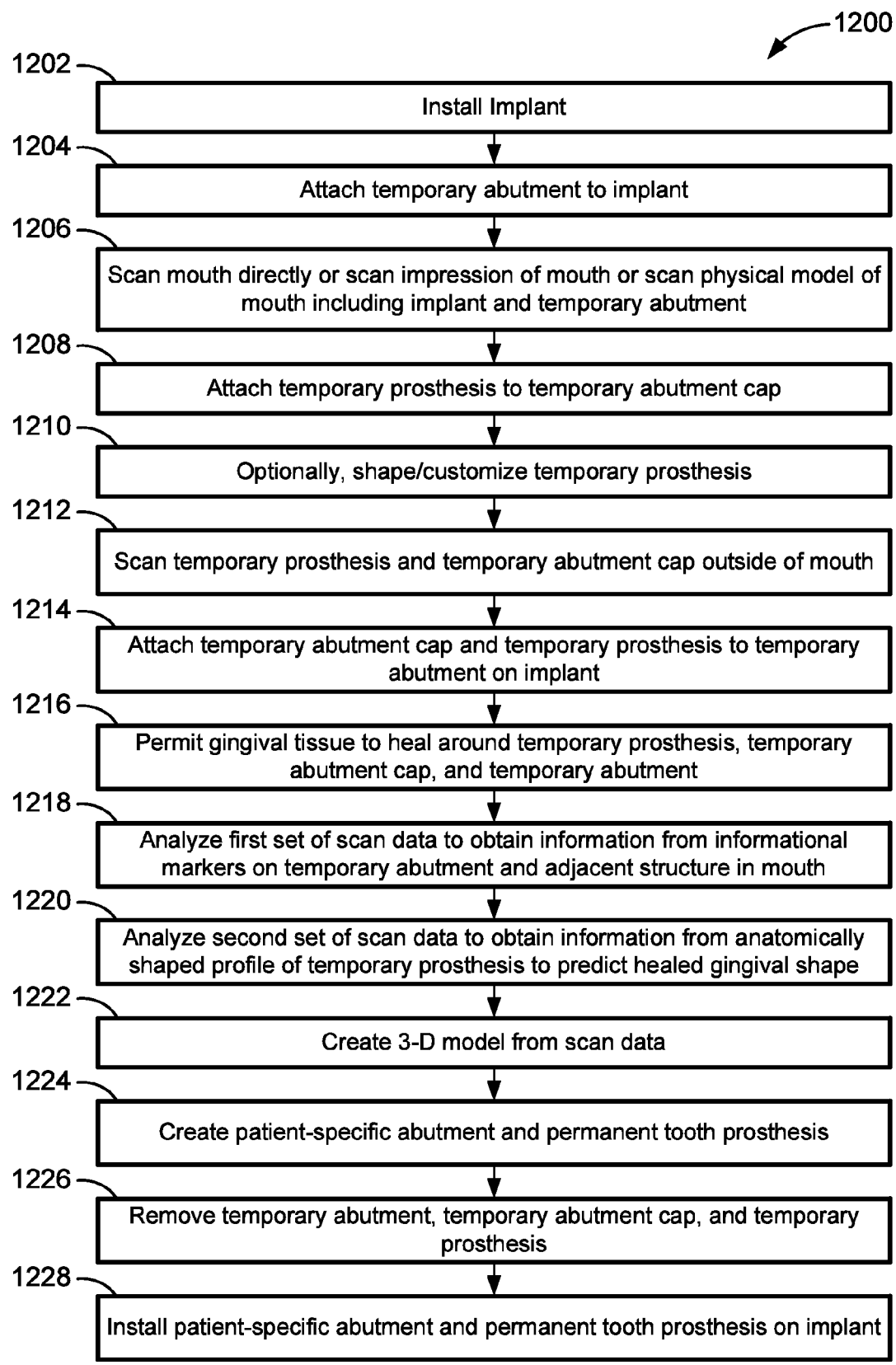
FIG. 17 is a flow chart of a method for making a permanent patient-specific abutment and permanent tooth prosthesis using the prosthesis assembly components of the present invention.

Referring to FIG. 17, an alternative method (1200) of developing a permanent patient-specific abutment ("PSA") and tooth prosthesis is described. A primary difference between the method (1200) and the methods (1100) and (1150) of FIGS. 15 and 16 is the timing of the scanning of the patient's mouth. As described below, in the method (1200), the patient's mouth is scanned at the same time that the implant is installed instead of waiting to permit gingival healing to occur prior to removing components and then scanning Such a method (1200) can eliminate at least one visit to the doctor's office during the overall installation of the PSA and tooth prosthesis. More specifically, in some instances, the saved doctor's office visit prevents additional disruption of gingival tissue during the healing phase as the temporary abutment cap and temporary prosthesis do not have to be removed for scanning the patient's mouth a second time to capture the gingival contours.

The method (1200) typically begins with the installation (1202) of a dental implant (e.g., dental implant 120 shown in FIG. 6A) in the jawbone of a patient. A temporary abutment (e.g., temporary abutment 10, 10', 410, 510, 610, 710, 810, 910) is then installed (1204) in a non-rotational fashion on the implant directly after the implant is installed in the patient's jawbone. The temporary abutment is attached via complementary non-rotational features on the temporary abutment and on the implant. The temporary abutment is axially held in contact with the implant via a fastening device (e.g., screw 70, 470, 570, 670, 770, 870, and 970) that threadably engages threads in an interior bore of the implant.

After the attachment of the temporary abutment, a top surface thereof, that includes one or more informational markers (e.g., informational markers 64), is exposed in the patient's mouth. The temporary abutment and at least a portion of the surrounding dental features (e.g., adjacent teeth and/or adjacent gingival tissue) are scanned using one or more scanning techniques directly in the patient's mouth (1206). Alternatively, an impression of at least the area of the patient's mouth including the temporary abutment is taken and scanned (1206). That is, the impression of the mouth can be scanned instead of scanning directly in the patient's mouth. In a third alternative, a physical model of the patient's dental conditions including the temporary abutment is made from the impression. Then the physical model can be scanned (1206) instead of scanning directly in the mouth or scanning the impression. In any event, scanning in the mouth is the preferred method.

A temporary prosthesis (e.g., temporary prosthesis 490, 590, 790, 890, 990), shaped to approximate an anatomically shaped tooth, is attached to a temporary abutment cap (e.g., temporary abutment cap 80, 280, 480, 580, 680, 780, 880, 980) outside of the patient's mouth (1208). The temporary prosthesis is generally affixed to the temporary abutment cap in a non-removable fashion (e.g., using acrylic, cement, bonding, etc.), thereby forming a subassembly; however, in some implementations of the present aspects, the temporary prosthesis is not permanently affixed to the temporary abutment cap until the temporary abutment cap is attached to the temporary abutment in the patient's mouth via a screw. Prior to and/or after attaching the temporary prosthesis to the temporary abutment cap, the temporary prosthesis can be shaped and/or customized (1210), by, for example, a clinician.

After the temporary prosthesis and the temporary abutment cap are attached and the final shape of the temporary prosthesis has been developed, the subassembly is scanned outside of the patient's mouth using one or more scanning techniques (1212). The subassembly (e.g., the temporary prosthesis and the temporary abutment cap) is then attached (1214) to the temporary abutment in a removable fashion, such as, for example, via a snap-fit connection and/or a screw-type connection. After the temporary components are installed (1214) and the scanning has taken place (1212), the patient's gingival tissue is permitted to heal therearound (1216).

Alternatively to scanning the subassembly outside of the patient's mouth, if the opening in the patient's gingiva is large enough—such that all the contours of the subassembly are viewable/scanable when attached to the temporary abutment—the scanning of the subassembly can occur in the mouth instead of outside the mouth. Such a scanning of the subassembly in the patient's mouth can occur immediately after installation and could include information representative of one or more surrounding features of the patient's mouth (e.g., adjacent teeth, gingival tissue, etc.).

Scan data is generated from both of the scans that is analyzed via one or more processors and/or computers to obtain information (1218 and 1220). The analysis of the scan data can occur immediately after the scans are taken and before the gingival tissue is permitted to heal. Of course, the analysis of the scan data can alternatively occur at any time after the gingival tissue is initially permitted to heal. Specifically, the first set of scan data is analyzed to obtain information related to and/or representative of the temporary abutment and information related to and/or representative of the informational markers on the temporary abutment (1218). Additionally, information related to and/or representative of the patient's dental anatomy (e.g., adjacent teeth) surrounding the temporary abutment can be obtained from the first set of scan data. Further, the second set of scan data is analyzed to obtain information related to and/or representative of the temporary prosthesis and/or the temporary abutment cap (1220). Specifically, information, such as, for example, the anatomical contours of the temporary prosthesis can be obtained. Such contours of the temporary prosthesis can be used to predict the contours of the patient's gingiva after being permitted to heal (1216).

After the scan data is acquired and analyzed, the first and the second sets of data are merged to create a three-dimensional virtual model of at least a portion of the patient's mouth/dental conditions (1222). The merging of the data sets includes aligning the two data sets, which can be accomplished many ways. For example, corresponding markers (e.g., notches, grooves, lines, dots, pimple, dimple, etc.) positioned on, for example, a top side of the flange of the temporary abutment and on, for example, a bottom or under/inner surface of the temporary abutment cap can be captured during the scanning such that the markers can be used in conjunction with one or more software or computer programs to align (e.g., rotational align about the z-axis) the two sets of data with respect to each other. For another example, the two sets of data can be aligned using one or more software or computer programs that evaluate the positions of the non-rotational features of the temporary abutment and the temporary abutment cap. For a third example, the subassembly can be installed on the temporary abutment and a third scan is taken of the subassembly and surrounding area in the patient's mouth. The third scan produces a third set of scan data that can be used by one or more software or computer programs to align the first and the second data sets.

The three-dimensional virtual model includes a virtual model of at least a portion of the patient's gingiva tissue (based on one or both sets of the scan data), the patient's teeth, and the temporary abutment. Using one or more software or computer programs in conjunction with determined parameters based on the scanned informational markers, the three-dimensional virtual model can be modified to remove the temporary abutment, thereby providing/illustrating the location and orientation of the underlying implant and its relative position to the patient's gingival tissue. Further, using one or more software or computer programs, the three-dimensional virtual model is designed such that the depicted emergence profile of the patient's gingival tissue adjacent to the implantation site is based on the contours of the temporary prosthesis and/or the temporary abutment cap. That is, the depicted emergence profile in the three-dimensional virtual model is a predicted emergence profile and is not based on scan data from a scan of an actual (e.g., healed) emergence profile of the patient's gingival tissue because the scan in the mouth was taken prior to gingival healing.

Using the three-dimensional model, a patient-specific abutment and permanent tooth prosthesis is virtually designed (1224). The designed patient-specific abutment and permanent tooth prosthesis can be created by, for example, sending data to a milling machine and/or a rapid prototype machine that is configured to create a physical patient-specific abutment and/or a physical-permanent tooth prosthesis that are both eventually installed in the mouth of the patient. Alternatively and/or in addition thereto, one or more rapid prototype models of the patient's mouth, including a replica of the gingival contours, can be fabricated based on the three-dimensional model. The rapid prototype model(s) with the permanent tooth prosthesis thereon can be used by a clinician to develop, for example, the permanent prosthesis.

After the patient-specific abutment and the permanent tooth prosthesis are created, the temporary abutment, the temporary abutment cap, and the temporary prosthesis are removed from the patient's mouth to expose the underlying dental implant (1226). The method is completed by installing the patient-specific abutment and the permanent tooth prosthesis on the dental implant as is known in the art (1228).

In addition to the above described method (1200), after the gingival tissue is at least partially healed, if a clinician determines that the predicted emergence profile of the patient's gingival tissue is inaccurate due to, for example, the tissue healing in an unpredicted manner or shape, modifications can be made to, for example, the three-dimensional model, the temporary prosthesis, the temporary abutment cap, etc. Specifically, the temporary prosthesis and the temporary abutment cap can be removed from the temporary abutment and the temporary prosthesis can be reshaped and/or modified to better shape the gingival tissue in preparation for installing the permanent components. In such an instance of physically modifying the temporary prosthesis after partial healing has occurred, the modified temporary prosthesis and temporary abutment cap is scanned to produce a third set of scan data. The third set of scan data can then be used in the same fashion as the second set of scan data was originally used. In essence, the third set replaces the second set and the three-dimensional virtual model is redesigned to include a newly predicted gingival emergence profile.

Alternatively, in the case that the clinician determines that the predicted emergence profile of the patient's gingival tissue is, for example, slightly inaccurate, but that physical modification of the temporary prosthesis is unnecessary, virtual manipulation of the three-dimensional virtual model can be made in lieu of physical modification such that the designed permanent components are based on a newly predicted gingival emergence profile that accounts for the slight inaccuracies of the original predicted profile.

While the illustrated embodiments have been primarily described with reference to the development of a patient-specific abutment for a single tooth application, it should be understood that the present invention is also useful in multiple-tooth applications, such as bridges and bars for supporting full or partial dentures. In those situations, the patient-specific abutment would not necessarily need a non-rotational feature for engaging the underlying implant(s) because the final prosthesis would also be supported by another structure in the mouth (e.g., one or more additional underlying implants), which would inherently achieve a non-rotational aspect to the design. In any event, using a scanning process to obtain the necessary information about the emergence profile shape of the gingiva and the dimensional and/or positional information for the implant(s) (via information markers in the temporary prosthetic assembly) can lead to the development of an aesthetically pleasing multiple-tooth system.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the present invention, which is set forth in the claims that follow.

What is claimed is:

1. A temporary prosthesis assembly for attachment to a dental implant, comprising:
   a temporary abutment including (i) at least one retention groove, (ii) an anti-rotational feature for non-rotationally mating with the dental implant, (iii) one or more informational markers, and (iv) a flange, at least a portion of the flange having a curved shape for shaping gingival tissue in an anatomic fashion;

a temporary abutment cap configured to be removably coupled to the temporary abutment so as to cover the informational markers and such that a bottom end of the temporary abutment cap aligns with the flange to provide a continuous extension of the curved shape of the flange for shaping the gingival tissue in an anatomic fashion, the at least one retention groove extending circumferentially about the temporary abutment to aid axial retention of the temporary abutment cap to the temporary abutment; and a temporary prosthesis coupled to the temporary abutment cap, the combination of the temporary prosthesis and the temporary abutment cap being removably coupled to the temporary abutment.

2. The temporary prosthesis assembly of claim 1, wherein the temporary prosthesis has a non-round shape for shaping the gingival tissue in an anatomic fashion.

3. The temporary prosthesis assembly of claim 1, wherein the temporary prosthesis is coupled to an outer surface of the temporary abutment cap through cement.

4. The temporary prosthesis assembly of claim 1, wherein the temporary abutment further includes a first anti-rotational structure, the temporary abutment cap further includes at least one projection configured to provide a snap-fit engagement with the at least one retention groove on the temporary abutment, and the temporary abutment cap further includes a second anti-rotational structure configured to slidably engage the first anti-rotational structure of the temporary abutment.

5. The temporary prosthesis assembly of claim 4, wherein the snap-fit engagement between the at least one projection and the at least one retention groove aids in providing a seal between the temporary abutment cap and the temporary abutment, the seal being provided below the snap-fit connection.

6. The temporary prosthesis assembly of claim 1, further comprising a monolithic fastening device configured to removably couple the temporary abutment to the dental implant, the temporary abutment cap including an aperture.

7. An abutment assembly for attachment to a dental implant, comprising:

a temporary abutment having a lower region and an upper region, the lower region including an anti-rotational feature for non-rotationally mating with the dental implant, the upper region including a first anti-rotational structure and at least one retention groove, a top surface of the temporary abutment including one or more informational markers providing information concerning the dental implant;

a temporary abutment cap configured to be coupled to the upper region of the temporary abutment, the temporary abutment cap having at least one projection configured to mate with the at least one retention groove of the temporary abutment, the temporary abutment cap having a second anti-rotational structure configured to slidably engage the first anti-rotational structure of the temporary abutment; and a monolithic fastening device configured to removably couple the temporary abutment to the dental implant, the temporary abutment cap including an aperture, wherein an outer surface of the temporary abutment cap is coupled with a temporary prosthesis such that the temporary prosthesis and the temporary abutment cap are removable from the temporary abutment permitting access to the informational markers, wherein the temporary abutment includes a flange, at least a portion of the flange having a curved shape for shaping gingival tissue in an anatomic fashion, and wherein the temporary abutment cap is configured to be removably coupled to the temporary abutment such that a bottom end of the temporary abutment cap aligns with the flange to provide a continuous extension of the curved shape of the flange for shaping the gingival tissue in an anatomic fashion.

8. The abutment assembly of claim 7, wherein the at least one retention groove is positioned on an outside surface of the upper portion of the temporary abutment and extends circumferentially about the upper portion of the temporary abutment to aid axial retention of the temporary abutment cap to the temporary abutment.

* * * * *